(12) United States Patent
Ganguli et al.

(10) Patent No.: US 11,845,084 B2
(45) Date of Patent: Dec. 19, 2023

(54) MICROCHIP HIGH DENSITY HANGING DROP THREE-DIMENSION CULTURE PLATFORM

(71) Applicants: The Board of Trustees of the University of Illinois, Urbana, IL (US); Mayo Foundation for Medical Education and Research, Rochester, MN (US)

(72) Inventors: Anurup Ganguli, Urbana, IL (US); Rashid Bashir, Champaign, IL (US); Panagiotis Z. Anastasiadis, Jacksonville, FL (US); George Vasmatzis, Oronoco, MN (US)

(73) Assignees: The Board of Trustees of the University of Illinois, Urbana, IL (US); Mayo Foundation for Medical Education and Research, Rochester, MN (US)

( * ) Notice: Subject to any disclaimer, the term of this patent is extended or adjusted under 35 U.S.C. 154(b) by 290 days.

(21) Appl. No.: 17/307,150

(22) Filed: May 4, 2021

(65) Prior Publication Data
US 2021/0339244 A1    Nov. 4, 2021

Related U.S. Application Data

(60) Provisional application No. 63/019,823, filed on May 4, 2020.

(51) Int. Cl.
*B01L 3/00* (2006.01)
*B01L 3/02* (2006.01)
(Continued)

(52) U.S. Cl.
CPC .......... *B01L 3/5088* (2013.01); *B01L 3/0262* (2013.01); *B01L 9/523* (2013.01); *C12M 21/08* (2013.01); *B01L 2400/024* (2013.01)

(58) Field of Classification Search
None
See application file for complete search history.

(56) References Cited

U.S. PATENT DOCUMENTS 8,906,685 B2    12/2014  Takayama et al.
8,945,912 B2    2/2015   Bashir et al.
(Continued)

FOREIGN PATENT DOCUMENTS

| CN | 101947124 A | * | 1/2011 | ............. A61B 17/43 |
|---|---|---|---|---|
| WO | WO 2019/071142 | | 4/2019 | |
| WO | WO 2020/190871 | | 9/2020 | |

OTHER PUBLICATIONS

Aizawa et al. (2012) Polymers used to influence cell fate in 3D geometry: New trends. Prog. Polym. Sci. 37, 645-658.
(Continued)

*Primary Examiner* — P. Kathryn Wright
(74) *Attorney, Agent, or Firm* — Leydig, Voit & Mayer, Ltd.

(57) ABSTRACT

Provided are methods and related devices for preparing a cell and tissue culture, including a hanging drop culture. Microwells are specially loaded with cell mixtures using a removable reservoir and forcing cells into the underlying microwells. The removable reservoir is removed and the cells partitioned into the individual microwells and covered by an immiscible layer of fluid. The microwells and immiscible layer is inverted and the cells in the microwells cultured. The microwells may have shape-controlling elements to control the three-dimensional shape of the culture.

19 Claims, 47 Drawing Sheets

(51) Int. Cl.
  *B01L 9/00* (2006.01)
  *C12M 3/00* (2006.01)

(56) References Cited

U.S. PATENT DOCUMENTS

| | | |
|---|---|---|
| 9,126,199 B2 | 9/2015 | Moritz et al. |
| 9,250,113 B2 | 2/2016 | Bashir et al. |
| 9,376,713 B2 | 6/2016 | Bashir et al. |
| 9,835,634 B2 | 12/2017 | Bashir et al. |
| 10,527,579 B2 | 1/2020 | Bashir et al. |
| 10,724,089 B2 | 7/2020 | Bashir et al. |
| 2014/0179561 A1 | 6/2014 | Takayama et al. |
| 2018/0023112 A1* | 1/2018 | Hallock ............ C12Q 1/689 506/26 |
| 2018/0119218 A1* | 5/2018 | Bashir ............ C12N 15/1003 |
| 2018/0250672 A1* | 9/2018 | Jamshidi ............ B01L 3/5088 |
| 2019/0011349 A1 | 1/2019 | Bashir et al. |
| 2020/0263244 A1 | 8/2020 | Bashir et al. |
| 2020/0391169 A1 | 12/2020 | Han et al. |

OTHER PUBLICATIONS

Anderson et al. (2006) Tumor Morphology and Phenotypic Evolution Driven by Selective Pressure from the Microenvironment. Cell 127, 905-915.
Arrowsmith et al. (2013) Phase II and Phase III attrition rates 2011-2012. Nat. Rev. Drug Discov. 12, 569.
Astashkina et al. (2014) Critical analysis of 3-D organoid in vitro cell culture models for high-throughput drug candidate toxicity assessments. Adv. Drug Deliv. Rev. 69-70, 1-18.
Avril et al. (2017) CD90 expression controls migration and predicts dasatinib response in glioblastoma. Clin. Cancer Res. 23, 7360-7374.
Baker et al. (2012) Deconstructing the third dimension—how 3D culture microenvironments alter cellular cues. J. Cell Sci. 125, 3015-3024.
Baker et al. (2016) Modeling Pancreatic Cancer with Organoids. Trends in Cancer 2, 176-190.
Beltran et al. (2015) Whole-Exome Sequencing of Metastatic Cancer and Biomarkers of Treatment Response. JAMA Oncol. 1, 466-474.
Benezra et al. (2012) Fluorine-labeled dasatinib nanoformulations as targeted molecular imaging probes in a PDGFB-driven murine glioblastoma model. Neoplasia 14, 1132-1143.
Binks et al. (2016) Oil-in-Oil Emulsions stabilised solely by solid particles, Soft Matter, 12, 876.
Boghaert et al. (2012) Host epithelial geometry regulates breast cancer cell invasiveness. Proc. Natl. Acad. Sci. U. S. A. 109, 19632-19637.
Boj (2015) Organoid Models of Human and Mouse Ductal Pancreatic Cancer. Cell 160, 324-338.
Carlson et al. (2011) Establishment, Maintenance, and In Vitro and In Vivo Applications of Primary Human Glioblastoma Multiforme (GBM) Xenograft Models for Translational Biology Studies and Drug Discovery. Current Protocols in Pharmacology, 52(14) 1-14.
Clevers (2016) Modeling Development and Disease with Organoids. Cell 165, 1586-1597.
Duarte et al. (2013) On-chip parallel detection of foodborne pathogens using loop-mediated isothermal amplification. Biomed. Microdevices 15, 821-830.
Fang et al. (2017) Three-Dimensional Cell Cultures in Drug Discovery and Development. SLAS Discovery vol. 22 456-472.
Frey et al. (2014) Reconfigurable microfluidic hanging drop network for multi-tissueC17 interaction and analysis. Nat. Commun. 5, 4250, 1-11.
Friedl et al. (2009) Collective cell migration in morphogenesis, regeneration and cancer. Nature Reviews Molecular Cell Biology, 10, 445-457.
Ganguli et al. (2018) Pixelated spatial gene expression analysis from tissue. Nat. Commun. 9, 202.
Ganguli et al. (Apr. 2021) Three-dimensional microscale hanging drop arrays with geometric control for drug screening and live tissue imaging. Sci. Adv. 7: eabc1323.
Gao et al. (2014) Organoid Cultures Derived from Patients with Advanced Prostate Cancer. Cell 159, 176-187.
Glicklis et al. (2004) Modeling mass transfer in hepatocyte spheroids via cell viability, spheroid size, and hepatocellular functions. Biotechnol. Bioeng. 86, 672-680.
Gomez et al. (2010) Tissue geometry patterns epithelial-mesenchymal transition via intercellular mechanotransduction. J. Cell. Biochem. 110, 44-51. doi:10.1002/jcb.22545.
Ingber (2005) Mechanical control of tissue growth: Function follows form. Proceedings of the National Academy of Sciences, 102, 11571-11572.
InSphero, Microtissue Formats. Available at: https://insphero.com/science/enabling-technology/microtissue-formats/. (Accessed: Mar. 27, 2019).
Jørgensen et al. (2014) Hanging drop cultures of human testis and testis cancer samples: a model used to investigate activin treatment effects in a preserved niche. Br. J. Cancer 110, 2604-2614.
Kovtun et al. (2015) Chromosomal catastrophe is a frequent event in clinically insignificant prostate cancer. Oncotarget 6, 29087-29096.
Kunz-Schughart et al. (1998) Multicellular spheroids: a three-dimensional in vitro culture system to study tumour biology. Int. J. Exp. Pathol. 79, 1-23.
Kwak et al. (2018) Mass fabrication of uniform sized 3D tumor spheroid using high-throughput microfluidic system. J. Control. Release 275, 201-207.
Lee et al. (2016) Interfacial geometry dictates cancer cell tumorigenicity. Nat. Mater. 15, 856-862.
Lewis-Tuffin et al. (2015) Src family kinases differentially influence glioma growth and motility. Mol. Oncol. 9, 1783-1798.
Long et al. (Jan. 2019) How the extracellular matrix shapes neural development. Open Biol. 9, 180216.
Ma et al. (2012) Multicellular Tumor Spheroids as an in Vivo—Like Tumor Model for Three-Dimensional Imaging of Chemotherapeutic and Nano Material Cellular Penetration. Mol. Imaging 11, 487-498. DOI 10.2310/7290.2012.00012.
Moroni et al. (2018) "Biofabrication strategies for 3D in vitro models and regenerative medicine," Nature Reviews Materials, 3, 21-37.
Mueller-Klieser (1997) Three-dimensional cell cultures: from molecular mechanisms to clinical applications. Am. J. Physiol. 273, C1109-C1123.
Murphy et al. (2012) Mate Pair Sequencing of Whole-Genome-Amplified DNA Following Laser Capture Microdissection of Prostate Cancer. DNA Res. 19, 395-406.
Murphy et al. (2014) Materials as stem cell regulators. Nature Materials vol. 13 547-557.
Murphy et al. (2016) Integrated analysis of the genomic instability of PTEN in clinically insignificant and significant prostate cancer. Mod. Pathol. 29, 143-156.
Nath et al. (2016) Three-dimensional culture systems in cancer research: Focus on tumor spheroid model. Pharmacology and Therapeutics vol. 163 94-108.
Nehoff et al. (2015) A combination of tyrosine kinase inhibitors, crizotinib and dasatinib for the treatment of glioblastoma multiforme. Oncotarget 6, 37948-37964.
Nelson et al. (2005) Emergent patterns of growth controlled by multicellular form and mechanics. Proc. Natl. Acad. Sci. U. S. A. 102, 11594-11599.
Ofek et al. (2008) Matrix Development in Self-Assembly of Articular Cartilage. PLoS One 3, e2795.
Pampaloni et al. (2007) the third dimension bridges the gap between cell culture and live tissue. Nat. Rev. Mol. Cell Biol. 8, 839-845.
Pauli et al. (2017) Personalized In Vitro and In Vivo Cancer Models to Guide Precision Medicine. Cancer Discov. 7, 462-477. doi:10.1158/2159-8290.CD-16/1154.
Pickl et al. (2009) Comparison of 3D and 2D tumor models reveals enhanced HER2 activation in 3D associated with an increased response to trastuzumab. Oncogene 28, 461-468.

(56) References Cited

OTHER PUBLICATIONS

Rennert et al. (2016) Development and validation of a whole-exome sequencing test for simultaneous detection of point mutations, indels and copy-number alterations for precision cancer care. npj Genomic Med. 1, 16019.

Rubin (2015) Health: Make precision medicine work for cancer care. Nature 520, 290-291.

Ryu et al. (Dec. 2019) Spheroid Culture System Methods and Applications for Mesenchymal Stem Cells. Cells 8, 1620.

Sil et al. (2011) Fibronectin-integrin ($\alpha 5\beta 1$) modulates migration and invasion of murine melanoma cell line B16F10 by involving MMP-9. Oncol. Res. 19, 335-348.

Smalley et al. (2005) Selective evolutionary pressure from the tissue microenvironment drives tumor progression. Semin. Cancer Biol. 15, 451-459.

Souza et al. (2010) Three-dimensional tissue culture based on magnetic cell levitation. Nat. Nanotechnol. 5, 291-296.

Tao et al. (Apr. 2020) Development of a tunable method to generate various three-dimensional microstructures by replenishing macromolecules such as extracellular matrix components and polysaccharides. Sci. Rep. 10, 6567.

Todhunter et al. (2015) Programmed synthesis of three-dimensional tissues. Nat. Methods 12, 975-981.

Tung et al. (2011) High-throughput 3D spheroid culture and drug testing using a 384 hanging drop array. Analyst 136, 473-478.

Vasmatzis et al. (Nov. 2019) "Integration of comprehensive genomic analysis and functional screening of affected molecular pathways to inform cancer therapy," Mayo Clin. Proc. 95, 306-318.

Yahya et al. (2014) Cell patterning for liver tissue engineering via dielectrophoretic mechanisms. Sensors (Switzerland) vol. 14 11714-11734.

Yang et al. (2017) High-Throughput Fabrication and Modular Assembly of 3D Heterogeneous Microscale Tissues. Small 13, 1602769.

Zhao et al. (2017) Three-Dimensional Cell Culture and Drug Testing in a Microfluidic Sidewall-Attached Droplet Array, Anal. Chem. 89, 19, 10153-10157.

\* cited by examiner

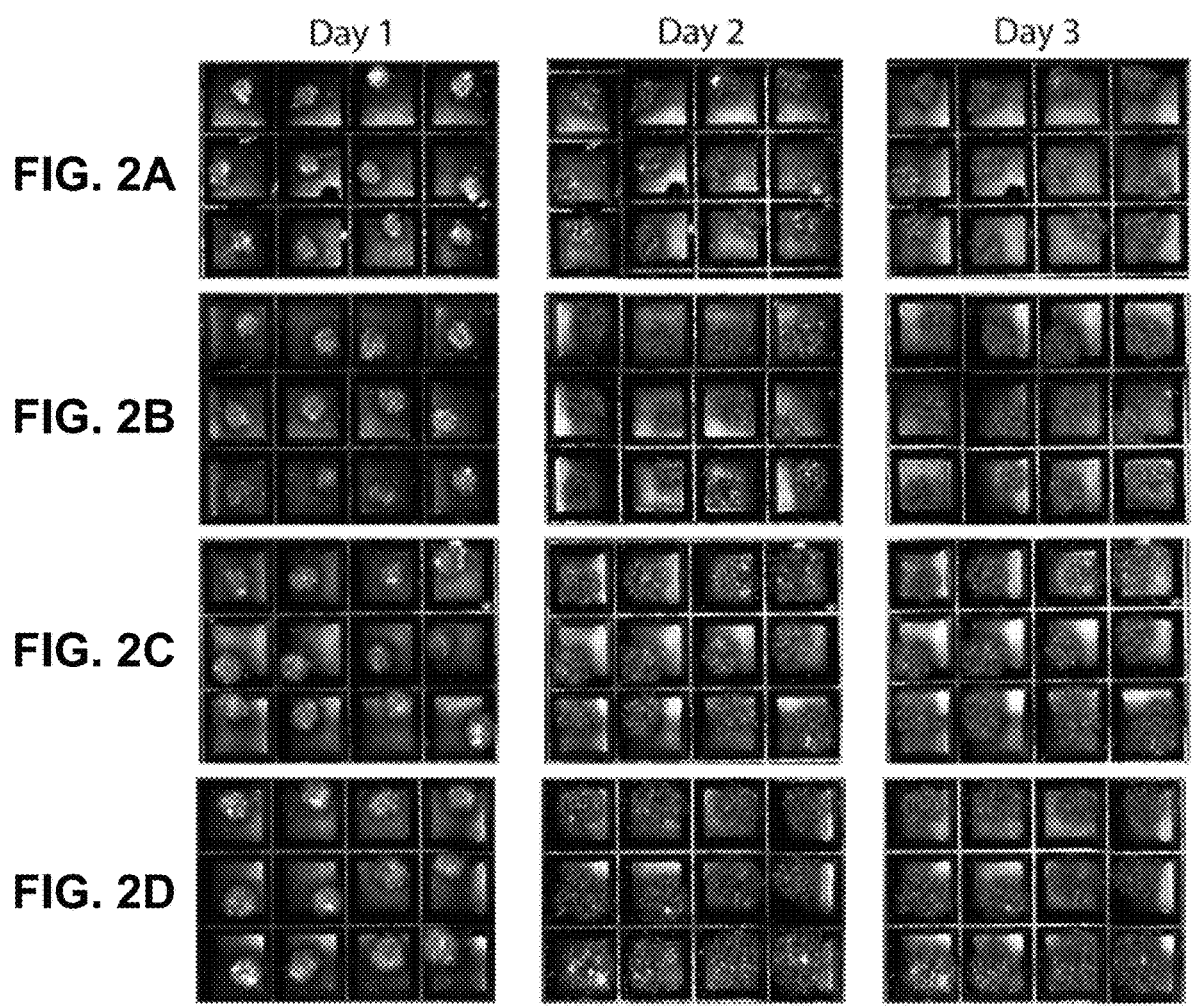

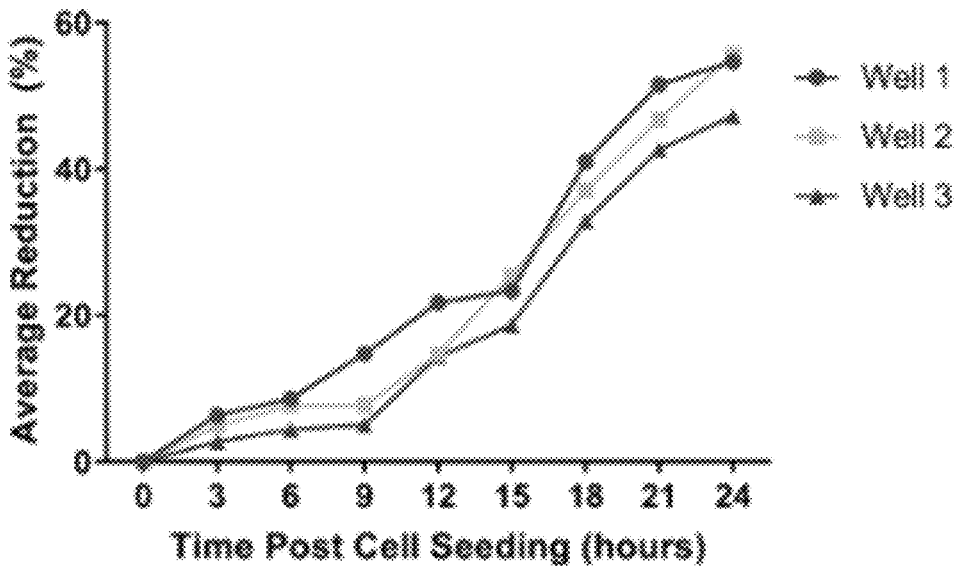
FIG. 3D
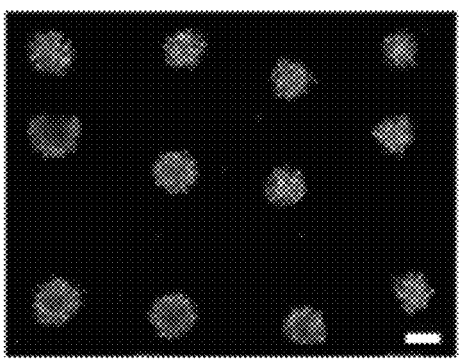
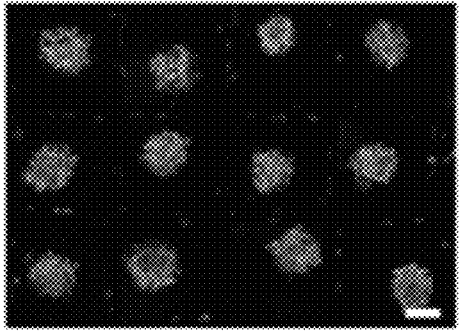
FIG. 3E

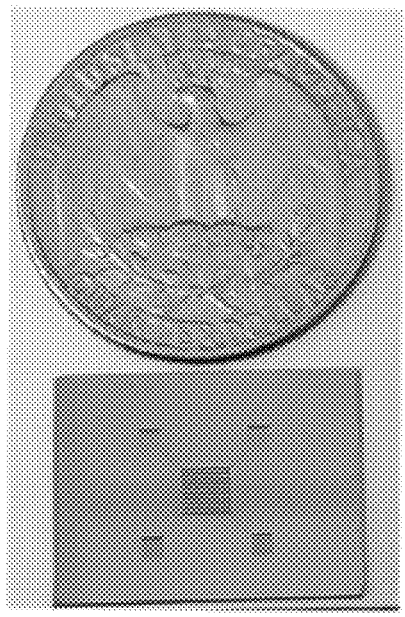
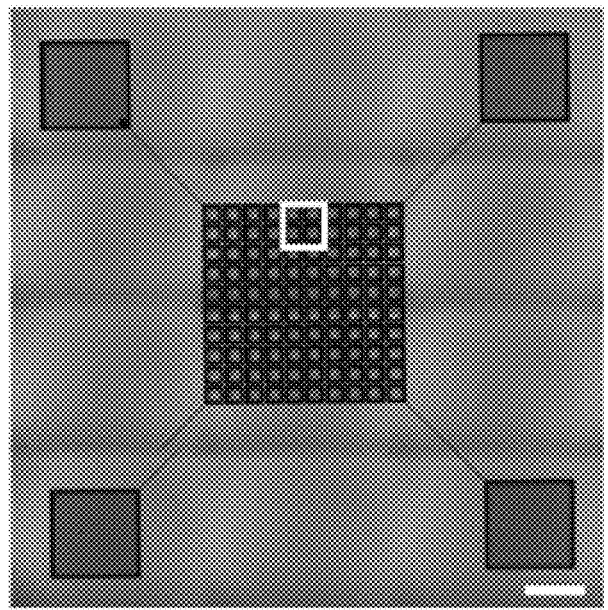
FIG. 7A  FIG. 7B
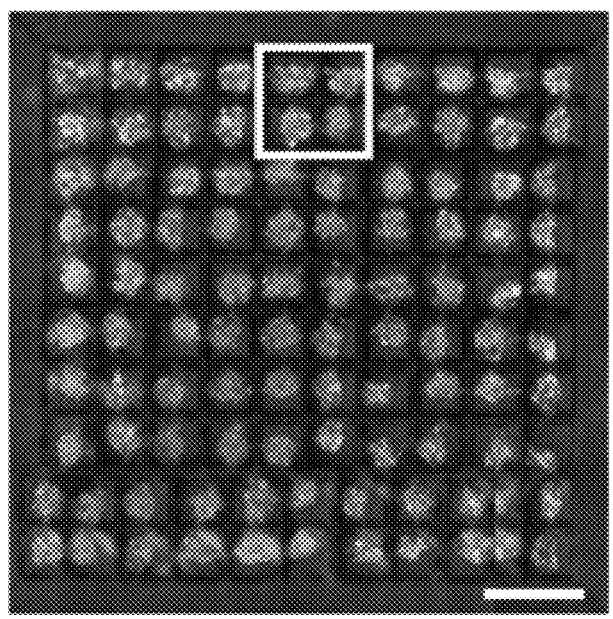
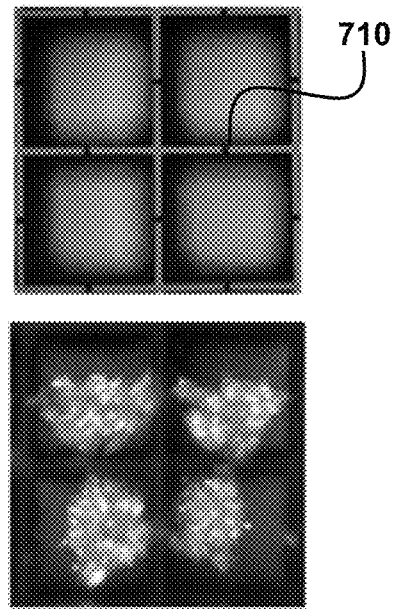
FIG. 7C

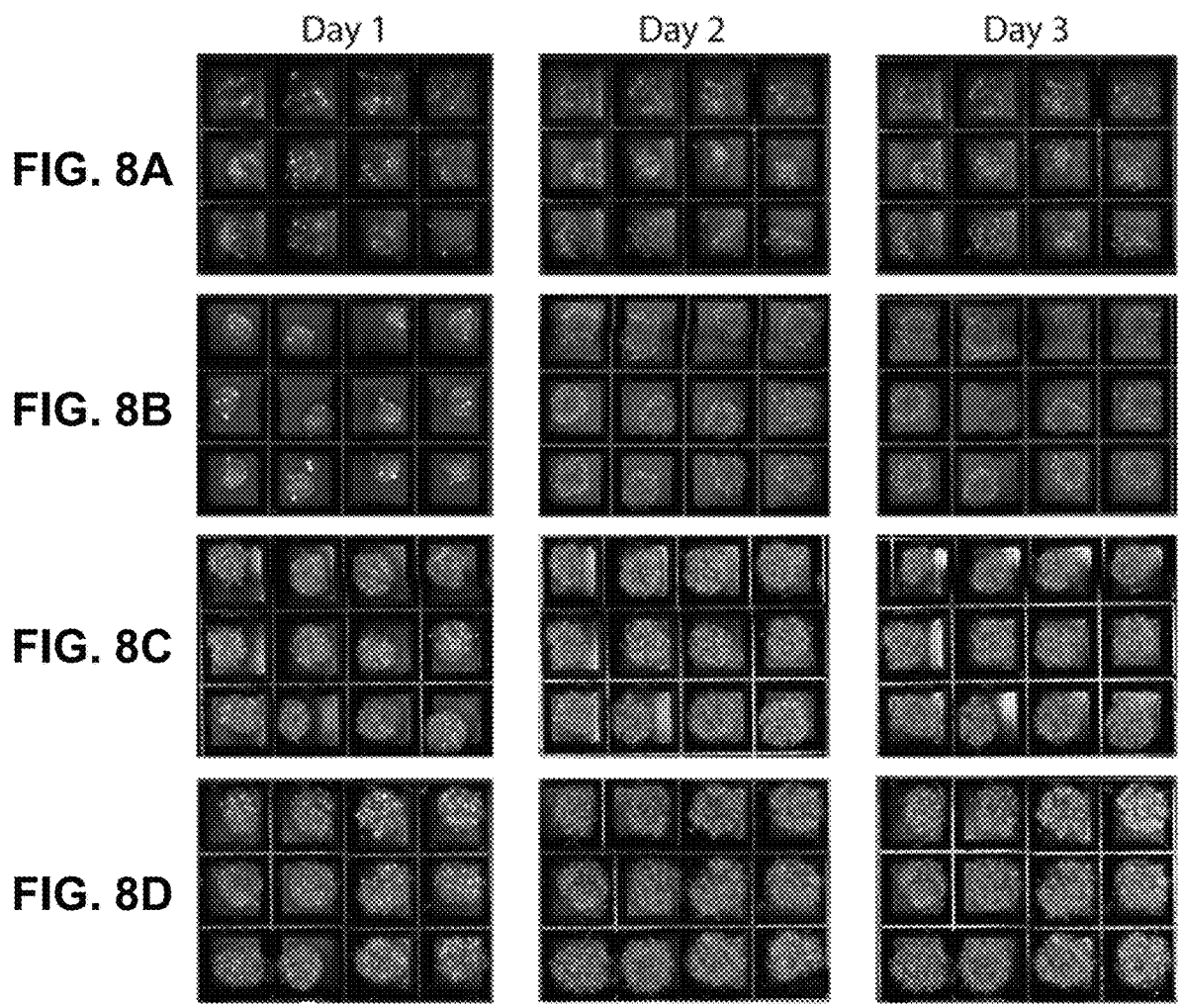

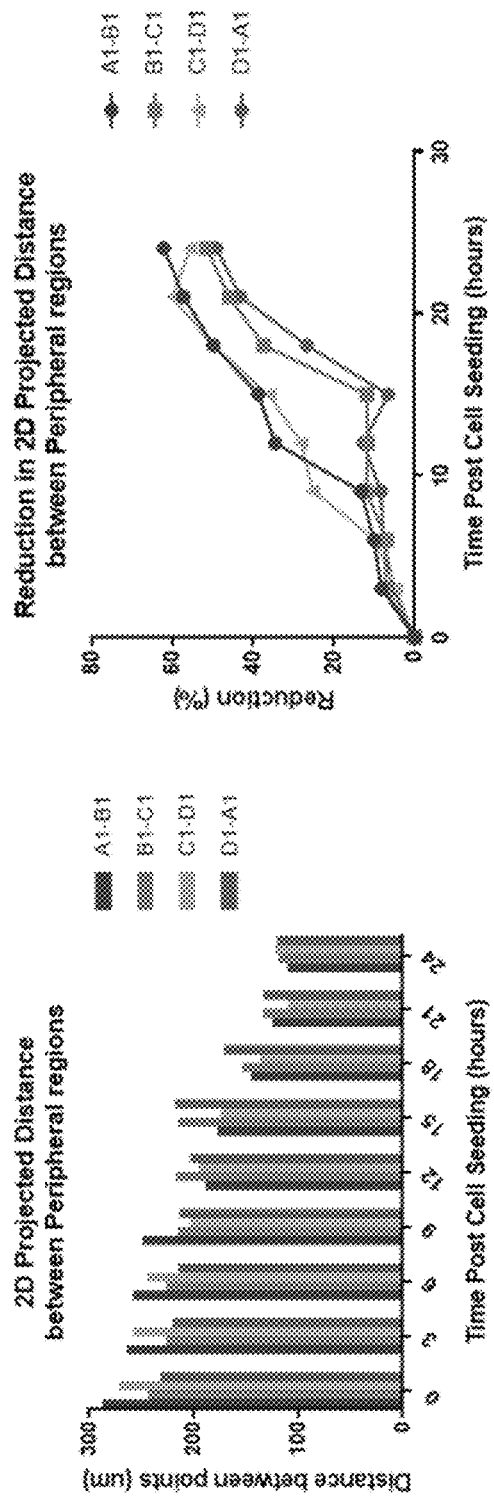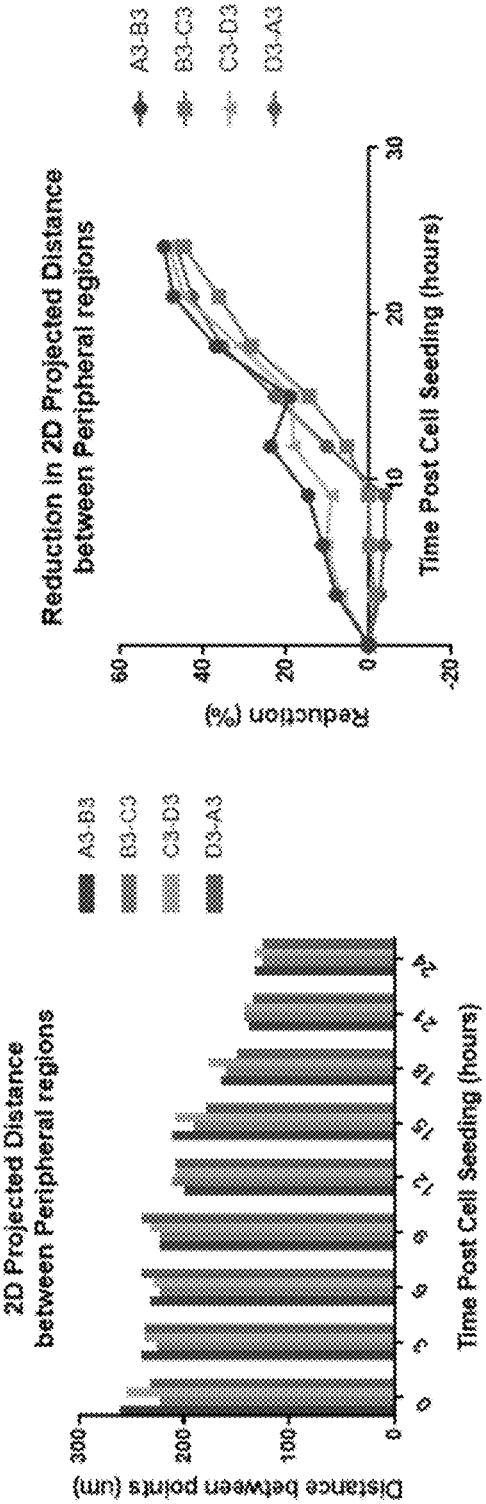
FIG. 11B
FIG. 11C

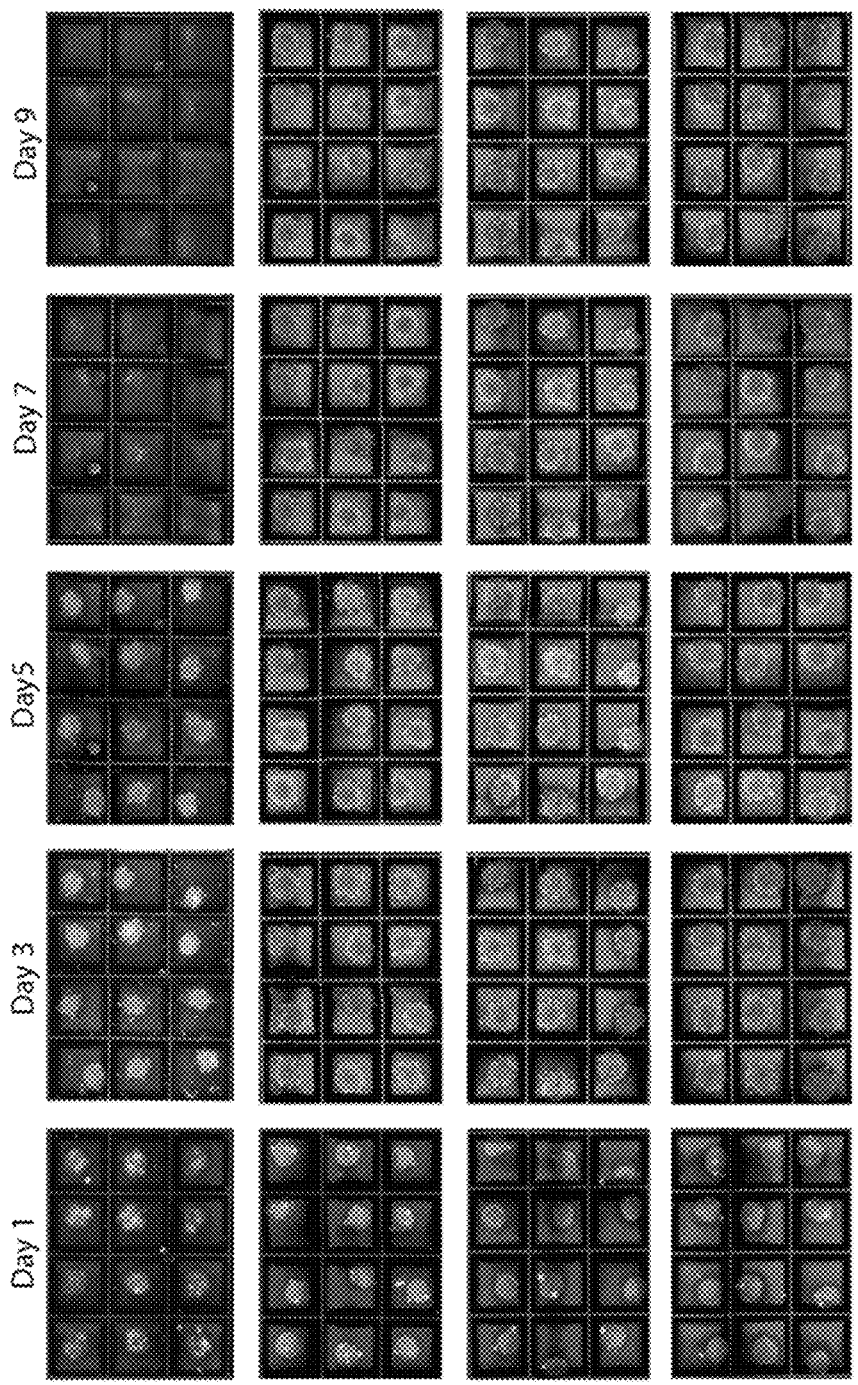

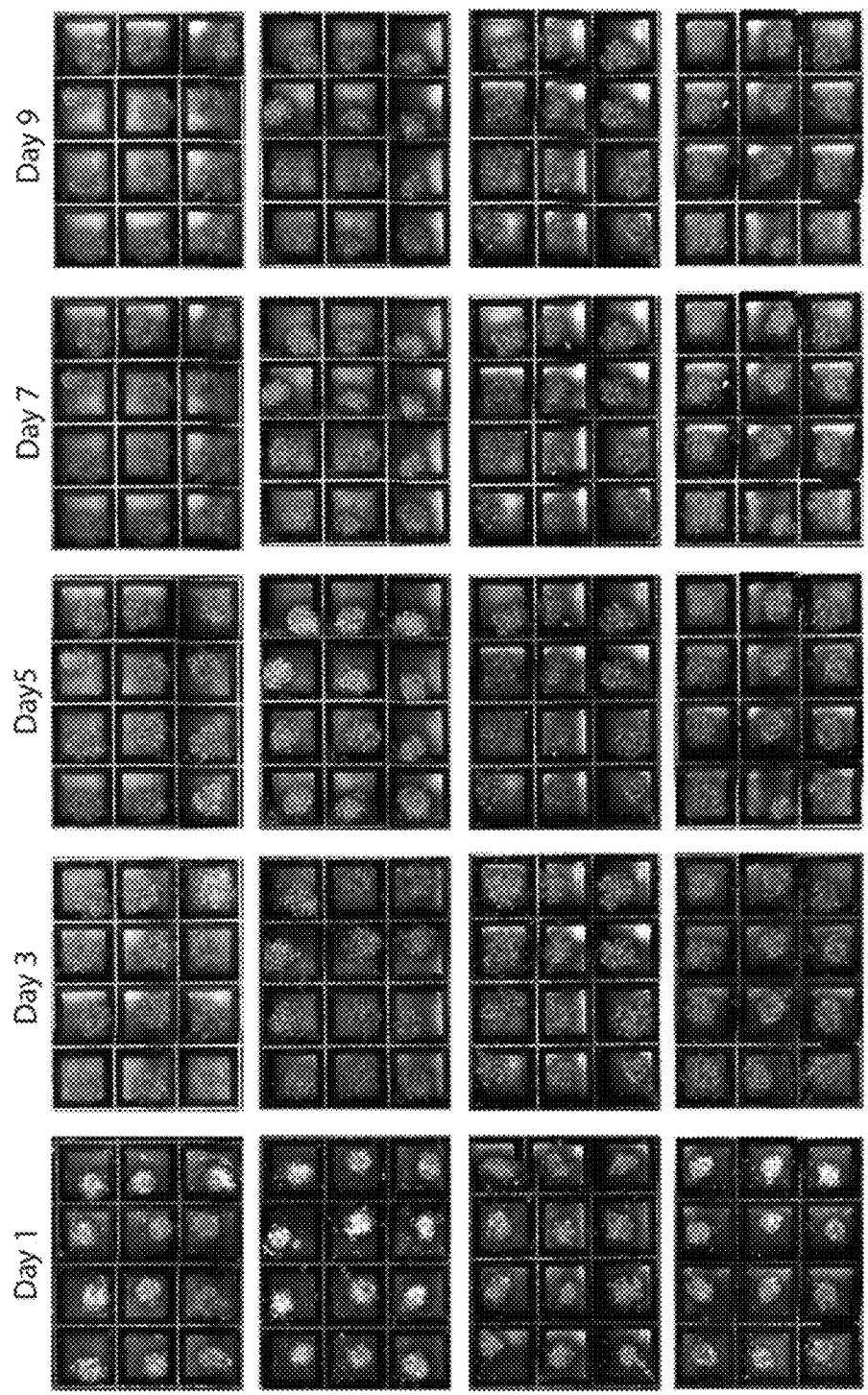

MICROCHIP HIGH DENSITY HANGING DROP THREE-DIMENSION CULTURE PLATFORM

CROSS-REFERENCE TO RELATED APPLICATIONS

This application claims the benefit of priority to U.S. Provisional Patent Application No. 63/019,823, filed May 4, 2020, which is hereby incorporated by reference in its entirety to the extent not inconsistent herewith.

STATEMENT REGARDING FEDERALLY SPONSORED RESEARCH OR DEVELOPMENT

This invention was made with Government support under R01 GM129709 awarded by the National Institutes of Health. The government has certain rights in the invention.

BACKGROUND OF INVENTION

Cell culture has been extensively applied in drug discovery, tissue engineering, and stem cell research. However, conventional two dimensional monolayer cultures do not replicate the important features of three dimensional (3D) conditions and much work has been done to elucidate the significant differences in cellular morphology, behavior and molecular signaling between the classic cell monolayer approaches and analogous 3D cultures. 3D culture systems offer the unique opportunity to grow cells such that the resulting tissues acquire morphological and cellular characteristics relevant to in-vivo conditions. Although several 3D culture techniques exist that deploy protein-based or synthetic polymer-based gel environments, rotation-based bioreactors, magnetic levitation and hanging drop techniques, their broad practical application has been limited due to several reasons. Matrix and hydrogel-based techniques are often used to generate organotypic cultures from isolated stem cells or tumor-initiating cells, but those techniques require cell proliferation and matrix engineering, as the scaffolds can introduce unpredictable cell-polymer interactions that influence and bias downstream applications of the organoids. Aggregation techniques such as magnetic levitation using nanoparticles to cause spheroid formation have demonstrated a limited number of spheroids and require cells to be pre-treated with magnetic beads at high concentrations adding complexity and potential toxicity.

A special consideration is that all proliferative models of drug testing, including 2D, 3D organoids, and patient-derived xenograft models, are subject to selective pressure and tumor evolution. Since the tumor-microenvironment has been increasingly recognized as a key contributor to cancer progression and resistance to therapy, removing selective pressure by optimizing culture conditions to maintain the tumor microenvironment are essential for accurate prediction of response to treatment. Ideally suited for this is the hanging drop technique where inverted 20-40 µL droplets containing cells held by capillary forces form tumor spheroids and commercial hanging drop plates in 96 and 384 well formats are now available. However, the conventional technology for performing hanging drop cultures is very laborious and low throughput, and requires the disruption of culture conditions and transfer of formed spheroids into a secondary plate for endpoint analysis. Those techniques are not compatible with direct live microscopy-based characterizations and also suffer from elevated osmolarity caused by evaporation of media from the droplets, which also limits the time for growth and analysis.

Engineering of tissues with tunable morphologies has been studied in 3D culture techniques such as bioprinting and micropatterning, but those techniques are known to cause high shear stress on cells during seeding. Guided assembly using magnetic levitation and nanoparticles has also been used to demonstrate the formation of annular ring structures using Glioblastoma human (GBM) cells. However, the formed structures in that platform are unable to retain shape during cellular compaction, and, pre-treatment with magnetic beads at high concentrations adds complexity and potential toxicity.

Although three-dimensional culture techniques are available, no single platform allows high replicates and high throughput for drug screening, ability to engineer interconnections between different 3D cultured microtissues, compatibility with direct on-chip real-time or high-resolution confocal microscopy, and geometric control of formed cell mass in 3D. Provided herein is a 'modular microchip hanging drop culture' where through simple microchip design elements, all the above features can be incorporated in a hanging drop 3D culture format. This particularly addresses the need in the art for improved cell and culture techniques to reliably control and influence a three-dimensional shape parameter of the cultured cell and tissue.

SUMMARY OF THE INVENTION

Provided herein is a modular microchip cell and tissue culture, including a hanging drop platform, that addresses the aforementioned problems in the art by providing a specially-configured array of microwells that are surface-oxidized and hydrophilic. The devices and methods provided herein can be utilized for drug screening, live imaging, and geometric control applications. The individual droplets with cells are held by capillary forces in microwells having micrometer-sized well characteristic dimensions for holding nano-litre sized culture volumes, including in the range of 1 nL to 10,000 nL, and subranges thereof, such as between about 10 nL and 1000 nL. For drug screening applications, the miniaturized and optimized culture conditions allow one cell-seeding step to produce an array of hundreds to hundreds of thousands of uniform tumor spheroids with diameters in the hundreds of micro-meters (and hence the term 'microcancers' or 'microcancer spheroids'). The methods and devices also provide the ability to reliably control various 3D shape parameters, including for tumor cell cultures, within a single high-throughput configuration.

In an embodiment, the method for preparing a cell and tissue culture comprises: providing an array of surface-oxidized, hydrophilic microwells. The microwells can have a variety of sizes and dimensions, but generally are characterized by dimensions that are micrometer-sized so that nanolitre sized volume samples are reliably and conveniently contained in the microwell without unwanted mixing between adjacent microwells. For example, each microwell may have a depth of between 50 µm to 1000 µm; a longest dimension of between 50 µm to 3000 µm; a separation distance from an adjacent microwell that prevents unwanted liquid leaking between adjacent microwells. For a circular cross-section microwell, the longest dimension may correspond to a diameter. For rectangular cross-section, the longest dimension may be a length, with a width that is less than the length. For a square cross-section, the longest dimension may be a side length or may be the hypotenuse formed between adjacent sides. For a triangle cross-section, the longest dimension may be the longest side. For a polygon, the longest dimension corresponds to the longest distance of the cross-section. For an elliptical cross-section, the longest dimension may correspond to the major axis. In this manner, any of a variety of cross-sectional shapes is readily described in terms of a convenient and well-defined "longest" dimension.

The method further comprises forming a removable reservoir over at least a portion of a top surface of the microwells; loading a mixture comprising cells in the removable reservoir and forcing the mixture comprising cells in the removable reservoir into the microwells; removing the removable reservoir from the microwells; covering the microwells with the mixture comprising cells with an immiscible layer; partitioning the cells into the individual microwells; inverting the array of microwells with the cells and the immiscible layer so that the immiscible layer confines the cells to the individual microwells; and culturing the cells in the inverted array of microwells, thereby preparing the cell and tissue culture.

The method is compatible with a range of microwell materials. Examples include, but are not limited to, surface-oxidized, hydrophilic microwells comprising one or more of silicon, oxide, glass, and/or plastic.

The method is compatible with any of a range of forcing steps, so long as the relevant biological material (e.g., cells and/or tissue) is reliably forced into their respective microwell(s). The forcing may be active such as by centrifugation, or may be more passive, such as by settling. Of course, other placement methods are compatible, including via direct pipetting, manual or via high-throughput automated registered transfer, or pull-down, including by electrical, magnetic and/or electromagnetic forces. As one example, forcing the mixture may comprise centrifuging the microwells and the mixture comprising cells in the removable reservoir at a centrifugal force of between 200 g to 400 g for a time period of between 2 minutes and 5 minutes.

The removable reservoir is a component that can be used to reliably and temporarily position the mixture comprising living biological cells over the microwells in preparation for the step that forces the mixture, specifically at least a portion of the cells in the mixture, into the underlying microwells.

The removable reservoir may comprise an array of microreservoirs addressed to at least a portion of the microwells. In this manner, different mixtures can be reliably provided to different microwells. The different mixtures may contain one or more of different cell density, different cell type(s), different tissues, and, more generally, any one or more of a desired different "starting" condition, whether that be from the biological cell(s) or tissue(s) or the suspending media.

The removable reservoir is compatible with any of a range of materials, so long as the material can be removed from the top surface of the microwells. For example, the removable reservoir may comprise polydimethylsiloxane (PDMS).

Any of a number of immiscible fluids may be used, so long as the fluid does not substantially mix with the fluid in the microwells, including a culture media. Preferably, the immiscible fluid is relatively high viscosity and surface tension so that upon inversion, the immiscible fluid does not significantly flow or otherwise move off the microwells top surface. In this manner, the fluid in the microwells is effectively isolated from the surrounding environment and undesirable evaporation or leakage prevented or minimized. For example, the immiscible fluid may comprise mineral oil and the cells in the microwells are provided in a culture media. As desired, a removable oxygen permeable cover slide may be provided over the immiscible fluid, particularly for those immiscible fluids that may be prone to evaporation and/or flow off the surface of the microwells, including via the force due to gravity.

The step of partitioning is particularly relevant in that it ensures the proper cell mixture is provided in each respective microwell, in a manner where cross-talk is avoided. Any of a variety of methods may be used to ensure appropriate partitioning, including as described in WO 2020/190871 to Bashir et al. titled "Spatially Mapped RNA Sequencing from Single Cells" (partitioning by "pixelization"); U.S. Pat. No. 10,724,089 titled "Spatial Molecular Analysis of Tissue" (partitioning by "pixelization"); WO 2019/071142 for forcing via fluidic and bead delivery, each of which are specifically incorporated by reference, including for forcing materials into an array of wells.

The immiscible layer is preferably a liquid and the partitioning step comprises applying a shear stress to the immiscible layer to remove excess liquid and reduce a thickness of the immiscible layer, including by forcing a gas over the microwells' surface and then introducing the immiscible layer. Alternatively, a flow of immiscible fluid may be introduced over the microwells, thereby removing excess fluid and covering the microwells with the immiscible fluid, while the culture media in the microwells is relatively undisturbed.

The partitioning step may comprise providing a hydrophobic removable reservoir and contacting a top surface of the hydrophobic removable reservoir with mineral oil. This can further assist in ensuring the culture media liquid in the microwells remains in the microwells.

The method may further comprise the step of measuring a change in a cell or tissue physical parameter and/or cell or tissue fluid in which the cell or tissue is immersed with a sensor embedded in the microwells. Exemplary sensors include optical sensors, temperature sensors, chemical sensors and/or pH sensors. The microsensors may be embedded in a bottom or a side surface of the microwells. Sensor output may be provided to a display and/or a time log recorded to a computer-readable medium to provide readout as a function of time. The sensors may be used to provide better micro-control or to study the response of the individual cultures.

The method may further comprise the step of performing on-chip real-time microscopy of the at least one cell and tissue culture without removal of any cell and tissue culture from a microwell or a component of the cell and tissue culture for changes in cell death and/or variations in cell and tissue cell culture volume over time on a microwell-by-microwell basis. The methods and devices provided herein are particularly advantageous in contrast to conventional systems that require removal of the culture from the well for reliable imaging. With this in mind, the microwells may be optically transparent for microscopy requiring light transmission through the microwell. Of course, the methods and devices are compatible with optically opaque microwells, with imaging and light illumination from one direction that is "above" the immiscible layer.

The method may further comprise the step of geometrically controlling a shape parameter in at least one cell and tissue culture by providing a microwell geometric shape, wherein the shape parameter is one or more of: cell and tissue culture size, volume, curvature, cross-sectional shape, a thickness, and/or a linear distance The geometrically controlling the shape parameter can result in generating a cell and tissue culture shape, including a sphere, rod, cube cylinder, toroid, or combination thereof, thereby generating a mechanical stress distribution on the cell and tissue culture to generate different cell phenotypes within the cell and tissue culture. This is particularly relevant as cell phenotype can be dependent, at least in part, on the physical forces exerted on the cell. Those physical forces, in turn, are dependent, at least in part, on the shape of the cell and tissue culture. The ability to precisely control shape is, therefore, a convenient means to control cell phenotype, and attendant response to various drug treatments and cellular behavior.

The methods provided herein have a number of advantages, including any one or more of: a time to form a multicellular spheroid in a plurality of microwells is one-day or less; the partitioning and immiscible layer avoids or minimizes selective pressure on the cell and tissue culture; the array of microwells number between 100 and 1,000,000 (providing reliable and readily controlled high-throughput); and/or each microwell has a volume that is less than 10 μL with an independently-controllable shape parameter testing of the cell and tissue culture geometry on a drug interaction. The combination of small volume, high-throughput, and reliable shape control is a powerful platform that provides a number of benefits not feasible with conventional culture systems.

For example, the methods are particularly well-suited for screening a drug for biological efficacy. "Biological efficacy" refers to the impact of a drug candidate on a biological cell, including a cancer cell or other biological disease condition. The impact may be in cell growth, cell death, cell proliferation, toxicity, morphology, phenotype and the like. The high-throughput, need for small cell and tissue volumes, and ability to reliably to control shape, is a particularly advantageous combination for rapid, efficient and increasingly reliable drug screen.

The drug screening method may comprise the steps of: preparing a cell and tissue culture according to any of the methods provided herein; incubating the cell and tissue culture with the drug to allow for contact between the drug and at least a portion of the cell and tissue cultures in the microwells; and evaluating impact of the drug on the cell and tissue cultures, thereby screening the drug for biological efficacy.

The cell and tissue culture may comprise cancer cells and the drug may be a cancer treatment candidate.

The method may further comprise the steps of: controlling at least one three-dimensional shape parameter of the at least one cell and tissue culture, wherein the three-dimensional shape parameter is one or more of size, volume, curvature, cross-sectional shape, a thickness, and/or a linear distance; and evaluating the impact of cell and tissue culture shape on the biological efficacy of the drug.

The response by the cell and tissue culture to the drug may be shape-dependent, with a heterogeneous response within the cell and tissue culture due to a stress gradient that varies over the cell and tissue culture due to the three-dimensional shape parameter that together forms an aggregate response. Accordingly, obtaining a map of cellular responses over various shaped culture to the drug candidate allows for examination of impact of cell stress (due to differences in shape) on response to the drug.

The method may further comprise the steps of: determining an in-vivo tumor morphology; and controlling the cell and tissue culture shape parameter to match the cell and tissue culture geometry to the in vivo tumor morphology.

The method may further comprise the step of controlling the at least one three-dimensional geometric parameter of the at least one cell and tissue culture by: forming a three-dimensional geometric shape in at least one of the microwells; wherein the three-dimensional geometric shape comprises an annulus having a cross-sectional shape, a size of the microwell, and/or a cross-sectional shape of the microwell.

The methods and devices are compatible with a controlled fluid exchange, including introduction via fluidic flow of substances for cell or tissue culture and any associated challenges, such as a drug candidate. In this aspect, the fluidic control may be by having each microwell fluidly connected to an adjacent microwell by a microwell interconnect. A cell and tissue culture media reservoir is fluidly connected to the array of microwells for introducing culture media and/or a drug to the cell and tissue culture. The method may further comprise the step of exchanging cell and tissue media in contact with the cell and tissue culture in the microwells by introducing a fresh media and/or a drug candidate to the cell and tissue culture media reservoir and flowing the fresh media and/or drug candidate to the microwells via the microwell interconnect.

In an embodiment, the invention is a device, specifically an array of microwells, for use with any of the methods described herein. For example, the device may be an array of microwells with fluid exchange for cell and tissue culture comprising: a substrate comprising an array of microwells wherein each microwell has a depth of between 80 μm to 160 μm and a longest dimension of between 100 to 500 μm; fluidic channels having a width of 5 to 15 μm that fluidly interconnect the microwells such that each individual microwell in the array is fluidly connected to an adjacent microwell; and at least one cell and tissue culture media reservoir well having a larger fluid capacity than the array of microwells, wherein said cell and tissue culture media reservoir well is fluidly connected to and positioned peripherally relative to the array of microwells. As previously described, the surface of the array of microwells are oxidized and surface treated to improve hydrophilicity. The substrate may comprise silicon, oxide, glass or plastic.

As described herein, microcancer size and volume can be controlled and readily varied through both chip design and cell seeding densities. Formed three-dimensional cultured cells and tissues, including spheroids, may be characterized in real-time without removing the culture from the microwells through upright fluorescence microscopy for tumor spheroid formation, cell death, and other processes. Exemplified herein are LN229 Human Glioblastoma cells and patient derived xenograft (PDX) Glioblastoma cells, also demonstrating compatibility with automated live cell imaging showing formation of the microcancers. Of course, the methods and devices provided herein are compatible with any of a range of cell types and tissues. Also illustrated is the capability to perform high-resolution confocal analysis to study the expression of protein markers directly on a chip without the need for extraction of the cultured cells or tissue, including tumor spheroids. To demonstrate that the platform does not bias tumor evolution by putting selective pressure, it is shown through the use of mate-pair sequencing, a complete overlap in chromosomal rearrangement events between the patient derived xenograft and the corresponding microcancers grown in the present platform. In one embodiment of the present technology, results are shown for direct drug testing on LN229 and PDX glioblastoma tumor spheroids formed in the hang drop culture platform as characterized by real-time optical microscopy. The nano-droplet culture model allows simultaneous testing of hundreds to hundreds of thousands of 3D microcancer cultures in real time where each microcancer captures the salient characteristics of the tumor. Because of the small size of the platform, smaller biopsies can be tested with many drugs. Drug testing can be done in days and the system also allows for sequential (staggered time point) drug testing. Therefore, this system makes it possible to rapidly test many drugs in real time even from clinical scenarios where only small biopsies are available.

Furthermore, geometric control in a 3D culture platform can be advantageous since tissue structures including size and shape facilitate the physiological function of the tissue by allowing cells and their microenvironment to exchange chemical, electrical and mechanical cues. The instant methods and systems are validated using human cells, including through the use of hanging drop culture, for geometric control of 3D cultured structures, including from Glioblastoma cells. Provided are microchips with etched channels, thereby facilitating chip fabrication with different well shapes, including circular, square, and triangular annular wells. This allows the media droplet shape to conform to the shape of channel cavity due to capillary forces. Using this approach, dense and continuous annular circle, square, and triangle 3D shapes are generated ranging in sizes from greater than one hundred micrometers to several millimeters, including reliably on the order of a few hundred micrometers. The present platform opens up applications of hanging drop culture where different cell types can be co-cultured in 3D on-chip to generate self-assembled and self-organized tissues with the salient in vivo-like features naturally formed via cell-cell interactions.

In summary, three-dimensional cultures provided herein produce conditions that recapitulate morphological and cellular characteristics relevant to in-vivo tissue and tumors. Nanoliter-accomodating volume wells or channels may be etched in a substrate, including a silicon substrate, where droplets with cells and corresponding culture media are held by capillary forces inside a fluid that is immiscible with the culture media, such as oil, including an inert mineral oil. For high-throughput drug screening applications, an array of hundreds to thousands of such microwells can be formed and loaded to form spheroids in a single step. Because the miniaturized hanging drop cultures require only hundreds of cells, a smaller biopsy volume can be used without sacrificing throughput or accuracy. Aggregation of cells into multicellular spheroids can occur in less than one day due to increased cell-cell interactions within the nano-droplet and without the need for any specific medium or matrices that can put selective pressure and bias the tumor evolution during culture.

Microchip hanging drop culture arrays are grown from any of a variety of cells, including cell lines, biopsies, or animal or human tissue. Exemplary cells include human LN229 glioblastoma and patient-derived mouse xenograft cells, with mate-pair sequencing performed to establish that the key genomic alterations of the original tumor is retained in the microchip cultures. Spatial protein expression is tracked within the resulting spheroids and response to drug over time measured with real time microscopy directly on chip. Finally, by engineering the droplet to form geometric shapes on the microchip, the geometry of cultured cell mass is manipulated. Taken together, these results indicate the broad applications of the present microchip hanging drop technology in advancing personalized medicine for cancer and drug discovery, tissue engineering, and stem cell research.

In an aspect, a method is provided for preparing a hang drop culture comprising: (a) providing an array of silicon microwells wherein each microwell is etched to a depth of 50 to 1000 µm, wherein each mircowell has a longest dimension from 50 to 3000 µm, wherein the well spacing is at least 5 µm, wherein the surface of the microwells has been oxidized after formation of the wells and wherein the surface of the microwells has been treated to improve hydrophilicity; (b) contacting the top of the array of silicon microwells with a detachable well array and allowing for temporary adhesion between the array of silicon microwells and the well array; (c) loading a mixture comprising cells in the well array and centrifuging the array of silicon microwells and the well array to pull the cells down into the silicon microwells; (d) removing the well array; (e) partitioning the cells into the individual silicon microwells; and (f) inverting the array of silicon microwells on the surface of a mineral oil and incubating the mixture comprising cells under cell culture conditions whereby at least one hang drop culture is formed, wherein the partitioning in step (e) is performed by application of a mineral oil to the top of the array of silicon microwells and applying a shear force of air, wherein the partitioning in step e occurs automatically by providing a hydrophobic well top surface and contacting the hydrophobic well top surface with mineral oil wherein the centrifugation of step (c) is performed within the range of 200 to 400 g for 2 to 5 minutes, wherein each mircowell has a longest dimension from 200 to 400 µm, wherein each microwell has a longest dimension from 250 to 350 µm, wherein each microwell is etched to a depth of 100 to 140 µm, wherein each microwell is etched to a depth of 110 to 130 µm, wherein the well spacing is from 15 to 25 µm, wherein the well array comprises polydimethylsiloxane (PDMS), wherein the surface of the microwells has been treated by exposure to oxygen plasma to improve hydrophilicity, sterility or both.

In another aspect, a method of drug testing is provided comprising (A) preparing a hang drop culture comprising: (a) providing an array of silicon microwells wherein each microwell is etched to a depth of 80 to 160 µm, wherein each mircowell has a longest dimension from 100 to 500 µm, wherein the well spacing is from 10 to 30 µm, wherein the surface of the microwells has been oxidized after formation of the wells and wherein the surface of the microwells has been treated to improve hydrophilicity; (b) contacting the top of the array of silicon microwells with a detachable well array and allowing for temporary adhesion between the array of silicon microwells and the well array; (c) loading a mixture comprising cells in the well array and centrifuging the array of silicon microwells and the well array to pull the cells down into the silicon microwells; (d) removing the well array; (e) partitioning the cells into the individual silicon microwells; and (f) inverting the array of silicon microwells on the surface of a mineral oil and incubating the mixture comprising cells under cell culture conditions whereby at least one hang drop culture is formed, (B) placing the array of silicon microwells upright inside a mineral oil; (C) centrifuging the array to pull the cells down into the silicon microwells; (D) loading the drug to be tested on the array of silicon microwells through the mineral oil; (E) incubating the hang drop culture with the drug to allow for diffusion of the drug; (F) partitioning the cells into the individual silicon microwells; and (G) inverting the array of silicon microwells on the surface of a mineral oil, incubating the mixture comprising cells under cell culture conditions in the presence of the drug, and evaluating results of drug application.

In an aspect, a method for preparing a hand drop culture is provided comprising: (a) providing an array of silicon microwells wherein each microwell is etched to a depth of 80 to 160 µm, wherein the shape of each mircowell is selected from the group consisting of an annular circle, a square and an annular triangle and has a longest dimension from 50 to 200 µm, wherein the surface of the microwells has been oxidized after formation of the wells and wherein the surface of the microwells has been treated to improve hydrophilicity; (b) contacting the top of the array of silicon microwells with a detachable well array and allowing for temporary adhesion between the array of silicon microwells and the well array; (c) loading a mixture comprising cells in the well array and centrifuging the array of silicon microwells and the well array to pull the cells down into the silicon microwells; (d) removing the well array; (e) partitioning the cells into the individual silicon microwells; and (f) inverting the array of silicon microwells on the surface of a mineral oil and incubating the mixture comprising cells under cell culture conditions whereby at least one hang drop culture is formed, wherein the microwells are shaped as annular circles and the width of the microwells ranges from 70 to 100 µm, wherein the microwells are shaped as squares and the width of the microwells ranges from 70 to 100 µm, wherein the microwells are shaped as annular triangles and the width ranges from 120 to 160 µm, wherein the partitioning in step (e) is performed by application of a mineral oil to the top of the array of silicon microwells and applying a shear force of air, wherein the centrifugation of step (c) is performed at within the range of 200 to 400 g for 2 to 5 minutes, wherein each microwell is etched to a depth of 100 to 140 µm, wherein each microwell is etched to a depth of 110 to 130 µm, wherein the well array comprises polydimethylsiloxane (PDMS), wherein the surface of the microwells has been treated to improve hydrophilicity by exposure to oxygen plasma.

In another aspect, a method for preparing a hang drop culture with fluid exchange is provided comprising: (a) providing an array comprising silicon microwells wherein each microwell is etched to a depth of 80 to 160 µm, wherein each mircowell has a longest dimension from 100 to 500 µm, wherein fluidic channels having a width of 5 to 15 microns fluidly connect the microwells such that each individual microwell on the array is connected to each of its neighboring microwells, wherein reservoir wells having larger fluid capacity than the microwells are fluidly connected to and located peripheral to the microwells on the array, wherein the surface of the microwells has been oxidized after formation of the wells and wherein the surface of the microwells has been treated to improve hydrophilicity; (b) contacting the top of the array with a detachable well array and allowing for temporary adhesion between the array and the well array; (c) loading a mixture comprising cells in the well array and centrifuging the array and the well array to pull the cells down into the silicon microwells; (d) removing the well array; (e) partitioning the cells into the individual silicon microwells; (f) inverting the array on the surface of a mineral oil and incubating the mixture comprising cells under cell culture conditions whereby at least one hang drop culture is formed; and (g) exchanging media in contact with the cells by addition of fresh media to at least one reservoir for fluid transport across at least one fluidic channel to at least one microwell, wherein the partitioning in step (e) is performed by application of a mineral oil to the top of the array of silicon microwells and applying a shear force of air, oil or both, wherein the centrifugation of step (c) is performed at 200 g for 2 minutes, wherein each mircowell has a longest dimension from 200 to 400 µm, wherein each mircowell has a longest dimension from 250 to 350 µm, wherein each microwell is etched to a depth of 100 to 140 µm, wherein each microwell is etched to a depth of 110 to 130 µm, wherein the well array comprises polydimethylsiloxane (PDMS), wherein the surface of the microwells has been treated to improve hydrophilicity by exposure to oxygen plasma.

In another aspect, an array of silicon microwells with fluid exchange is disclosed comprising: (a) a substrate comprising silicon microwells wherein each microwell is etched to a depth of 80 to 160 µm and wherein each mircowell has a longest dimension from 100 to 500 µm; (b) fluidic channels having a width of 5 to 15 microns fluidly connecting the microwells such that each individual microwell on the array is connected to each of its neighboring microwells; and (c) at least one reservoir well having a larger fluid capacity than the microwells wherein said reservoir well is fluidly connected to and located peripheral to the microwells, wherein the surface of the microwells has been oxidized after formation of the wells and wherein the surface of the microwells has been treated to improve hydrophilicity, further wherein exchange of media in the silicon microwells may be performed by addition of fresh media to the at least one reservoir well for fluid transport across at least one fluidic channel to at least one microwell.

The methods provided herein may also include making any of the described microwells. For example, the method for making will depend, at least in part, on the material that the microwells are formed from. For example, for a plastic substrate, the microwells may be formed from an injection molding procedure, such as a molded plastic. Other methods include, but are not limited to, etching and/or deposition, phase mask lithography, and the like. In an embodiment, the method further comprises the step of: providing a silicon layer; etching the silicon layer to form an array of silicon microwells; oxidizing the array of silicon microwells; and treating a surface of the array of silicon microwells to increase hydrophilicity of the array of silicon microwells. In this manner, the silicon microwells are surface-oxidized hydrophilic silicon microwells. The oxidization may be by exposing a surface of the array of silicon microwells to oxygen plasma to increase hydrophilicity, sterility, or both. The oxidization may be by one or more of chemical, electrolytic and/or thermal.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 1A shows overall process flow schematic. Chips are made hydrophilic through oxygen plasma at 300 W for 3 min. Cell solution in media is loaded on chip into the PDMS reservoir and centrifuged at 200 g for 2 min. Then, the chip is dipped in mineral oil and air pressure (or oil shear) is applied to shear off excess media and digitize the wells. Finally, the chip is inverted for 3D microcancer formation. FIG. 1B shows optical image of two microarray chips beside a quarter. The first chip (top) is an array of 900 microwells of 300 um well size. The second chip (bottom) includes a gradient of well sizes for spheroid formation. FIG. 1C shows fluorescence image of microcancer spheroid formation of gradient sizes seen 1 day after cell seeding. High throughput organoid formation is possible with a single cell seeding step. Easy optical characterization with an upright microscope is shown. (scale bar: 500 um) FIG. 1D shows volumetric mapping of spheroids in white box seen in FIG. 1C. One of each microcancer size is highlighted. (scale bar: 500 um) FIG. 1E shows bar graph of microcancer volumes for spheroids in each well size variation for days 1-3 post cell seeding. The data encompasses volumes of 3 microcancers (n=3) for each condition. Linear fit of Day 3 mean volumes has an r-squared value of 0.97 indicating a linear relationship and control between well and spheroid sizes. FIG. 1F shows bar graph of cell death (green volume normalized to red volume) for spheroids in each well size variation for days 1-3 post cell seeding. The data encompasses cell death data of 3 microcancers (n=3) for each condition. Bar graphs and error bars indicate mean and standard deviation, respectively.

FIGS. 2A-2L. On-chip PDX culture. FIGS. 2A-2D show maximum projections of formed microcancers in 12 well culture for days 1-3 post cell seeding of 300 cells per well (FIG. 2A), 500 cells per well (FIG. 2B), 700 cells per well (FIG. 2C), and 1000 cells per well (FIG. 2D). Each well has a side length of 300 um (for scale). FIGS. 2E-2F, Box and whiskers plot of microcancer volumes (FIG. 2E) and cell death (green volume normalized to red volume) (FIG. 2F) for each cell variation type for days 1-3 post cell seeding. The data encompasses volume and cell death information of microcancers from the 12 wells (n=12) seen for each condition. FIGS. 2G-2H, Mate pair sequencing demonstrates high degree of relatedness and similar genomic abnormalities between the original PDX tumor and 3D cultured PDX spheroids. Genome plots depict genomic rearrangements in original PDX (FIG. 2G) and 3D cultures (FIG. 2H) grown in an array platform as disclosed herein. Each line represents an abnormal rearrangement in two loci in chromosome numbers delineated on the right and the left side of each panel. The genome plot for the 3D culture (FIG. 2H) was generated by merging the results of 3 separately cultured experimental repeats. FIG. 2I Distributions of UMI counts in GEM cells. Counts are log 2-transformed after adding on 0.5 to avoid logging 0 values. Summed UMI counts from mouse genes (Top). Summed UMI counts from human genes (Bottom). FIG. 2J, Distributions of numbers of genes with >1 UMI in each GEM cell. Counts were log 2-transformed after adding on 0.5 to avoid logging 0 values. Total number of mouse genes with >1 UMI (Top). Total number of human genes with >1 UMI. Line shows threshold of 64 genes detected (6 on log 2 scale) (Bottom). UMAP plots are constructed for genes of interest from micro-cancers grown on chip (n=7,653). Each dot represents the transcriptome of a single cell from dissociated micro-cancers. These showed the single-cell gene expression of key markers for gliomas and glioma stem cells (FIGS. 2K & 2L). Scale bars represent z-test-normalized gene counts.

FIGS. 3A-3G. Capturing real-time microcancer spheroid formation with live cell imaging on inverted microscope and molecular characterizations of spheroids in microwell array. FIG. 3A shows time progression of formation of 5 microcancers (LN 229 cells) on the platform, imaged on an automated inverted microscope culture setup every 3 hours. (scale bar: 300 um) FIG. 3B shows 2D projected distance between peripheral cell clusters in well 2 over 24 hours. These regions are shown in white circles and labeled in FIGS. 3A, 3C show reduction (%) from time "0" in 2D projected distance between peripheral cell clusters in well 2 over 24 hours. FIG. 3D shows average reduction (%) from time "0" in 2D projected distance between peripheral cell clusters for all 3 wells over 24 hours. e-g, Immunofluorescence detection of N-cadherin (red), DAPI nuclear staining (blue), and Human Mitochondria staining (green) in microcancers formed with LN229 cells and patient derived xenograft. Tile of 12 well culture of LN229 microcancers (top) and PDX microcancers (bottom) imaged directly on chip (scale bar: 100 um) (FIG. 3E). High resolution images of individual microcancers for LN229 and PDX (scale bar: 20 um) (FIG. 3F). Confocal z-stack images of PDX microcancer three days after cell seeding. Distance between each Z-stack slice is 10 um (Scale bar: 20 um) (FIG. 3G).

FIG. 4A, Maximum projections of 12 well cultures of LN229 spheroids for days 1-9 post cell seeding (initial cell concentration: 500 cells/well). On Day 3 post imaging, Dasatinib was loaded onto the chips. Final concentrations of drug added were 10 uM (top row), 100 nM (middle row), and Negative Control (bottom row). For Negative Control, only media and Celltox green dye was added. Each well has a side length of 300 um (for scale). FIGS. 4B-C, Box and whiskers plot of volumes (FIG. 4B) and cell death (FIG. 4C) (green volume normalized to red volume per well) of LN 229 microcancer spheroids from each drug concentration type for days 1-9 post cell seeding. The data encompasses volumes and cell death information of microcancers for the 12 wells (n=12) seen above for each condition. FIG. 4D shows the IC50 value for LN229 spheroids was calculated to be 95.9 nM as measured on day 9. The IC50 curve shown is based on 12 well data for each concentration of drug (10 uM to 100 pM and negative control), where the error bars represent the standard error of mean. FIG. 4E shows maximum projections of 12 well cultures of PDX spheroids for days 1-9 post cell seeding (initial cell concentration: 500 cells/well). On Day 3 post imaging, Dasatinib was loaded onto the chips. Final concentrations of drug added were 10 uM (top row), 100 nM (middle row), and Negative Control (bottom row). Each well has a side length of 300 um (for scale). FIGS. 4F-G show box and whiskers plot of volumes (FIG. 4F) and cell death (FIG. 4G) (green volume normalized to red volume per well) of PDX microcancer spheroids from each drug concentration type for days 1-9 post cell seeding. The data encompasses volumes and cell death information of microcancers for the 12 wells (n=12) seen above for each condition. FIG. 4H shows the IC50 value for PDX spheroids was calculated to be 13.8 nM as measured on day 9. The IC50 curve shown is based on 12 well data for each concentration of drug (10 uM to 100 pM and negative control), where the error bars represent the standard error of mean.

FIG. 5A shows process flow 3D shape formation. Chip with annular circle, square, and triangle channels is fabricated such that the depth of the channel is ~150 um. Internal well surfaces are made hydrophilic through oxygen plasma, after which cells with media are loaded in a single step and centrifuged. Oil shear is performed for droplet formation, as the cavity between outer border of the channel and inner post causes the droplet to conform to the channel shape. The chip is inverted for hanging drop, and post 24 hours incubation of cells, dense 3D shapes are generated. FIG. 5B shows fluorescence image of shape formation of different sizes seen 1 day after cell seeding. Outer diameter (circle) or side lengths (square and triangle) of shape channels are mentioned on top left corner of each image. FIG. 5C shows volumetric mapping of the shapes in the green box seen in FIGS. 5B, 5D, Bar graph of volumes of annular circle, square, and triangle shapes for each channel size for day 1-3 post cell seeding. FIG. 5E shows bar graph of cell death (green volume normalized to red volume) in annular circle, square, and triangle shapes for each channel size for days 1-3 post cell seeding.

FIGS. 7A-7C. Interconnected network for spheroid interaction. FIG. 7A shows optical image of interconnected network microarray chip beside a quarter. FIG. 7B shows microscopic image of interconnected network array. The array consists of 100 microwells of 300 um size. Each of the wells are interconnected with 10 um spacing in between each of the wells. There are large reservoirs (1 mm side lengths) at the four corners of the chip connecting to the wells through a 10 um channel, which can be used for media exchange or drug testing. (Scale bar: 940 um) FIG. 7C shows fluorescence image of interconnected microcancer spheroid formations seen 1 day after cell seeding (Scale bar: 620 um). Etched ducts between the wells (top right) allows for spheroid communication (bottom right). The zoomed-in images are for the highlighted white boxes. Each well has a side length of 300 um (for scale).

FIGS. 8A-8F. On-chip LN229 glioblastoma cell culture. FIGS. 8A-D, Maximum projections of formed microcancer spheroids in 12 well culture for days 1-3 post cell seeding of FIG. 8A 300 cells per well, FIG. 8B 500 cells per well, FIG. 8C 700 cells per well and FIG. 8D 1000 cells per well. Each well has a side length of 300 um (for scale). FIGS. 8E-8F, Box and whiskers plot of FIG. 8E microcancer volumes and FIG. 8F cell death (green volume normalized to red volume) for each cell variation type for days 1-3 post cell seeding. The data encompasses volumes or cell death information of microcancers for the 12 wells (n=12) seen above for each condition.

FIGS. 9A-9D, Line graphs for FIG. 9A 300 cells per well, FIG. 9B 500 cells per well, FIG. 9C 700 cells per well, FIG. 9D 1000 cells per well microcancers to track growth and cell death post cell seeding and pre drug testing.

FIGS. 10A-D, Line graphs for FIG. 10A 300 cells per well, FIG. 10B 500 cells per well, FIG. 10C 700 cells per well, FIG. 10D 1000 cells per well microcancers to track growth and cell death post cell seeding and pre drug testing.

FIGS. 11A-11C. Real time live imaging of microcancer spheroid culture. FIG. 11A shows Imaging boat has a 16 mm circular cutout which is on an 18 mm diameter coverslip. The O ring (1.7 mm thick) surrounding the cover slip allows for height above the coverslip for hanging droplet formation. The boat is filled with oil for culture before inverting the chip (left). Images of setup in upright and upside-down positions (bottom images on left). Imaging setup on inverted microscope (right). The scale bar is 9.6 mm. FIGS. 11B-11C show 2D projected distance between peripheral cell clusters and reduction (%) in 2D projected distance between these peripheral cell clusters in FIG. 11B well 1 and 11C well 3 over 24 hours. These regions are shown in white circles and labeled in FIG. 3A.

FIGS. 12A-C show complete microcancer spheroid formation can be seen in each well. Each well has a side length of 300 um (for scale). FIG. 12B shows enlarged view of the microcancer in the red box shown in FIG. 12A (scale bar: 100 um) FIG. 12C, Cell cluster on the surface of the microcancer seen in FIG. 12B (scale bar: 40 um)

FIGS. 13A-B, Confocal images of 3D microcancers with LN 229 one day after cell seeding. Immunofluorescence detection of N-cadherin and DAPI nuclear staining. (scale bar: 20 um) FIG. 13C shows large tile of uniform LN 229 microcancers 3 days after cell seeding along with N-cadherin and DAPI staining, as well as human mitochondria staining (green). (scale bar: 200 um) FIG. 13D-13G show single well confocal images of 4 different microcancer spheroids showing cellular heterogeneity. (scale bar: 20 um)

FIGS. 14A-14F show confocal z-stack image of PDX microcancer three days after cell seeding. Distance between each z-stack slice is 10 um. Immunofluorescence detection of N-cadherin, DAPI nuclear staining and human mitochondria staining. (scale bar: 20 um)

FIGS. 15A-15E. On-chip LN229 drug testing. FIG. 15A, Timeline of drug testing experiments from cell seeding to analysis. FIGS. 15B-15E, Maximum projections of 12 well cultures for days 1-9 post cell seeding (initial cell concentration: 500 cells/well). On Day 3 post imaging, Dasatinib was loaded onto the chips. Final concentrations of drug added were FIG. 15B 1 uM, FIG. 15C 10 nM, FIG. 15D 1 nM, FIG. 15E 100 pM.

FIGS. 16A-16O. On-chip PDX drug testing. FIGS. 16A-16D Maximum projections of 12 well cultures for days 1-9 post cell seeding (initial cell concentration: 500 cells/well). On Day 3 post imaging, Dasatinib was loaded onto the chips. Final concentrations of drug added were FIG. 16A 1 uM, FIG. 16B 10 nM, FIG. 16C 1 nM, FIG. 16D 100 pM.

FIGS. 17A-17G, Line graphs track microcancer volume and cell death for 12 microcancer spheroids over 9 days post cell seeding. Drugs of concentrations FIG. 17A 10 uM, FIG. 17B 1 uM, FIG. 17C 100 nM, FIG. 17D 10 nM, FIG. 17E 1 nM FIG. 17F 100 pM FIG. 17G Negative control (only dye in media solution) were added on day 3 post cell seeding.

FIGS. 18A-18G, Line graphs track microcancer volume and cell death for 12 microcancer spheroids over 9 days post cell seeding. Drugs of concentrations FIG. 18A 10 uM, FIG. 18B 1 uM, FIG. 18C 100 nM, FIG. 18D 10 nM, FIG. 18E 1 nM FIG. 18F 100 pM FIG. 18G Negative control (no drugs in media and dye solution) were added on day 3 post cell seeding.

FIGS. 19A-19B, Shape formation in shapes Day 2 and Day 3 post cell seeding. Outer diameter (circle) or outer side length (square and triangle) of each shape channel is mentioned in top left corner above each image. Width (distance between internal post and outer boundary) of each shape is 200 um.

DETAILED DESCRIPTION OF THE INVENTION

Figure 1A:
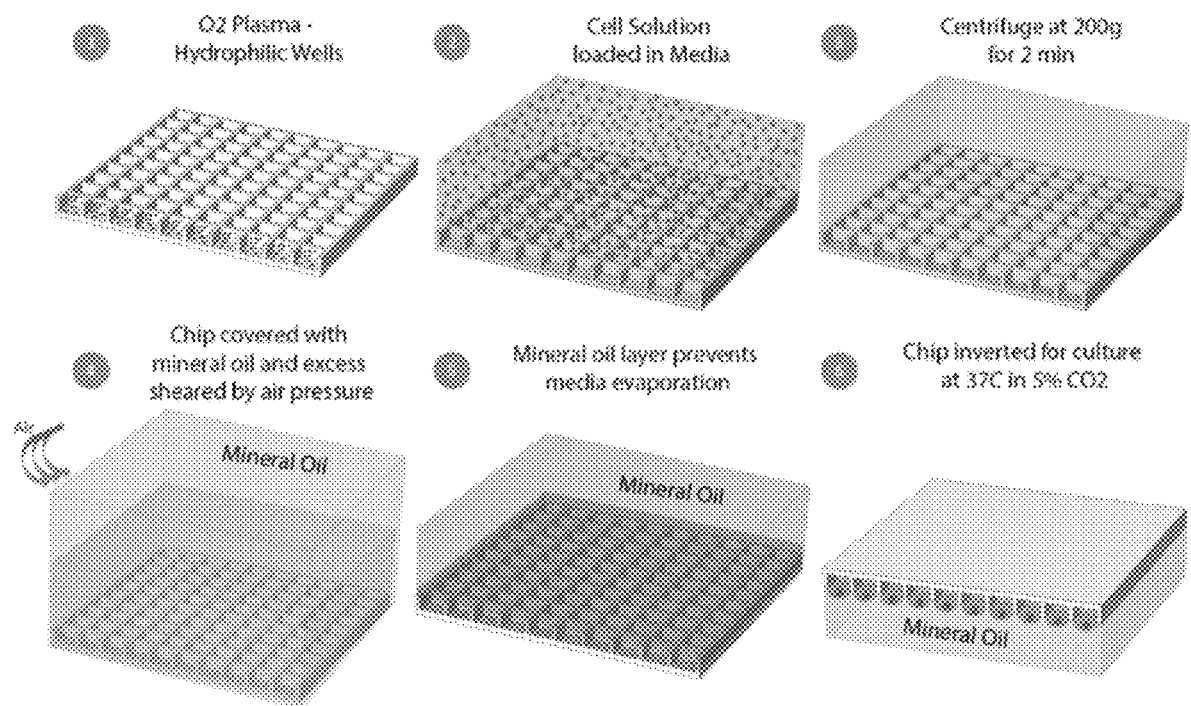
FIGS. 1A-F. On-chip cell culture schematic and spheroid characterization in a well size gradient chip.

In the following description, numerous specific details of the devices, device components and methods of the present invention are set forth in order to provide a thorough explanation of the precise nature of the invention. It will be apparent, however, to those of skill in the art that the invention can be practiced without these specific details.

"Array" refers to material or device having a number of wells, receiving chambers, void spaces or is otherwise configured to hold a number of liquid tissue samples. Arrays may have any number of wells and may be provided in various configurations including a grid, as described herein. Wells useful in the described arrays may have any geometric shape including pyramids, cones, and rounded bottom wells with circular, square or polygonal cross-sections. Arrays may include wells having more than one dimension (e.g. depth, width), volume and/or shape. Arrays may have greater than or equal to 10,000 individual wells, greater than or equal to 100,000 wells, or optionally, greater than or equal to 1,000,000 wells. A "microarray" refers to an array of microwells where at least one dimension of an individual microwell is less than 1 mm. Preferably, the microarray is formed from a plurality of microwells, including numbering between 100 and 1,000,000, and any subrange thereof, depending on the application of interest "Cells" refers to any biological sample containing cells. The cells of the biological sample may be substantially separated or may exist in the form of an aggregate of cells (e.g. spheroid) or a partial aggregate of cells. The cells may be ordered into a tissue, massed in a partially or wholly disordered tissue (e.g. cancerous tissue) or may be disordered.

"Liquid sample" is used broadly herein to refer to any sample that is capable of flowing under applied shear. Accordingly, the sample may originally be a non-fluid, such as a tissue or food, but that is suspended in a fluid solvent material, so that the original solid sample is a liquid sample. Alternatively, the sample may originate as a generally liquid sample. The sample may be a "biological sample" from a human, animal, a tissue, or a cell line. "Minimally processed" refers to the obtained liquid sample where no undue processing, purification, preservation has occurred. The methods and devices, of course, are compatible with processing, including a minimally processed harvest such as application of an anti-coagulant or fluid to achieve a desired fluid parameter (e.g., viscosity) to facilitate fluid spreading over the array, and surfaces thereof. "Unprocessed" refers to direct application of a fluid sample to the array, without intervening processing steps.

"Partition" refers to physically separating cell samples into individual microwells by means of settling, centrifugation, or an applied force such that unwanted cross-talk between individual wells, whether located adjacent or otherwise located, is minimized. Partition further removes excess fluid reagents, including by forcing air over the wells at a sufficient force to remove the excess liquids on the top of the wells, while the liquids in the wells remain in place, for instance due to a relatively higher capillary force or surface tension in the relatively small-dimensioned well.

The partitioning may utilize any of the methods, devices and components described in WO 2020/190871 to Bashir et al. titled "Spatially Mapped RNA Sequencing from Single Cells" (partitioning by "pixelization"); U.S. Pat. No. 10,724,089 titled "Spatial Molecular Analysis of Tissue" (partitioning by "pixelization"); WO 2019/071142 titled "Biomarker Detection from Fluid Samples").

To maintain robust partitioning, and maintain desired conditions within the microwells, an "immiscible layer" may cover the microwells. This may correspond to any of the inert covering fluids described in U.S. Pat. No. 10,724,089. "Immiscible layer" refers to a layer of fluid that will not substantially mix with another fluid. In the instant context, the immiscible fluid does not substantially mix with a fluid in the microwells in which the cell and tissue culture is positioned. Generally, the fluid in the microwells is characterized as a water-based culture media, similar to phosphate-buffered saline (PBS) or other culture media suitable for the cultured cells. The immiscible layer is, therefore, generally hydrophobic and tends to not mix with water, such as an oil-based fluid, including mineral oil. Of course, other fluids are compatible, so long as they do not substantively mix with the culture media. Such an immiscible fluid layer configuration provides a number of advantages, including the ability to access the microwells and attendant culture without disturbing other microwells or on-going cultures within the assay. For example, biologics, chemicals or other substances may be introduced to or through the immiscible layer, and the introduced substance allowed to settle under gravity by temporarily re-inverting the array or placed directly into one or more microwells, such as by micropipettes and the like.

As used herein, "substrate" refers to a material, layer or other structure having a surface, such as a receiving surface, supporting one or more components or devices including an array or microarray. Arrays may be embedded in substrates so that the array is formed within and made the same material as the substrate. Arrays embedded in substrate may be manufactured from a single piece of material. Substrates which may be useful in the methods and devices described herein include silicon, glasses, metals, insulators and/or dielectrics. Substrates may be composite materials. The substrate and/or supported array may also be referred herein as a chip.

"Cell and tissue culture" refers to a three-dimensional culture of living cells and/or tissue comprising living cells. The ability to control three-dimensional shape of in-vitro cultures provides a more realistic model for various in vivo tissues, which are inherently three-dimensional in nature. The cell and tissue culture is preferably a hanging drop culture, wherein no additional biological material, such as extracellular matrix, is required to control a three-dimensional shape parameter. Generally, the methods and devices are scaffold-free, other than variation in the physical shape of microwell and components thereof, and utilize gravity. In this manner, use of other biological materials or synthetic compounds is avoided, thereby further minimizing concerns around a treatment resulting in selective pressure of cellular phenotype and behavior. Accordingly, "hanging drop" refers to use of gravity to facilitate cell and tissue growth that would otherwise be constrained by the supporting microwell substrate in a flat two-dimensional geometry, including without other biological materials and compounds that could impact cell and tissue phenotype in culture. Instead, use of specially configured microwell shapes, including annular shapes, in combination with gravity provide reliable and robust control of a three-dimensional shape parameter, depending on the application of interest. Hanging drop culture is used interchangeably with "cell and tissue culture".

"Shape parameter" is used herein to refer to a measure of a cell and tissue shape. Accordingly, a "three-dimensional shape parameter" can refer to a volume, curvature, diameter, surface area, cross-sectional shape, linear distance, thickness and the like.

Provided herein is a modular and highly versatile microchip three-dimensional hanging-drop culture platform that allows high replicates and high throughput for drug screening, ability to engineer interconnections between different 3D cultured microtissues, compatibility with direct on-chip real-time or high-resolution confocal microscopy, and, geometric control of formed cell mass in 3D. Quantitative analysis of 3D culture based on initial cell density both for a conventional glioblastoma cell line and for PDX-derived microcancers is demonstrated. The ability to perform real time fluorescence observations is shown while tracking individual cultures directly on chip, and thus eliminates the need for any extractions of the microcancers. The capability of high-resolution scanning electron microscopy and confocal microscopy directly on chip using the demonstrated platform can allow for simplicity and ease of use for downstream analysis. The miniaturized hanging drop platform described here does not require specific matrices, specialized gels or nanoparticles, engineered scaffolds, or any form of synthetic surface coatings to form the tumor spheroids. This is especially useful when any of the above agents can be suspected of creating selective pressure and biasing tumor evolution during 3D culture. Growth media can be adapted for a variety of potential applications. In comparison to the classical hanging drop culture, cell aggregation into multicellular spheroids is significantly faster in the miniaturized platform (1 day vs 4 in the classical assay), likely an effect of the smaller well size that affects the diffusion of soluble factors and enhanced cell-cell adhesion.

The present nano-hanging drop culture model allows simultaneous testing of hundreds to thousands of 3D microcancer spheroids in real time where each microcancer appears to capture the salient characteristics of the tumor as evidenced by mate-pair sequencing and confocal analysis. The small size of the platform is also critical when available tumor tissue is limited, as is often the case in biopsies. Additionally, the platform also allows for sequential (staggered time point) drug testing. Therefore, this system makes it possible to rapidly (within days) examine the effect of multiple drugs in real time even in cases where small biopsies might be available.

Finally, also demonstrated for the first-time, is shape control of the cell mass using the present microchip hanging drop 3D culture platform. Since the present platform uses a microchip with etched channels, a chip was fabricated with circular, square, and triangular annular wells, which allowed the media droplet shape to conform to the shape of channel cavity due to capillary forces. It was shown that 3D shape formation can occur using the present single step loading and droplet formation technique by forming dense and continuous annular shapes ranging in sizes from a few hundred micrometers to several millimeters. The instant microchip hanging drop platform is compatible with co-culture of different cell types, allowing for self-organized tissue formation with salient in vivo like features. This simple, scalable, and customizable platform is particularly suited for a broad range of applications in drug discovery, regenerative medicine, stem cell research and biotechnology.

Figure 20A:
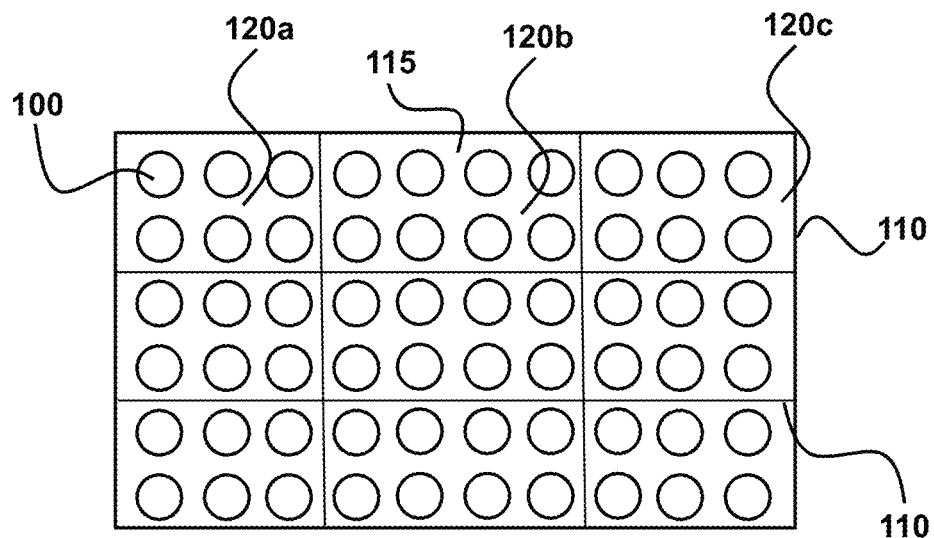
FIG. 20A is a top view of the array of microwells with a removable substrate that provides nine unique microreservoirs.
Figure 20B:
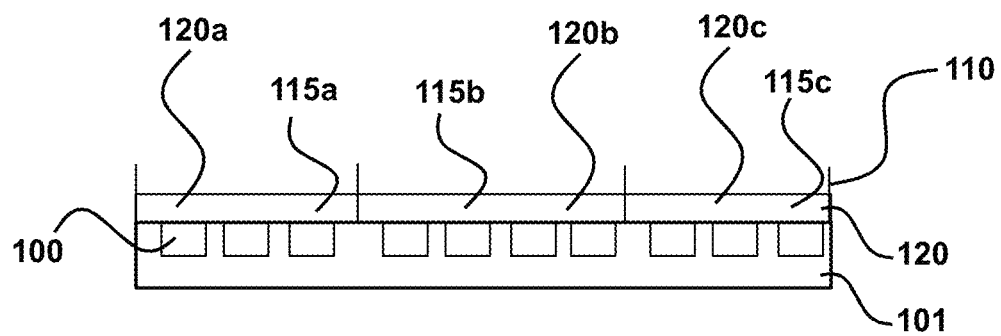
FIG. 20B is a side view cut-away of FIG. 20A, illustrating loading of unique cell mixtures.
Figure 20C:
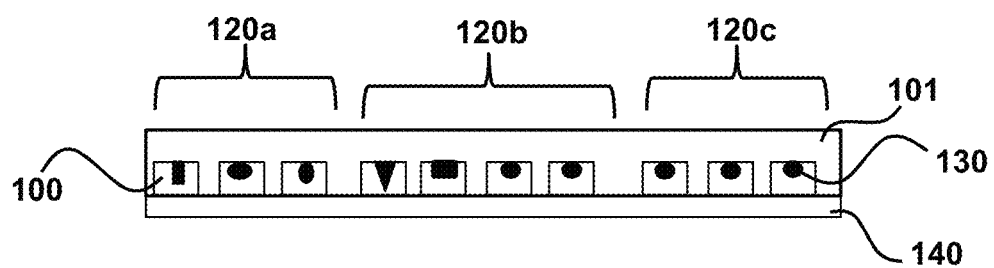
FIG. 20C illustrates inversion of the array with an associated immiscible layer to prevent leakage and evaporation of culture media from the microwells, including for an application where any of a number of unique cell and tissue seeding conditions, cell and tissue types and/or 3D cell culture shapes, under any of a variety of different growth conditions. The architecture is effectively "open" in that the cultures are visually, chemically and physically acceptable, with only an immiscible fluid layer separating the culture from the surrounding environment.

A schematic overview of the system is provided in FIGS. 20A-20C and a corresponding method summarized in FIG. 1A. Microwells 100 are formed in a substrate 101, such as a silicon, glass, plastic or oxide substrate. A removable reservoir 110 is positioned over the top surface of the microwells and a mixture comprising cells 120 (e.g., unique mixtures illustrated by 120a 120b 120c) loaded. The removable reservoir 110 can be configured to provide any number of microreservoirs 115, also illustrated as 115a 115b 115c in FIG. 20B. This is particularly useful, as the number of unique cell mixtures can vary from 1 (e.g., removable reservoir corresponds to the outer perimeter of the microwell array) up to the total number of microwells (e.g., removable reservoir has a number of microreservoirs that is equal to the total number of microwells with the microreservoirs aligned with the underlying microwells). This combination provides extraordinary flexibility for high-throughput, including a number of unique cell mixture loadings, repeats, and different geometries associated with each microwell 100. In FIG. 20A, for simplicity, sixty microwells 100 and nine microreservoirs 115 are illustrated.

FIGS. 20A and 20B show the initial steps, with a top view of the array of microwells and a side view to better illustrate portions of the removable reservoir with different cell mixtures and/or treatments 120a 120b 120c provided therein. FIG. 20C illustrates the end culture-process, where the cell mixtures 120a 120b 120c have been cultured into cells and/or tissue 130 covered by immiscible layer 140 and inverted. The cells and tissue are illustrated as having different sizes and/or shapes to emphasizes the flexibility of the instant platform. The combination of the removable reservoir shape, ability to precisely control 3D culture geometry, open architecture, and/or high-throughput nature provides a number of important advantages over conventional systems, as further described herein.

Example 1: Hang Drop Culture Platform

Figure 1B:
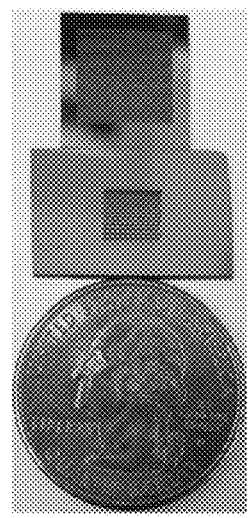

Several microchip designs are fabricated based on a silicon substrate. The microchips contain an array of silicon microwells of varying dimensions etched to a depth of 120 µm. The silicon surface was oxidized after the formation of the wells. FIG. 1A shows the platform design and schematic of on-chip cell seeding protocol. Panel 2, for clarity, does not illustrate the removable reservoir used to reliably position the cell solution loaded in media over the microwells. The entire chip is less than the size of a quarter and FIG. 1B shows two chip designs, one with an array of 900 microwells with a constant well size of 300 µm (side length of well) and the other with a well size gradient in which the well side lengths were varied from 100 to 500 µm. This system is readily scaled to a larger size and a higher number of individual wells. The spacing between each well was maintained at 20 µm. Each individual well in this array will downstream act as an isolated incubation chamber for 3D hanging drop cell culture. A detachable Polydimethylsiloxane (PDMS) well (or well array) (referred herein as a "removable reservoir") (no shown) is assembled on top of the silicon chip to select a subset of the silicon wells to customize the number of microcancers required. The temporary adhesion between the PDMS well and the chip surface forms a removable reservoir over the chip where the cell solution can be loaded and centrifuged. The cell seeding protocol began by first making the surface of the chips hydrophilic by exposing to oxygen plasma for 3 minutes at 300 watts (FIG. 1A(1)). This step serves two goals. First, the hydrophilicity helps in homogenous cell seeding by allowing easy access of media and cell solution inside the wells, and second, it makes the chip surface and environment sterile for downstream culture. After making the chip hydrophilic, the cell solution is loaded in the PDMS reservoir and the cells centrifuged at 200 g for 2 minutes. The centrifugation step brings down the cells into the underlying wells and loads the entire array in a single step (FIG. 1A(2-3)). Once the cell loading is complete, the PDMS reservoir is removed and the individual micro-wells are partitioned using mineral oil and shear force from air or oil. (FIG. 1A(4)). See also Ganguli et al. "Pixelated spatial gene expression analysis from tissue." Nat. Commun. 9, 202 (2018). This step removes well-well connections and forms individual droplets in wells. Finally, the chip inverted in mineral oil in cell culture chamber to create inverted hanging drops, thus increasing cell-cell interactions, and resulting in the tumor spheroid formation (FIG. 1A(5-6)). The volume of each well is kept constant by the mineral oil layer which serves as an evaporation barrier allowing culture for an extended period. Importantly, no additional surface coatings or gel formulations are needed which might put selective pressure on tumor evolution. Accordingly, any of the methods provided herein may be characterized as being a selective-free pressure method.

Example 2—Cell and Tissue Culture Size Control

Figure 1C:
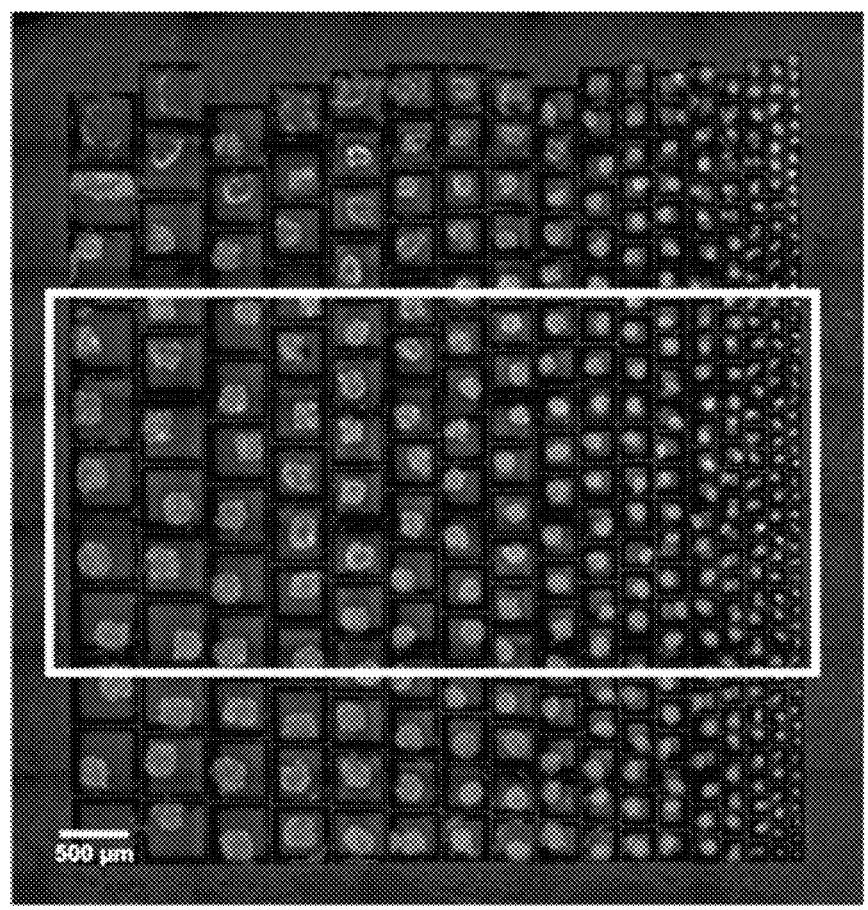
Figure 1D:
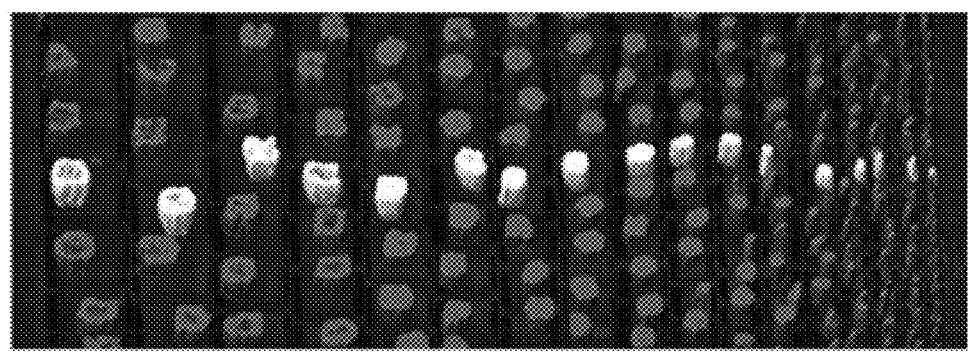
Figure 1E:
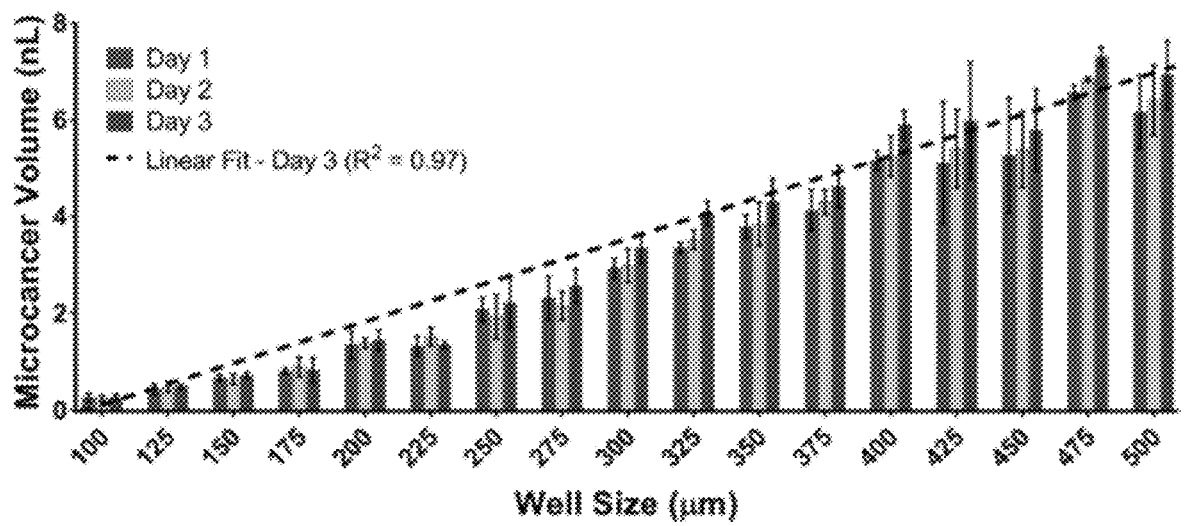
Figure 1F:
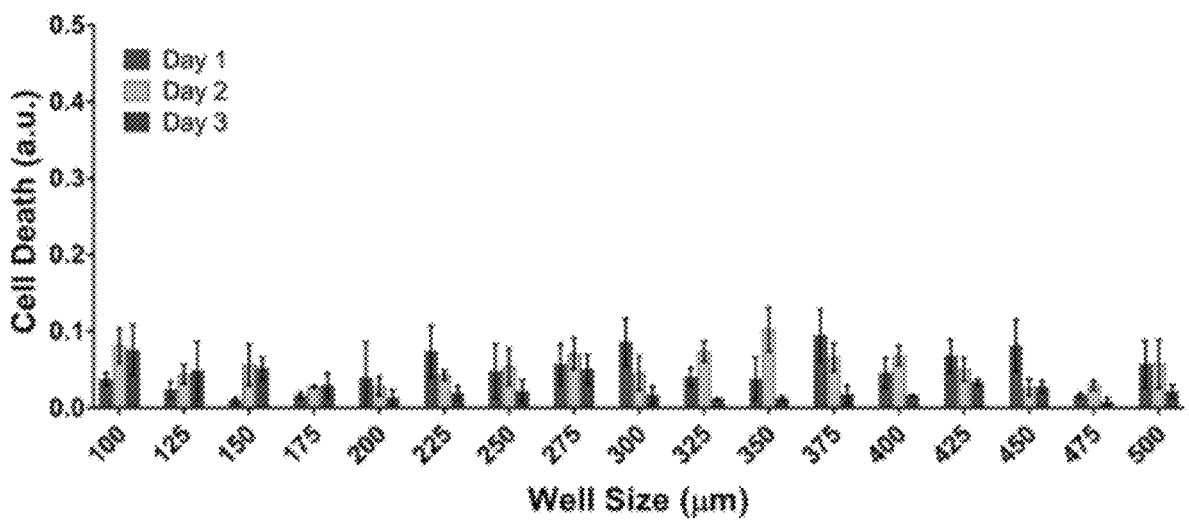

To evaluate the platform's ability to form and culture microcancer spheroids on chip of different sizes, LN229 cells were first seeded on the well size gradient chip and examined the survival profiles of the formed microcancers over time. A real time imaging compatible cell death indicator green dye (Celltox, Promega) and a cell membrane staining red dye (PKH, Sigma Aldrich) were added to the media to quantify cell death in the microcancer tumor volume with time. Tile and z stack imaging was performed for each day of culture to volumetrically map the green and red volumes within a micro-well. Volumetric mapping of the green and red dyes was performed on Imaris software, and final individual well tracking was performed using MATLAB. The cell death for each microcancer was normalized to its own culture volume to account for well-to-well variations in cell numbers. FIG. 1C shows a fluorescence microscope image of a high throughput culture of LN229 human glioblastoma microcancers after 1 day of culture post cell seeding on the well size gradient chip. Loading a solution of cell density at 1.87 million cells/ml resulted in a range of microcancer sizes from 7.6 nL for 500 um wells to 0.36 nL for 100 um wells. FIG. 1D shows the volumetric mapping of spheroids seen in the white box in 1c. One of each microcancer size has been highlighted. Three microcancers of each size were analysed for microcancer volume and cell death. In FIG. 1E, a linear relationship is seen of well size to microcancer volume with an r-squared value of 0.97. Over three days of culture, the 100 um spheroids (smallest size) remain relatively constant in size with an average volume increase of about 1.5%. In contrast, the 500 μm spheroids show an average volume increase of 12.5% over 3 days of culture. However, as seen in FIG. 1F, cell death remains below 13% over the three days of culture. In current 3D cultures, diversity in spheroid sizes and morphology leads to challenges in creating standard culture and assay protocols as well as in analysing data. Being able to control and test a range of spheroid sizes in a high throughput manner will be useful in cancer drug screening and other biological applications. Microcancer size can also be controlled in the platform for a constant well size by varying the seeding cell density. The box and whiskers plot (n=12) of the microcancer volume and cell death for varying cell numbers per well over 3 days of culture for LN229 human glioblastoma cells cultured in 300 um well array is shown in FIGS. 8A-8F. It was found that 300 cells per well did not seem to aggregate as well as the other higher cell numbers per well, evidenced by a higher range of volumes on day 1. Note that for 1000 cells per well, the microcancer spheroid volume is ~4 nL on day 1 which is still less than 50% of the micro-well volume (10.8 nL), leaving additional volume for further cell growth.

To demonstrate that the present platform and fabrication process allows easy integration of new design elements on the chip, a chip design is shown in FIGS. 7A-7C where individual hanging drop compartments are interconnected by channels, also referred herein as a microwell interconnect 710. FIGS. 7A-7B show the optical and microscope image of the chip. Reservoirs that can be used for media exchange are designed near the chip borders and connects to the corner wells of the chip. Each individual well on this array is connected to its neighbour on all sides through small fluidic channels 710, such as between 5 μm-50 μm wide, including 10 μm wide. FIG. 7C shows LN229 human glioblastoma spheroids after 1 day of culture on chip post cell seeding. It is important to note that in the exemplified system, the interconnections between wells, the inter-well spacing, and the length and width of the connecting fluidic channels can be tailored to suit the application. This feature, with its elegant fabrication and robust operation, facilitates studies of complex multi-tissue studies and metabolic inter-tissue communications.

Figure 2E:
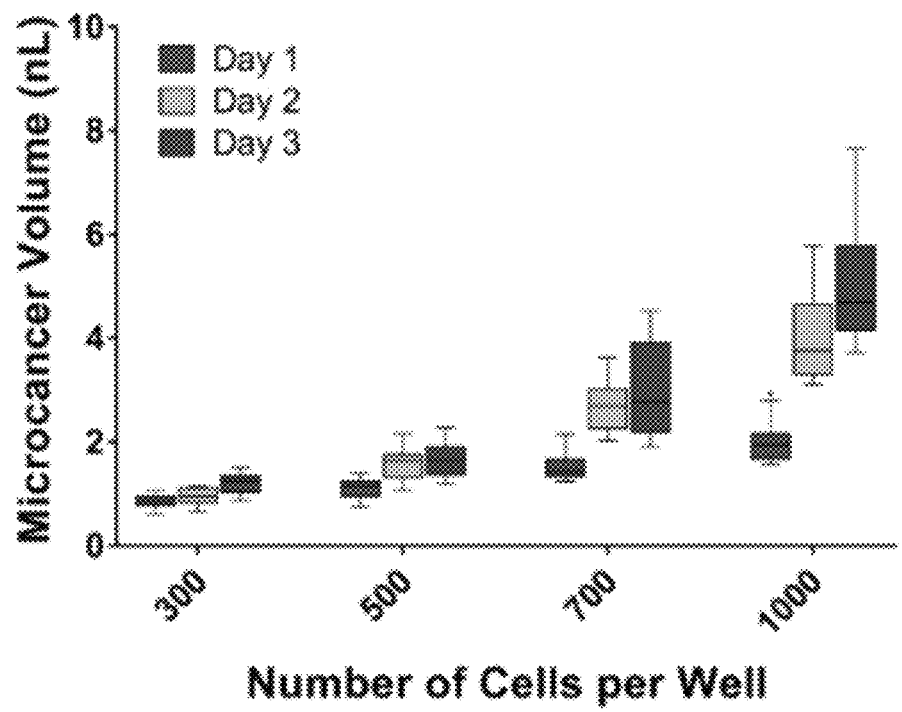
Figure 2F:
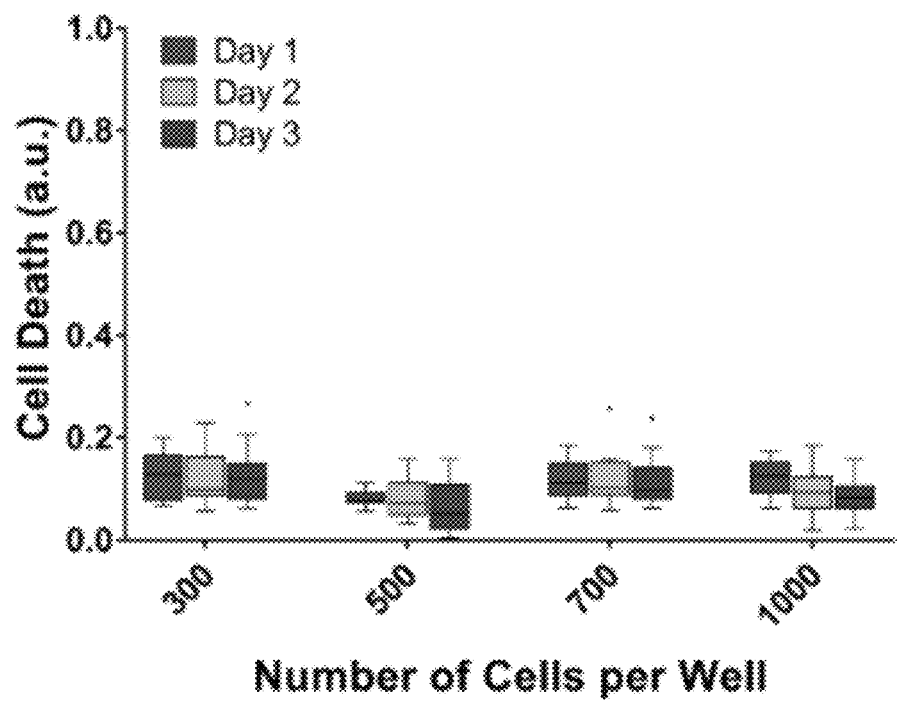

Next, to demonstrate the ability to culture primary tumor cells on the present platform, 300 μm well array was loaded with cells harvested from GBM8 patient-derived xenografts (PDX) implanted in mouse brain (FIGS. 2A-2D). The harvest cells from the xenograft represented the cellular diversity of the PDX brain tumor. FIGS. 2E-2F shows the box and whiskers plot (n=12) of GBM8 microcancer volume and cell death for varying PDX cell numbers cultured on chip for 3 days. Interestingly, for PDX cells, the 300 cells per well scenario formed dense spheroids as opposed to their LN229 cell line counterpart. Also, the PDX spheroids had lower day 1 volumes for 700 (~1.5 nL) and 1000 cells (~2 nL) per well compared to their LN229 cell line counterparts (3.5 nL and 3.75 nL, respectively). These differences likely reflect differential expression of adhesion receptors and increased compaction of cells in the PDX tumor. It is important to note that the present technique can optically track individual wells for changes in cell death or microcancer volume over time and can automatically normalize for any variations in cell loading process. FIGS. 9A-9D. and FIGS. 10A-10D show individual traces of volume and cell death versus time for LN229 and PDX microcancer spheroids, respectively.

Accordingly, any of the methods described herein may further comprise the steps of optically tracking individual wells to determine change in cell death or microcancer volume as a function of time. Generally, increasing volume indicates cell proliferation, whereas smaller or decreased volume indicates decreased cell proliferation and, in certain circumstances, increased cell death. Optionally, the method may further comprise automatically normalizing for variations in the initial cell seeding, where some of the differences in cell number over time may be attributed to different number of cells initially introduced to the microwell.

Example 3—Harvesting 3D Cultures from Chip for Genomic Analysis

The present system is in an open format with an immiscible layer of fluid over the array. The system, therefore, is compatible with harvesting the formed 3D cultures from the chip. To do this, the chip is first submerged in media (e.g., on the order of 1 mL) to remove the residual oil layer from the top of the array. Then, the 3D cultures are removed such as by pipetting and aspirating the volume from the chip. In this manner, as desired, any cell and tissue culture can be removed without disturbing any of the other cell and tissue culture contained in other microwells. Of course, the system provided herein is also advantageously configured to obtain a number of real-time parameters to characterize cell and tissue parameters (e.g., growth, response to drug, etc.) without having to remove the cell and tissue from the microwell.

Figure 2G:
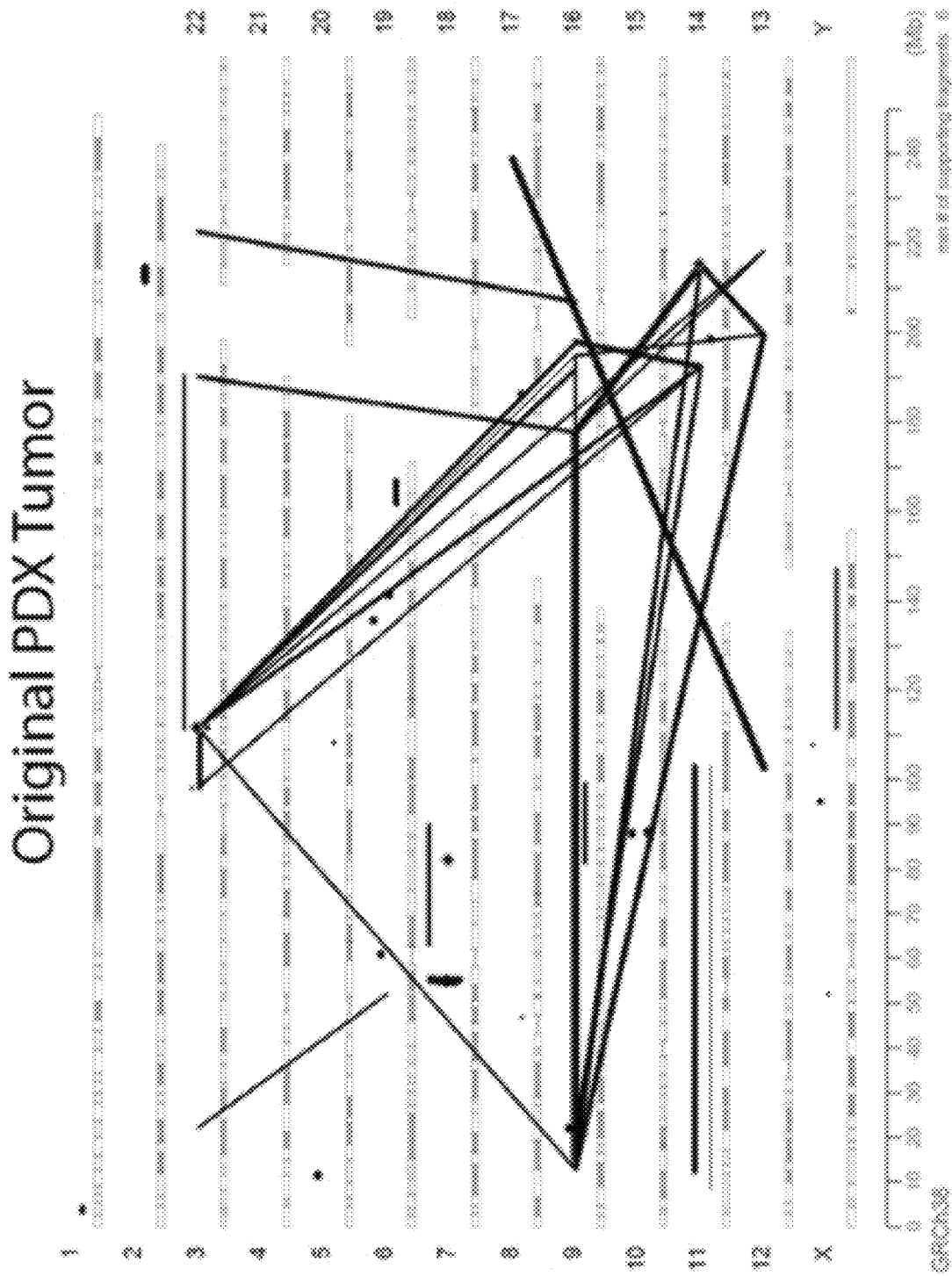
Figure 2H:
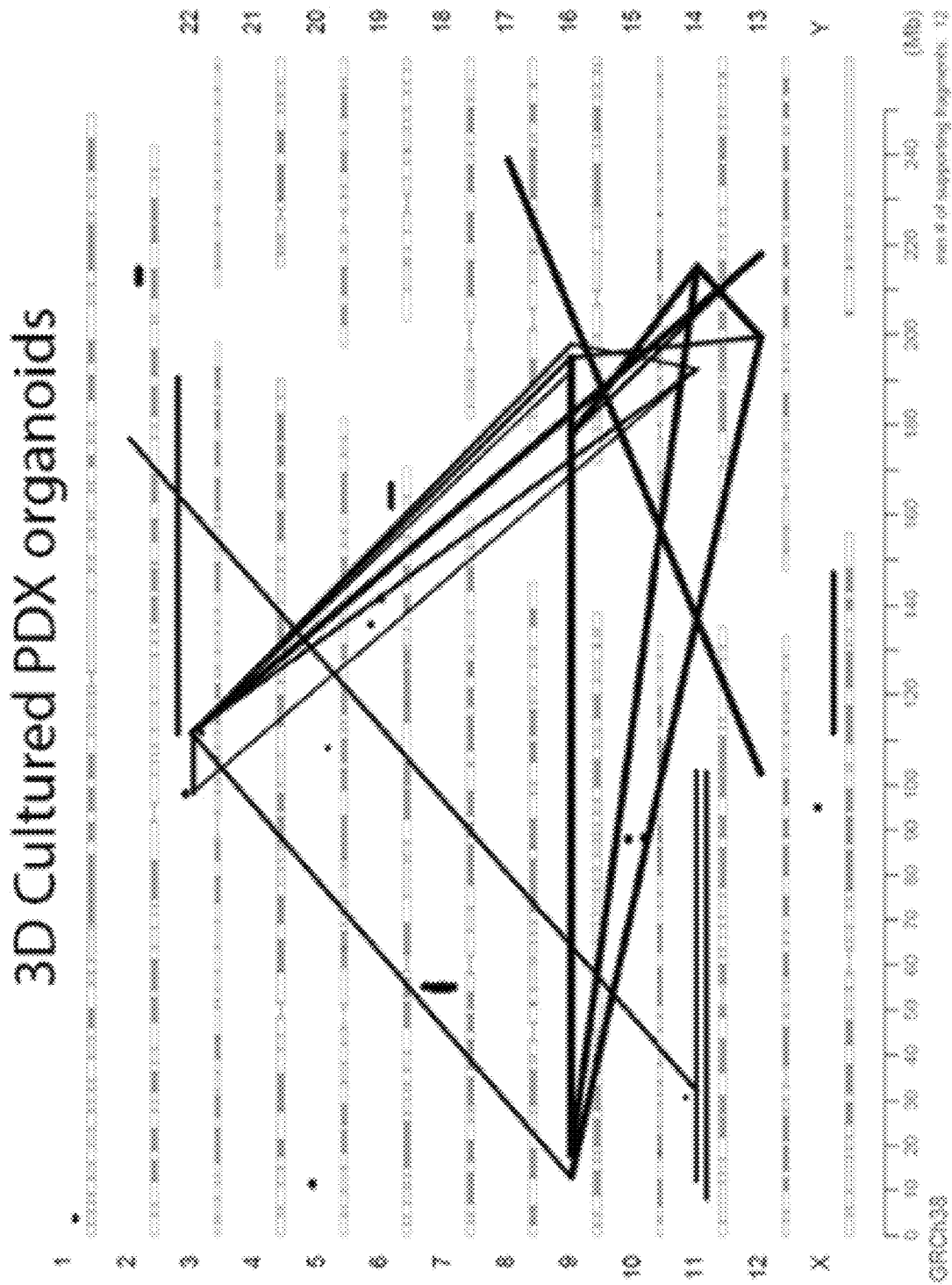
Figure 2I:
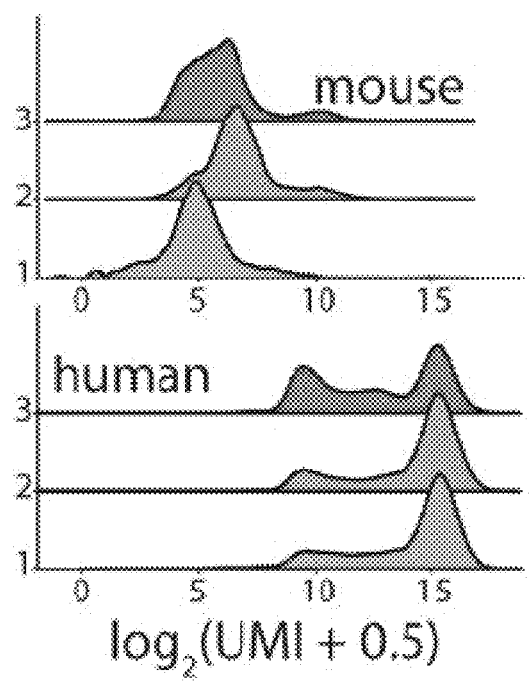
Figure 2J:
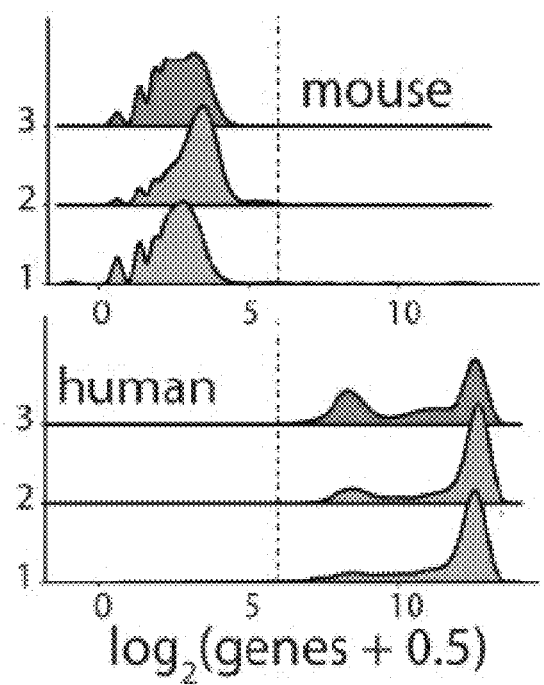
Figure 2K:
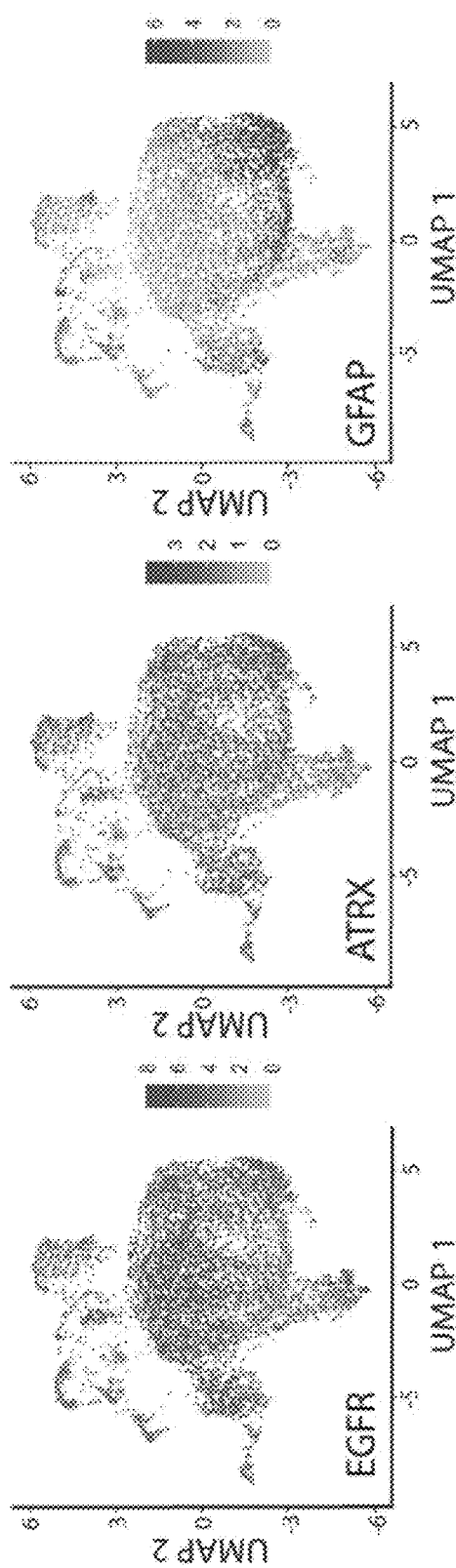
Figure 2L:
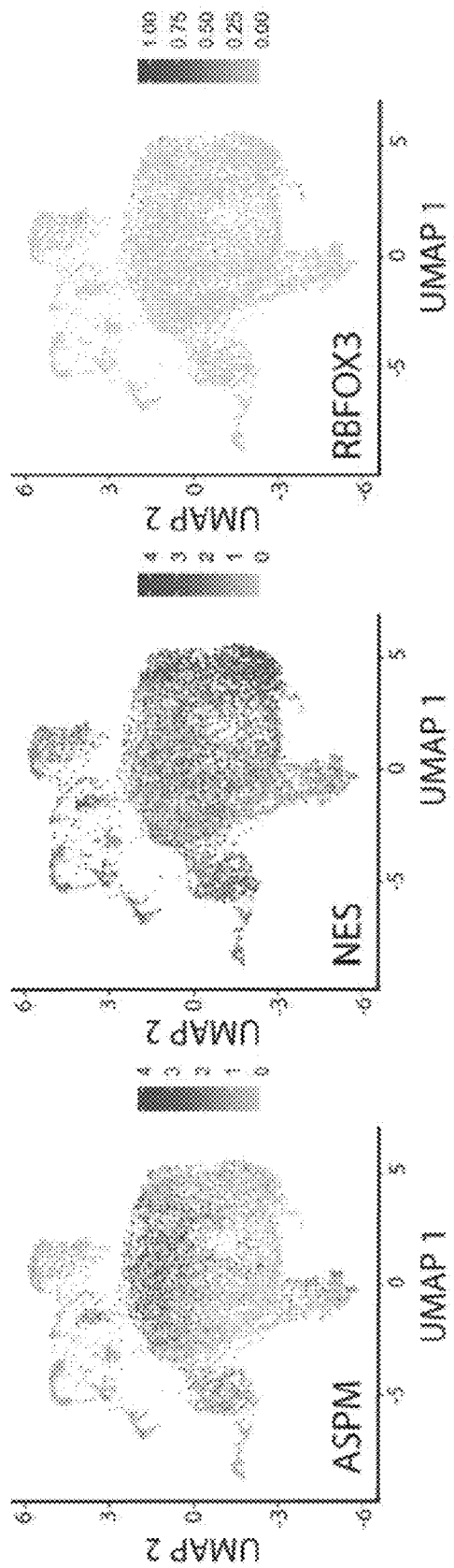

Example 4—Mate Pair Sequencing Demonstrates High Degree of Relatedness Between the PDX and 3D Cultures To further explore the biological attributes afforded by the present platform and to show that the present culture platform does not bias tumor evolution by exerting selective pressure on the cells, PDX microcancers were harvested after 3 days of culture on chip, and genomic analysis was performed on these microcancers and the PDX source for comparison. FIGS. 2G-2H shows the genome plots of the PDX tumor and a merge of 3 experiments from PDX tumor grown in 3D from the platform. Each line on the plot represents a Chromosomal Rearrangement (CR) event supported by at least 6 sequencing fragments chosen as threshold. The plots show high degree of similarity. Significantly, over 60% (38 of 63) of all CRs were shared between the two samples. Furthermore, for all other CR events that appeared to be unique to one sample, sequencing fragments were found corresponding to the same event in the other sample but at lower than threshold levels. Therefore, there was a complete overlap in CR events between the two samples, suggesting high degree of relatedness between the PDX and the 3D cultures.

Example 5—On Chip Real-Time Cell Imaging of Microcancer Formation

Figure 3A:
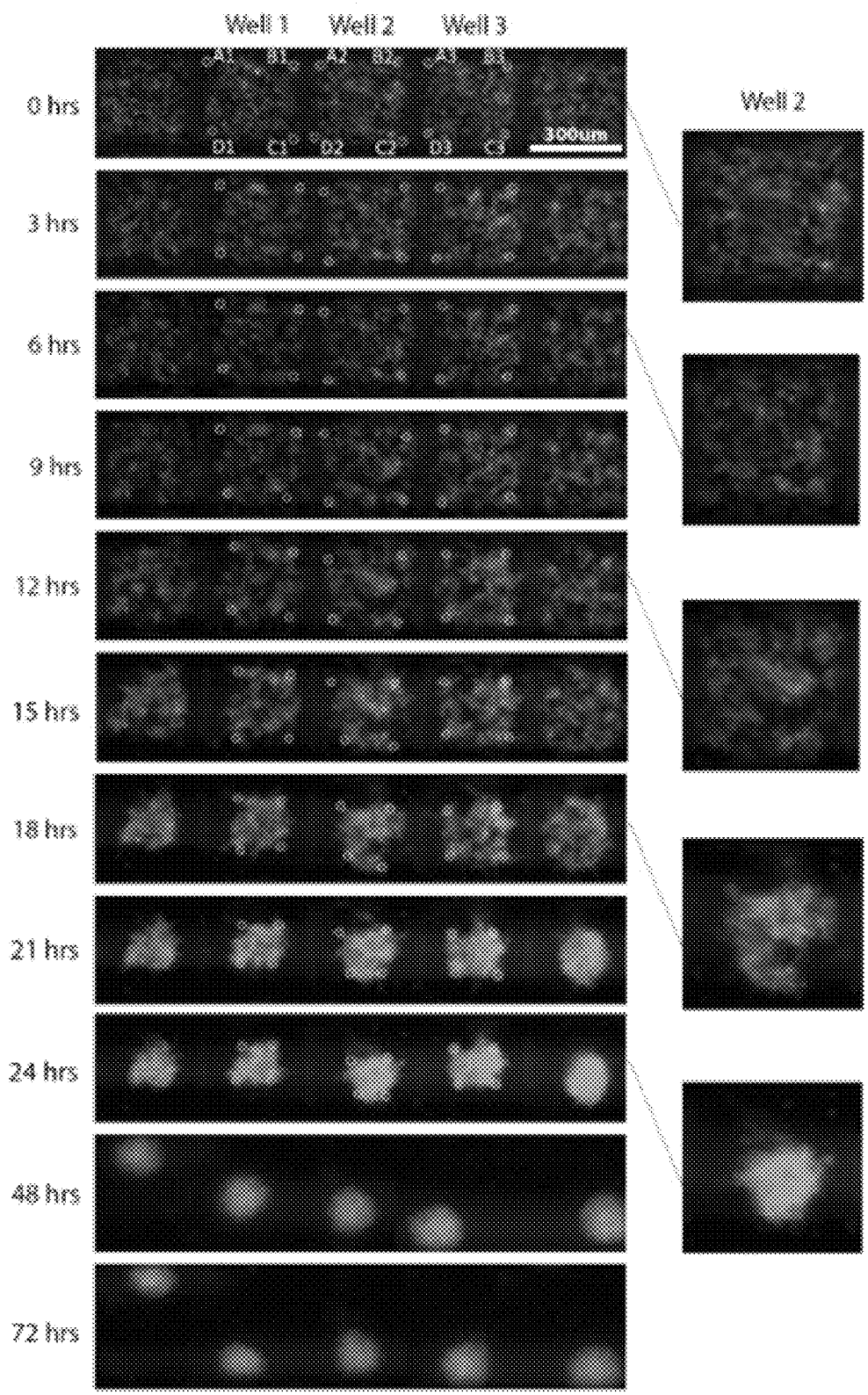
Figure 3B:
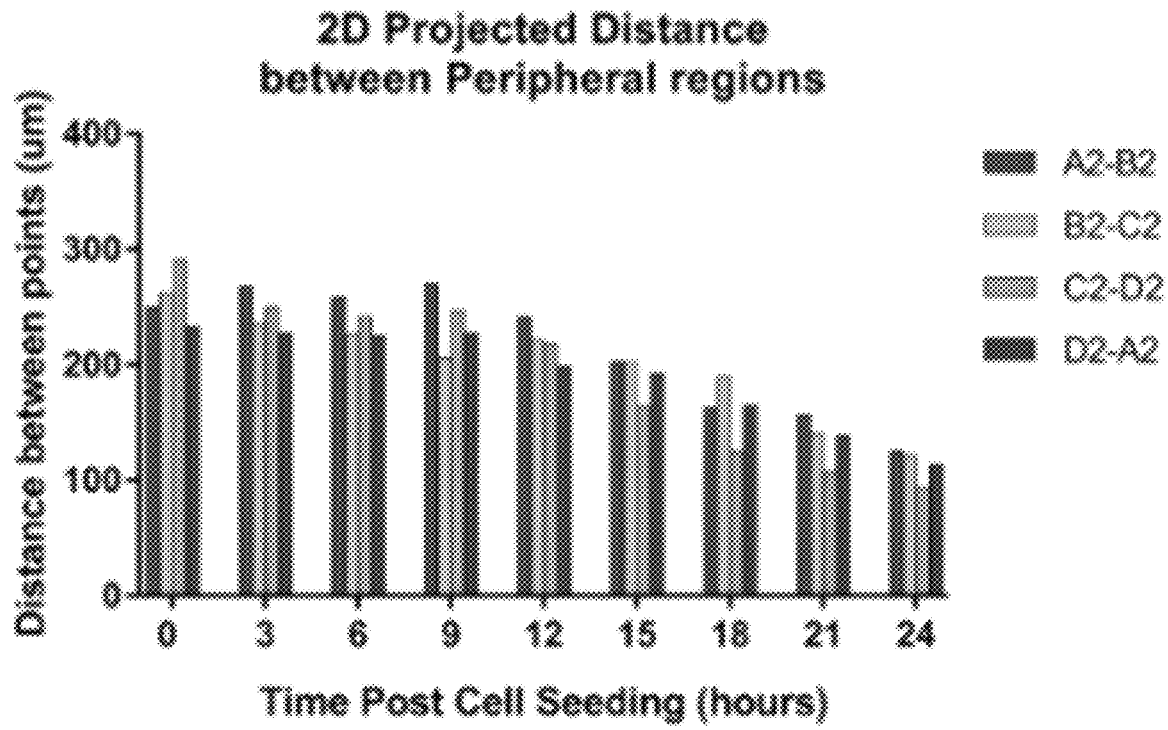
Figure 3C:
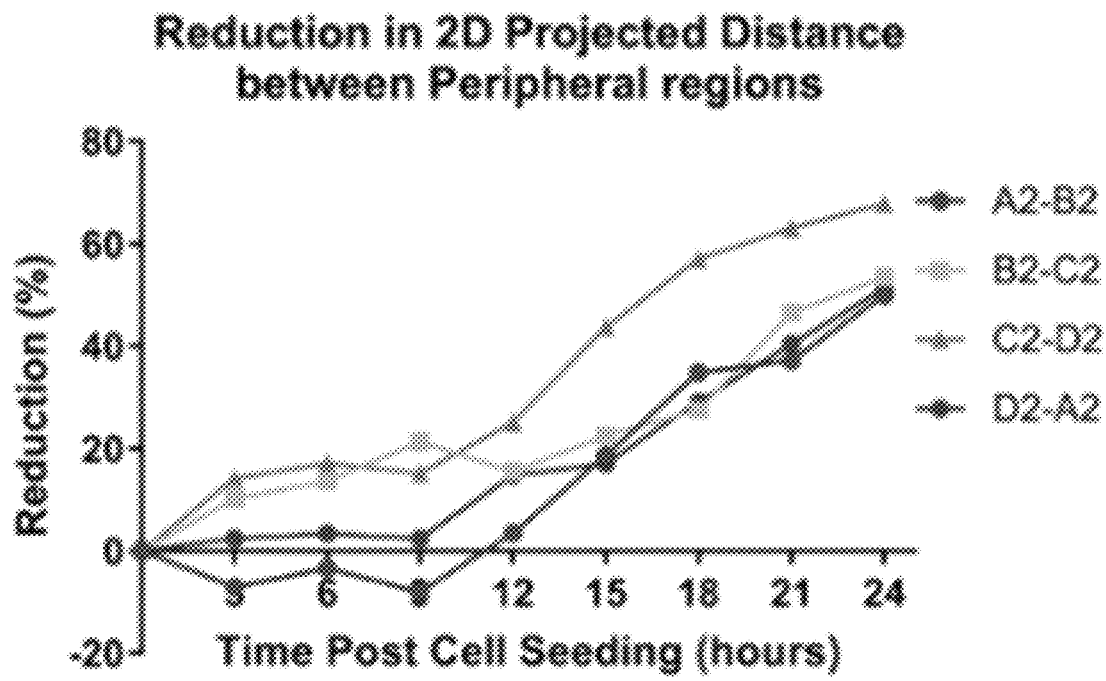

To observe the microcancer formation in real time, automated live-cell fluorescence microscopy was performed on a Zeiss Axio Observer Z1 inverted microscope. FIG. 3A provides time lapsed images over 72 hours from live cell imaging set up shown in FIG. 11A. 4 cell clusters were tracked initially located at the well-periphery for 3 wells and plotted the change in the 2D projected distance between these regions over time (FIGS. 3B-3D, FIGS. 11B-11C). The rate of aggregation of cells was slower for the first 9 hours post seeding as seen in FIG. 3D possibly because of the time it takes to re-express adhesion molecules following trypsinization, or for the secretion of soluble factors that enhance cell-cell adhesion. Separate small local cell aggregates form initially at different locations within a well, followed by joining of these aggregates over time, and finally movement of these aggregates towards the centre of the well to form the final microcancer spheroid. Once the formation was complete in 24 hours, the microcancers maintained their shape and integrity for the next 48 hours of the experiment. This imaging capability further extends the applications of the present platform to a range of studies of spheroid, organoid, and acini formation in microenvironments and various tissue-on-a-chip applications.

Example 6—Morphological and Molecular Characterization

Figure 3F:
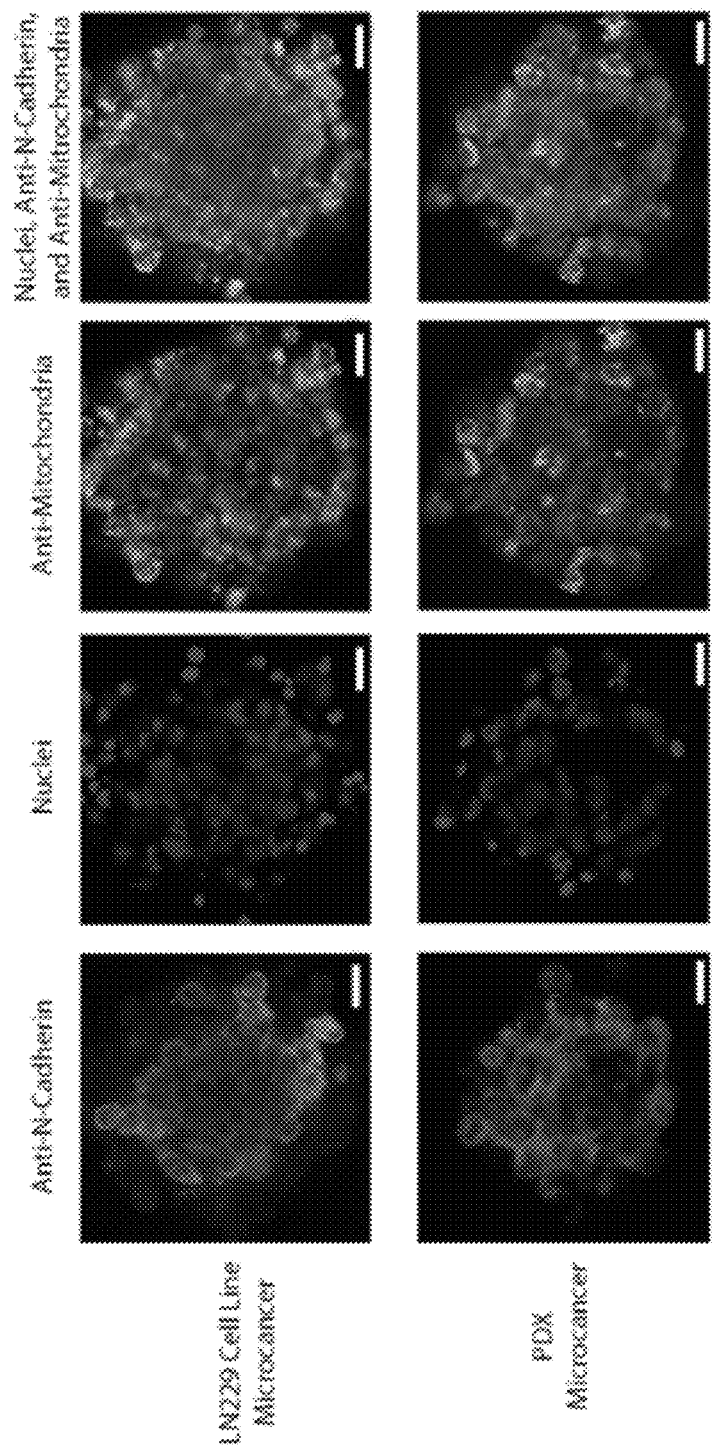
Figure 3G:
Figure 12A:
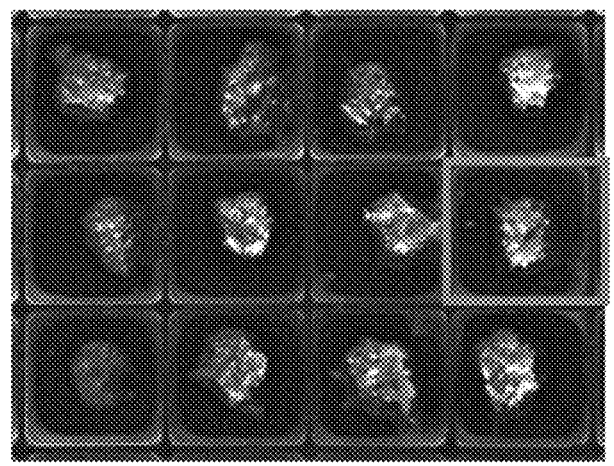
FIGS. 12A-12C. SEM characterization of microcancer formation.
Figure 12B:
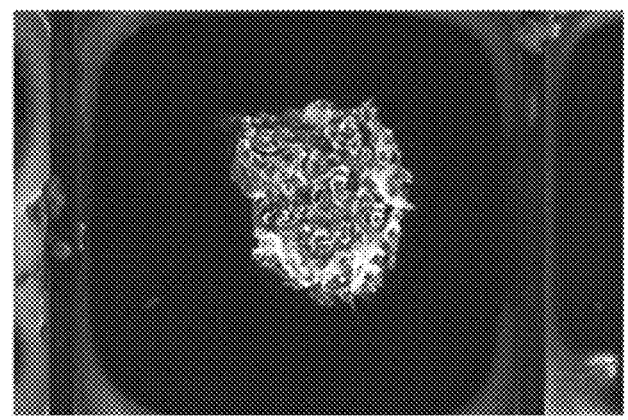
Figure 12C:
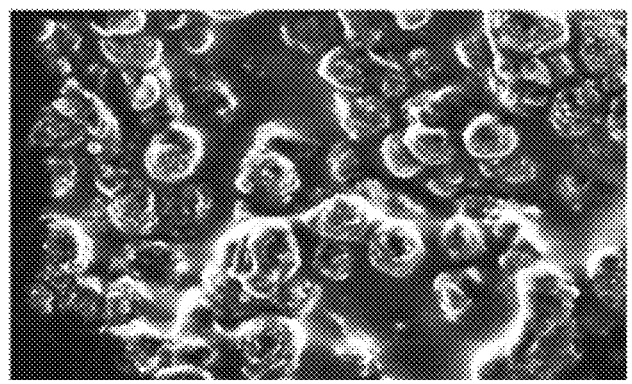
Figure 13A:
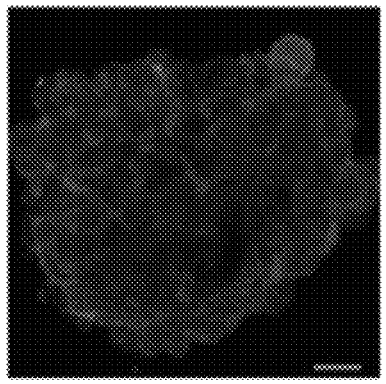
FIGS. 13A-13G. Confocal Images of microcancers.
Figure 13B:
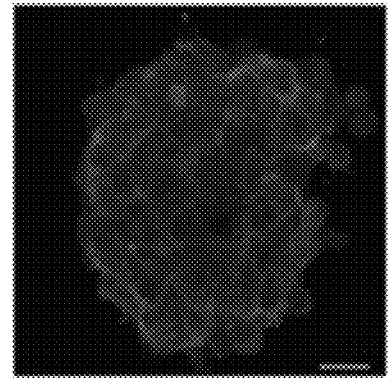
Figure 13C:
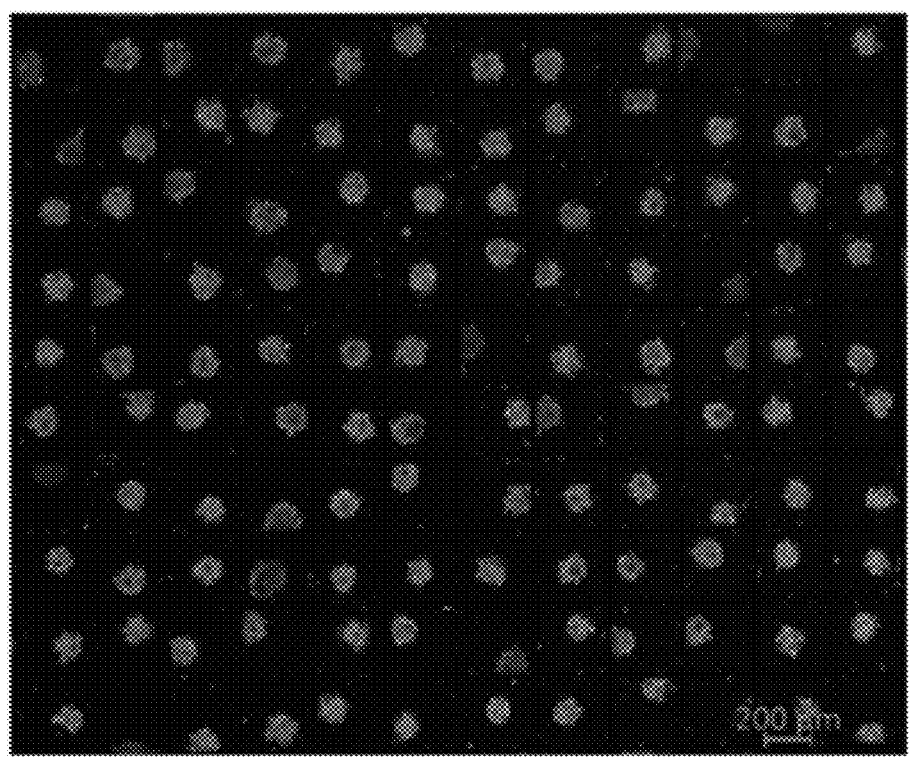
Figure 13D:
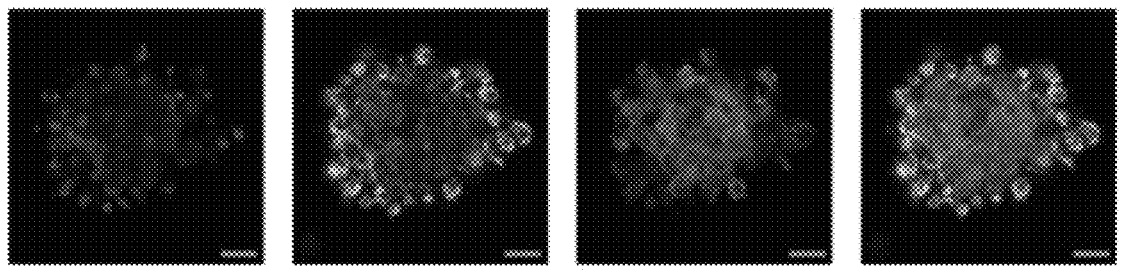
Figure 13E:
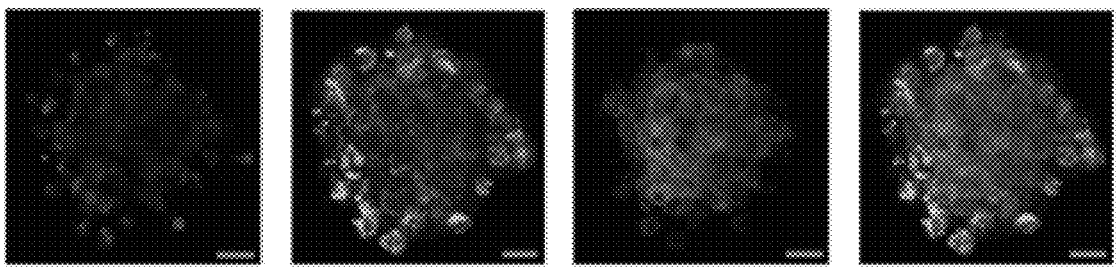
Figure 13F:
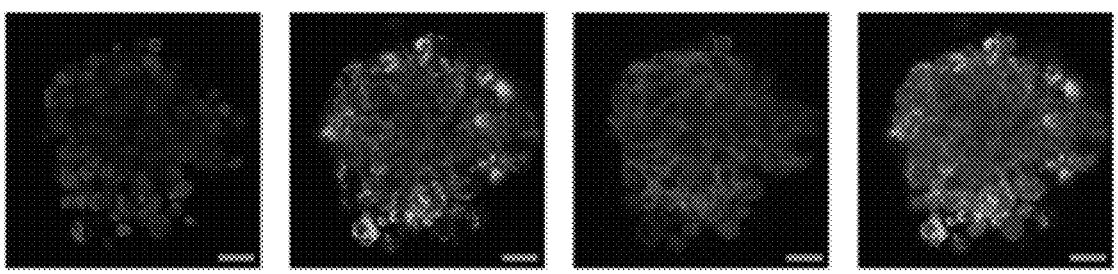
Figure 13G:
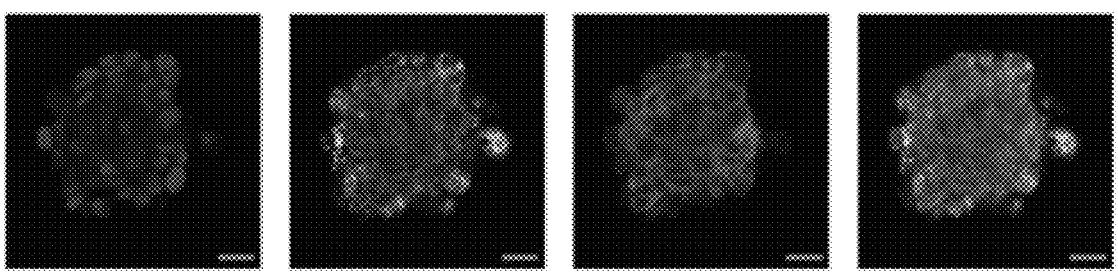
Figure 14A:
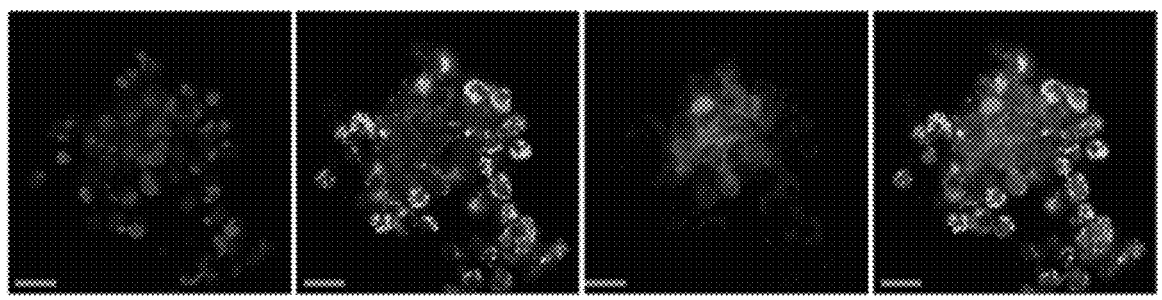
FIGS. 14A-14F. Confocal Z-Stack Images of PDX microcancer spheroid.
Figure 14B:
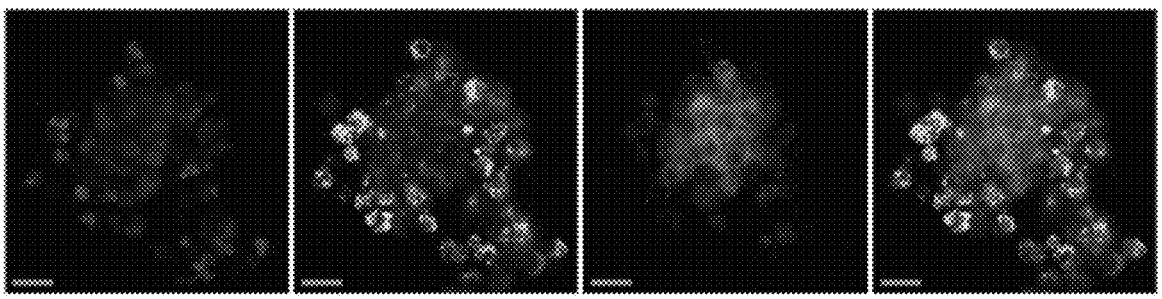
Figure 14C:
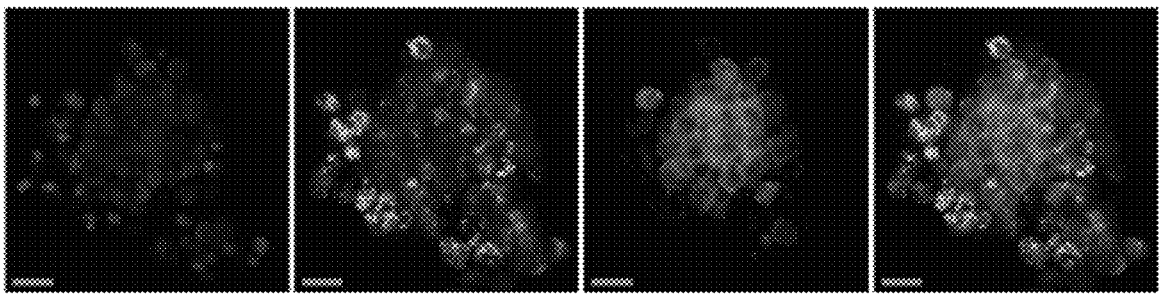
Figure 14D:
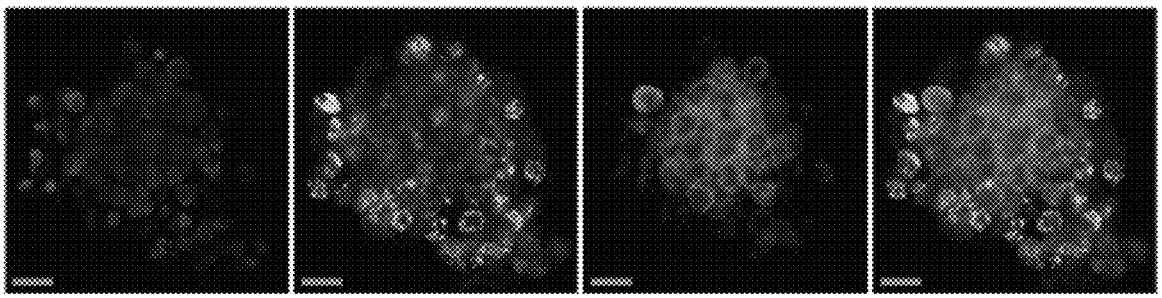
Figure 14E:
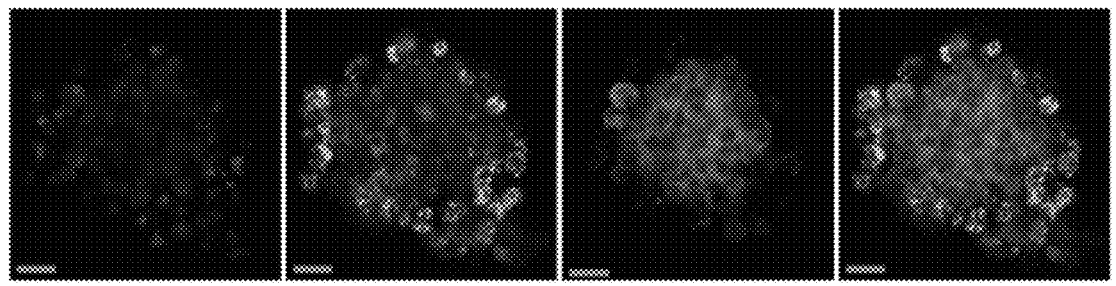
Figure 14F:
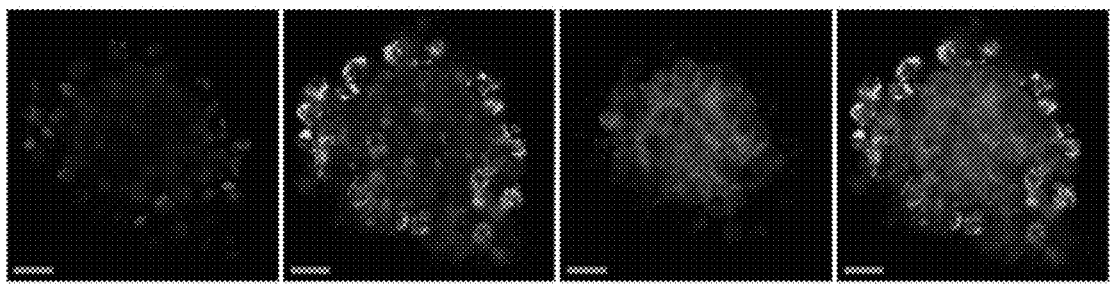

Morphological analysis is performed of these three-dimensional spheroids using scanning electron microscopy to reveal the architectural integrity of these structures (FIGS. 12A-12C). As previously discussed, the samples can be directly fixed and imaged on chip without the need for any extraction. The spheroids formed in the present platform were characterized, both structurally and molecularly, to show their similarity with in-vivo tumor characteristics and hence propose their utility as in-vitro cancer models for drug screening in Glioblastoma. Human glioblastoma cell (LN229) and PDX microcancers were cultured on chip for 3 days, and then imaged using a high-resolution confocal microscope directly on chip. The expression of N-cadherin was evaluated, a transmembrane protein that mediates cell-cell contact through homotypic cell adhesion. Consistent with reported cellular localization in GBM, other 3D cultures and xenograft models, N-cadherin expression was observed both in the membrane at areas of cell-cell contact, and also in the cytoplasm (FIGS. 3E-3G). This is in contrast with two-dimensional cultures in which N-Cadherin expression was found in the cytoplasm and the nucleus but absent from membrane. FIGS. 13A-13B show confocal images of LN229 tumor spheroids with high N-Cadherin expression at the cell junctions and cytoplasm within 1 day of culture on-chip. FIGS. 13C-13G show a large confocal tile of an array of tumor spheroids on chip and high-resolution confocal analysis of individual tumor spheroids and FIGS. 14A-14F show a split-view of confocal z-stack of a PDX microcancer. These results demonstrate the versatility of the present platform to perform high-throughput and high-resolution protein expression analysis to elucidate and study heterogeneity in the 3D cultures directly on chip.

The high-resolution confocal analysis presented above was performed directly on chip without the need to extract the 3D cultures. This feature allows users to select and analyse specific microcancers based on specific criteria and to track individual microcancers over the course of analysis. This is important when heterogeneity within the microcancers originated from the same patient-derived tumor cell suspension could be expected due to tumor heterogeneity, or due to sub-sampling of different cell populations. The tracking is not possible in conventional techniques, which require users to extract the 3D cultures in bulk and analyse them downstream. This direct on chip imaging, analysis and characterization can be even more important for primary cell cultures, studies on acini, and lumen formation, etc., where 3D structures can be very fragile and break upon shear stress from pipetting and handling. In summary, direct compatibility of the present platform was shown with several forms of high-resolution optical characterization techniques.

Example 7—Drug Testing Directly on Chip

The platform provided herein is compatible with drug testing directly on-chip, as demonstrated by taking real time measurements of response to drugs. In contrast, conventional hanging drop methods used to extract the formed tumor spheroids and then performing an end-point only analysis in a separate well plate. Dasatinib was selected for drug testing, and introduced after 3 days of culture in the chip. Dasatinib is a tyrosine kinase inhibitor which has previously been shown to reduce cell viability in several conventional and PDX GBM cell lines, including LN229. One process for introducing the drugs on chip is as follows.

Figure 15A:
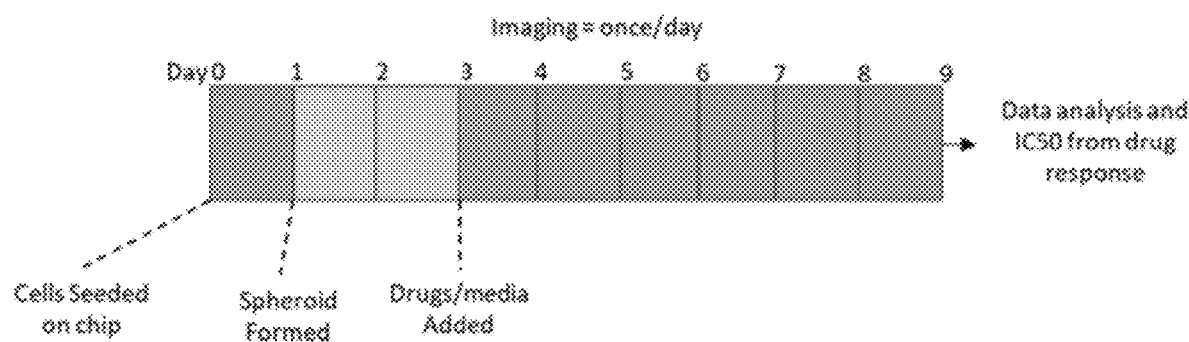
Figure 17A:
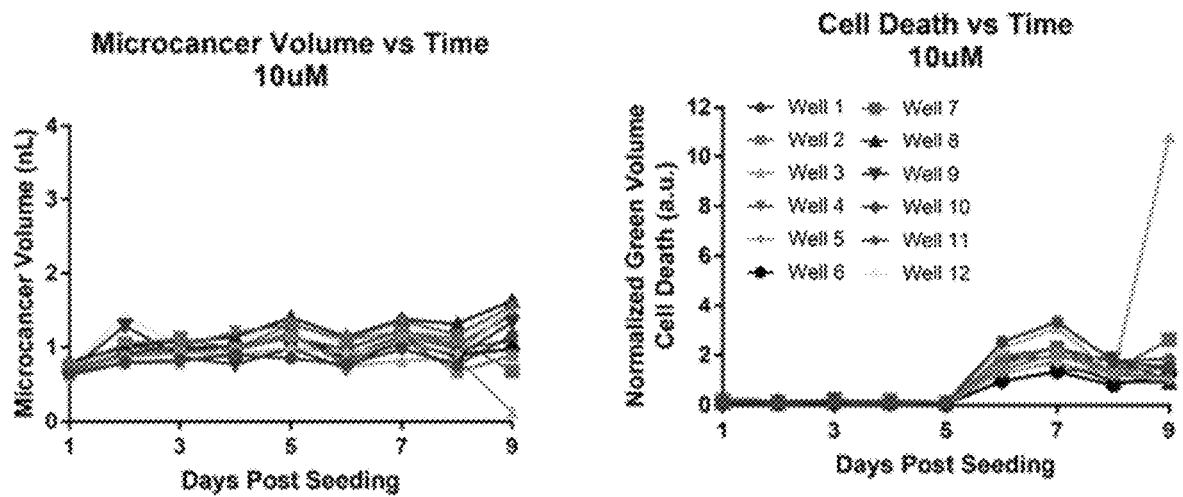
FIGS. 17A-17G. LN 229 microcancer drug testing with 6 different concentrations of Dasatinib and Negative Control.
Figure 17B:
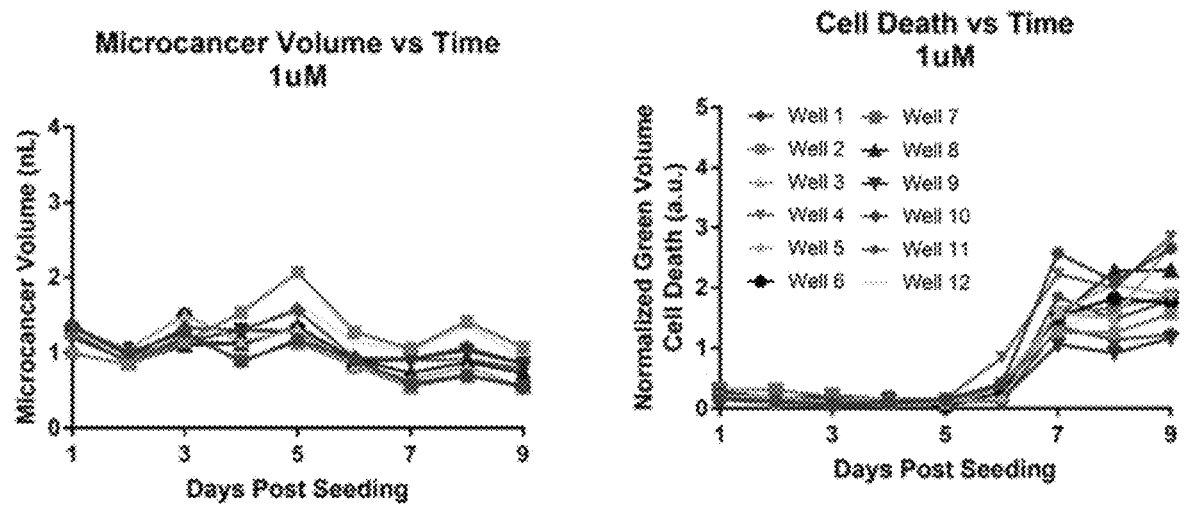
Figure 17C:
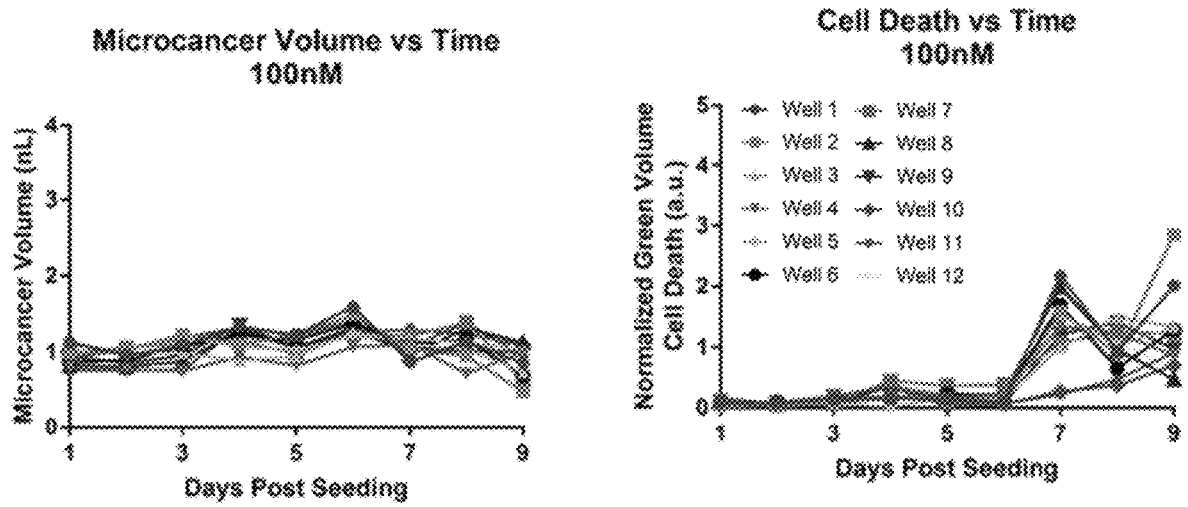
Figure 17D:
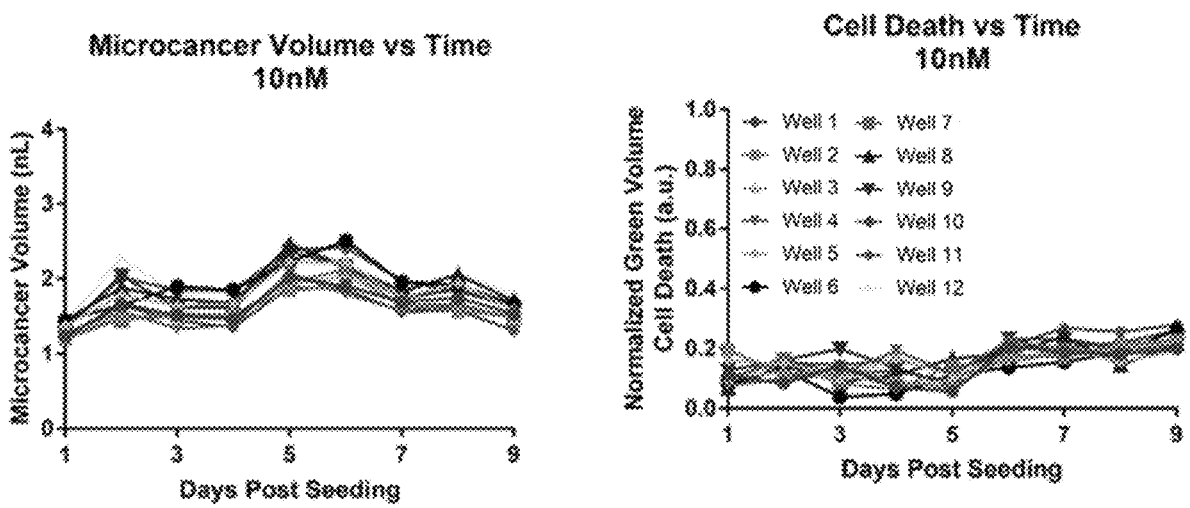
Figure 17E:
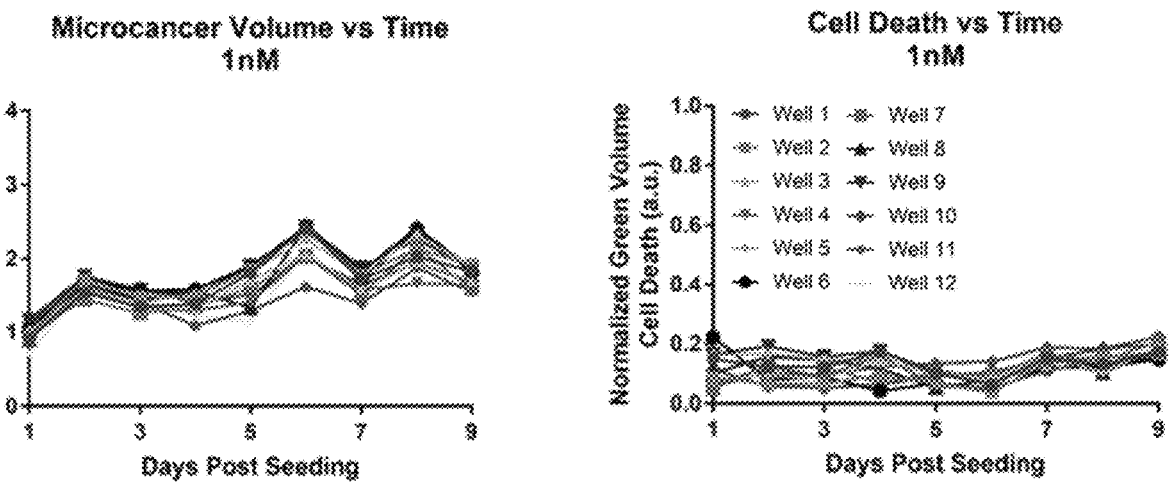
Figure 17F:
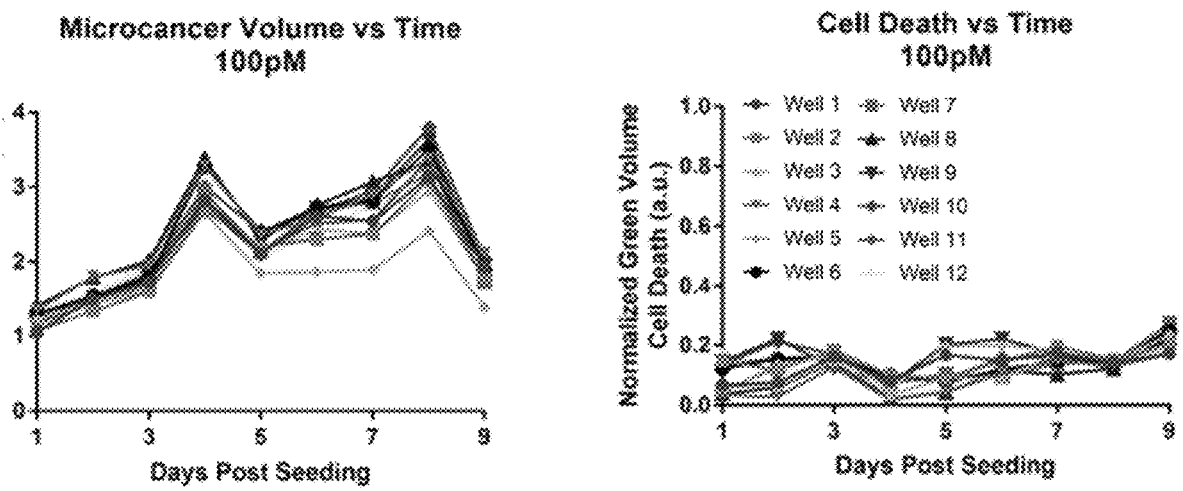
Figure 17G:
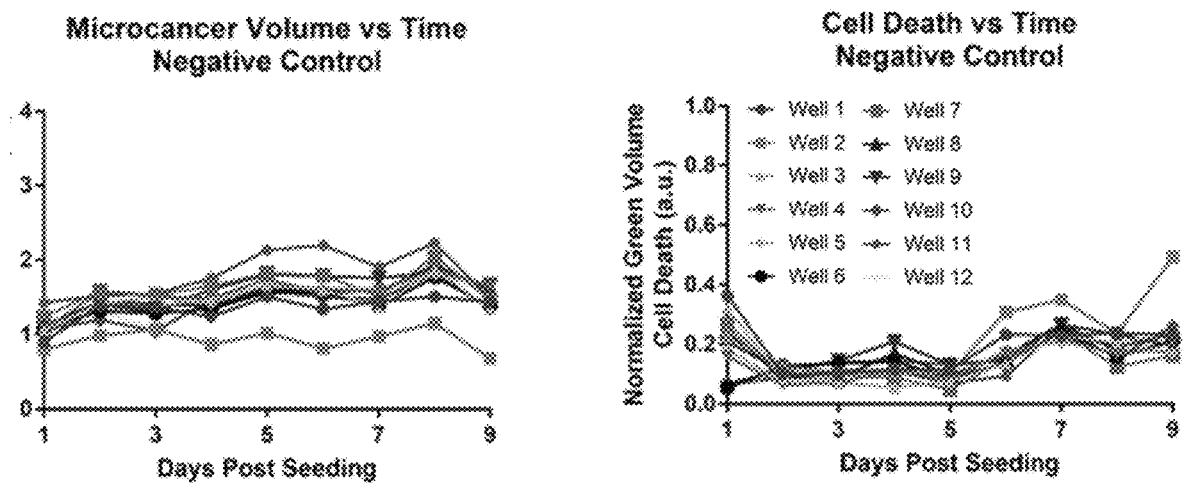
Figure 18A:
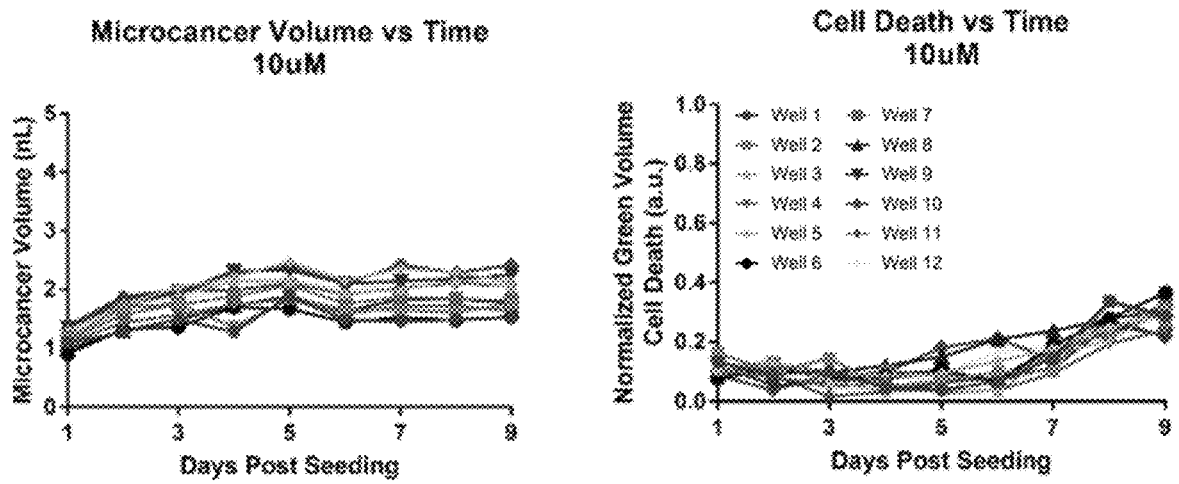
FIGS. 18A-18G. PDX microcancer drug testing with 6 different concentrations of Dasatinib and Negative Control.
Figure 18B:
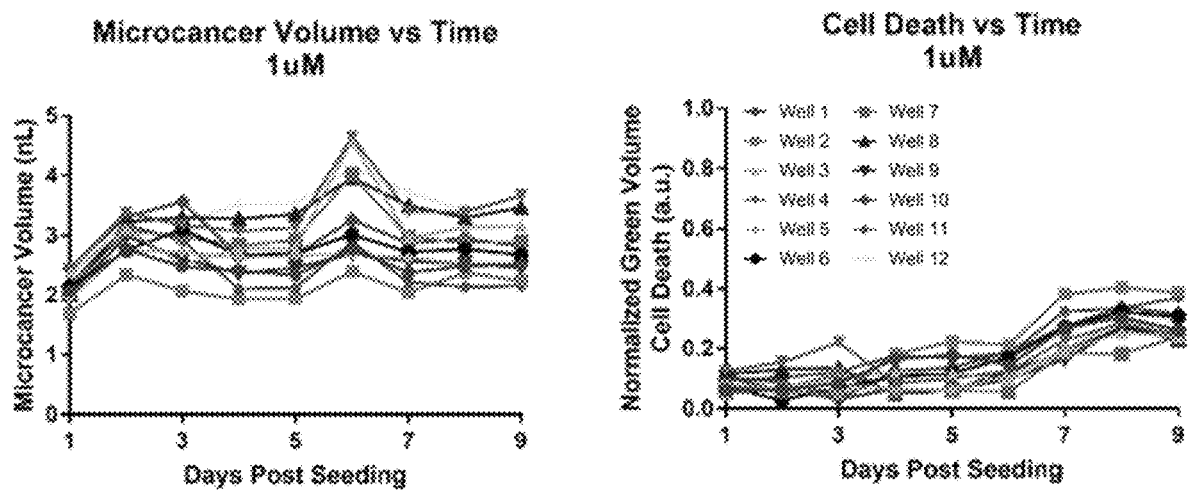
Figure 18C:
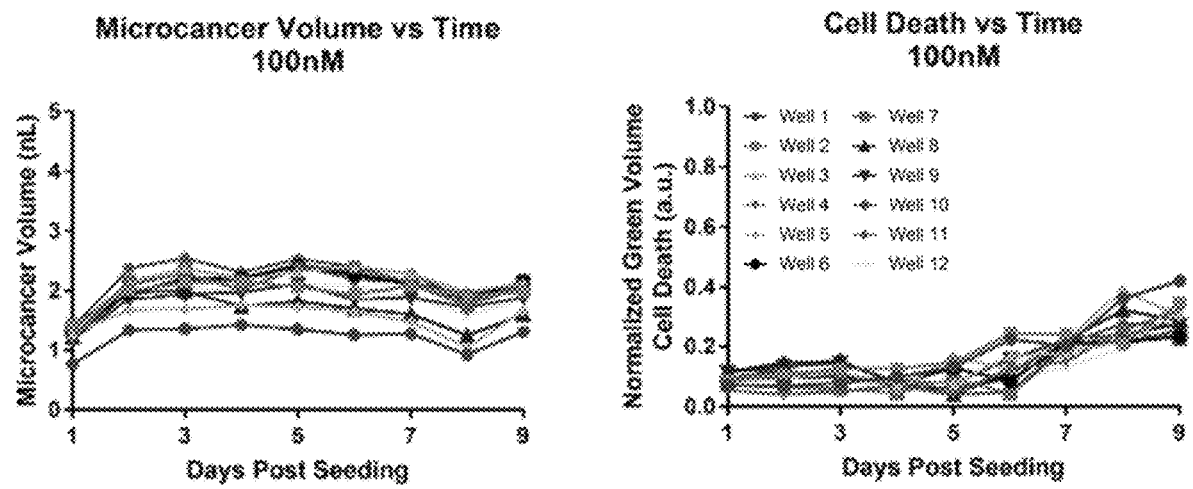
Figure 18D:
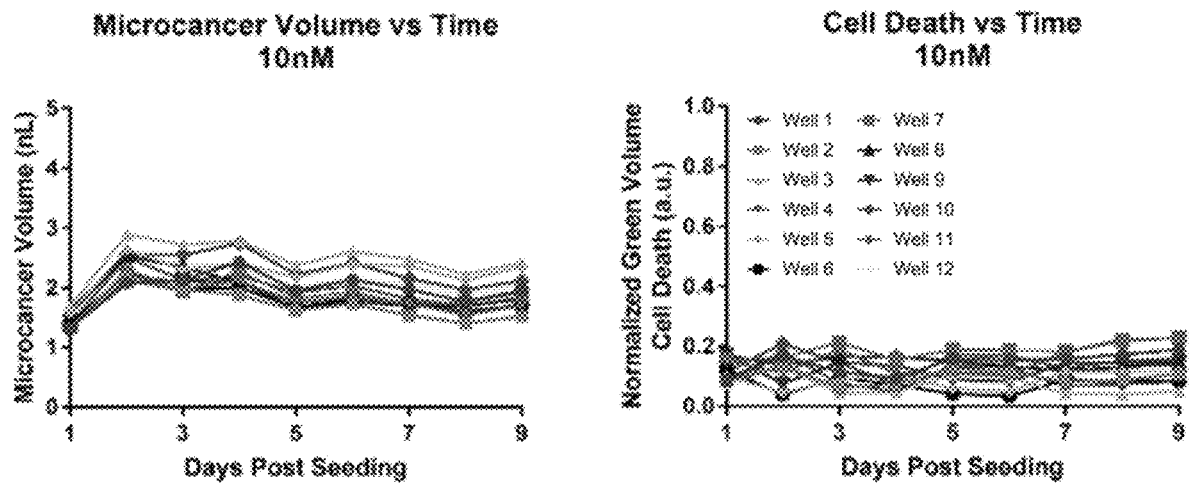
Figure 18E:
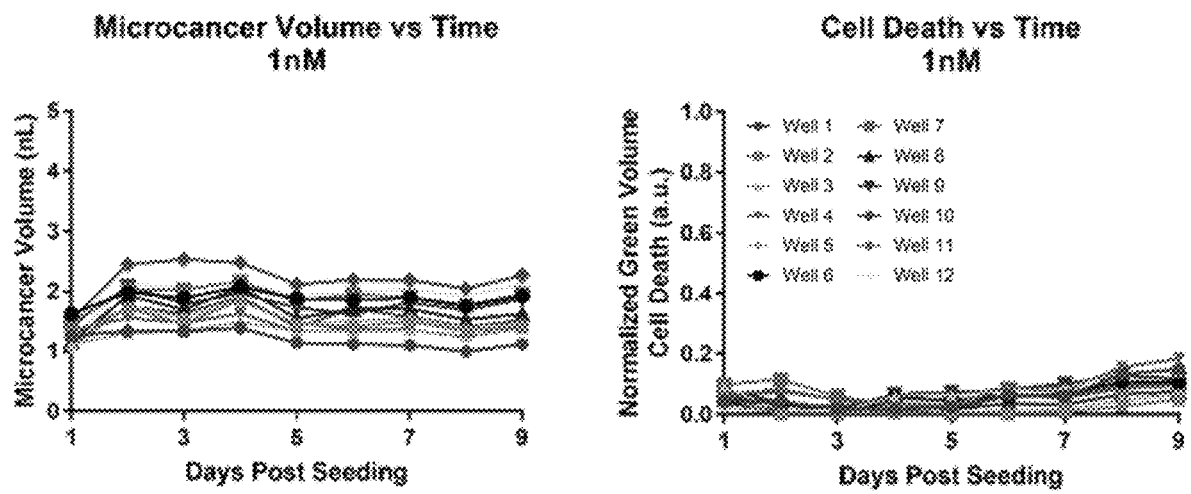
Figure 18F:
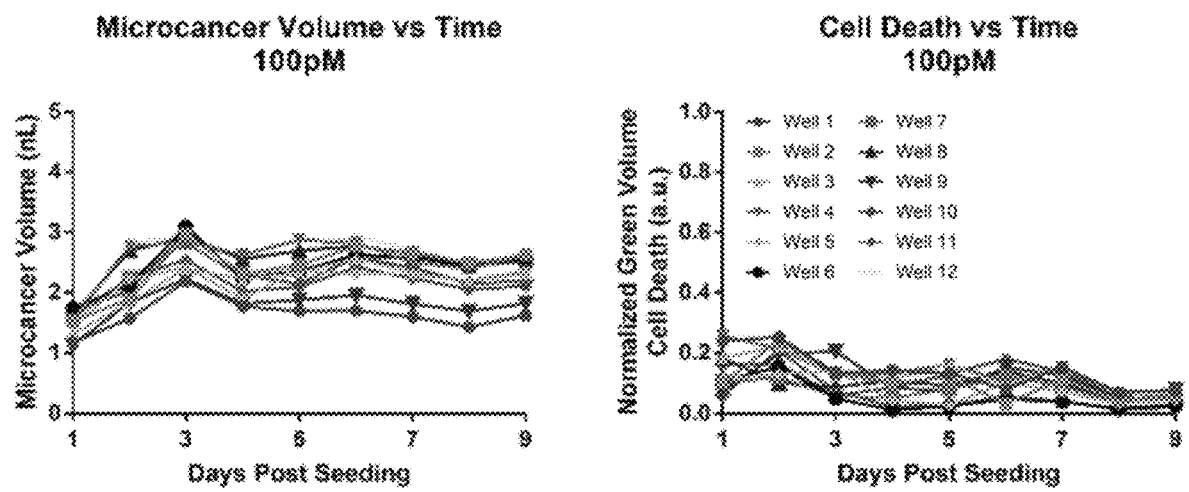
Figure 18G:
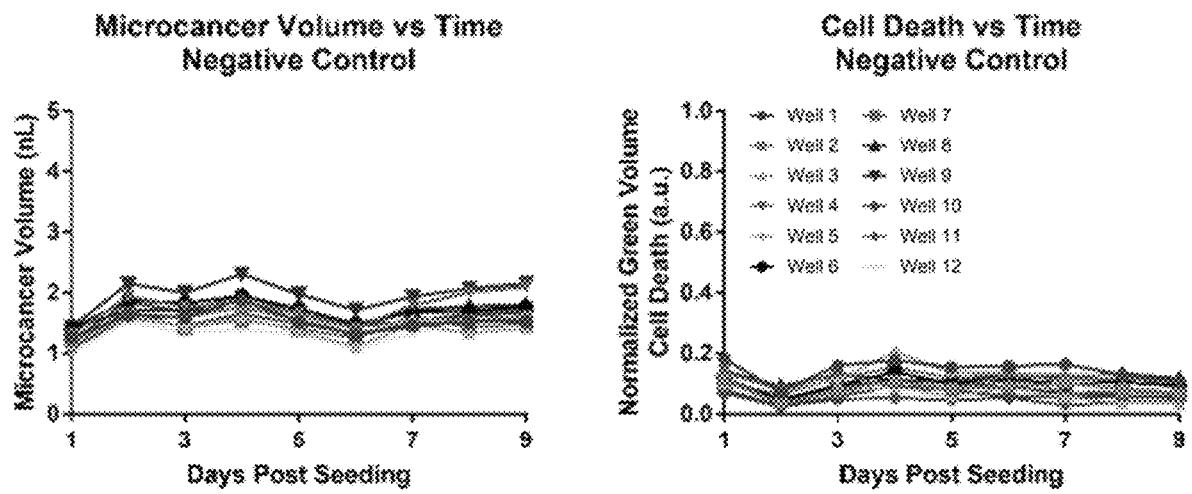

The chip was kept upright inside mineral oil and centrifuged briefly to bring down the spheroids. Next, appropriate volume of media with drugs is loaded on chip through oil and incubated for 30 minutes to reach a homogeneous concentration. The volume of drugs loaded depends on the number of spheroids being cultured or wells filled with media on chip, which in turn, are defined by the size and numbers of PDMS reservoirs initially used for cell seeding. The volume of media with drugs added is usually 5 times the volume of wells containing spheroids. The concentration of the drug is increased by an appropriate factor to account for the media without drugs already present in wells, resulting in the desired final drug concentration in the wells post diffusion. The chip was partitioned as before by using oil, inverted, and daily measurements of green and red fluorescence were taken. It is of note that this process can be used to periodically change media on chip for long-term 3D culture. FIG. 15A shows a timeline of drug testing experiments on chip.

Figure 4A:
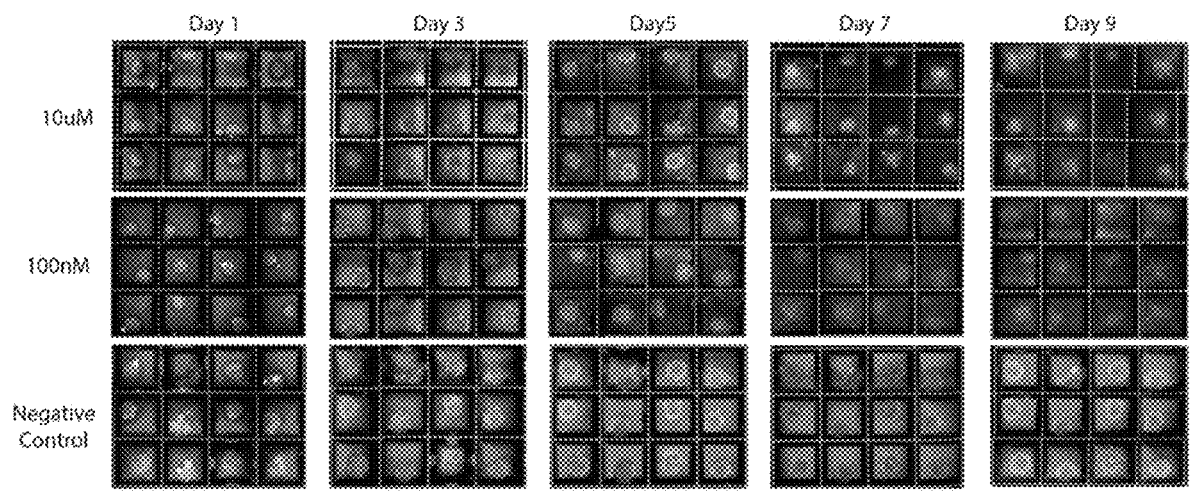
FIGS. 4A-4H. On-chip LN 229 and PDX drug testing.
Figure 4B:
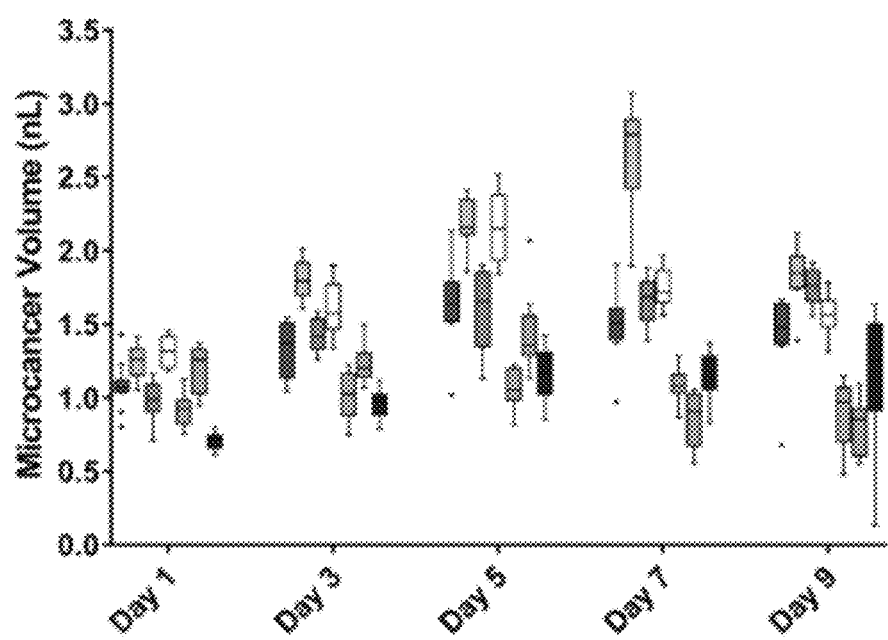
Figure 4C:
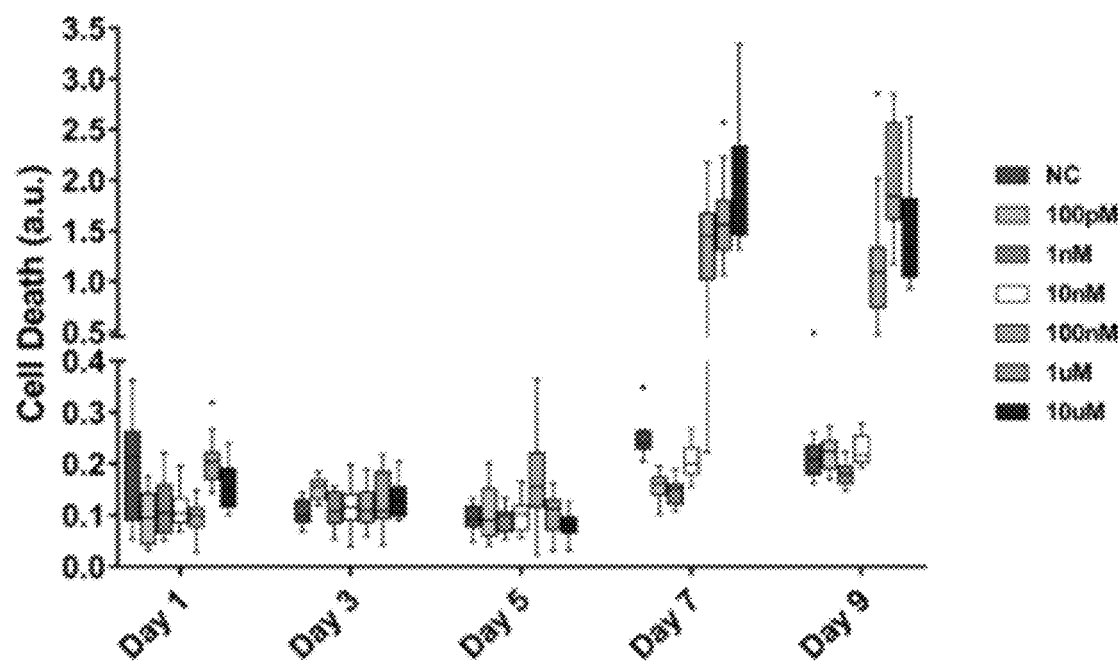
Figure 4D:
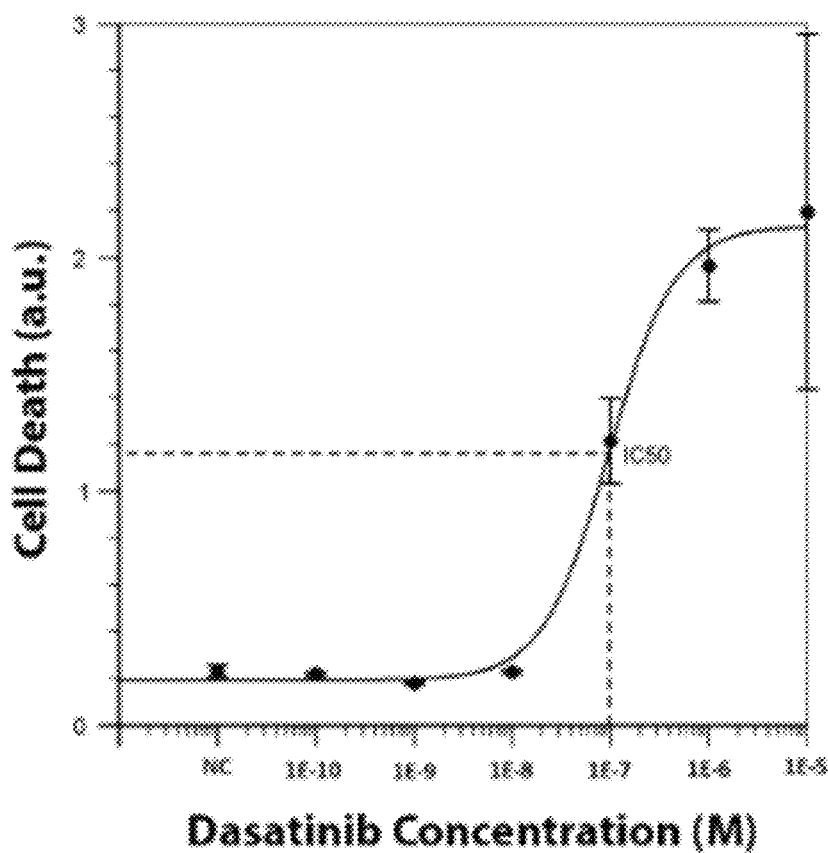
Figure 4E:
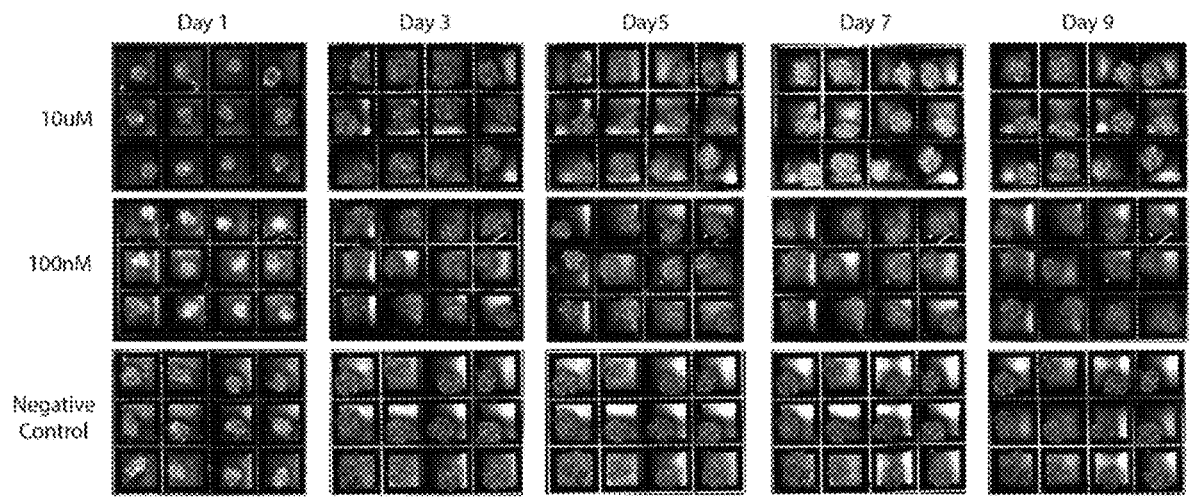
Figure 4F:
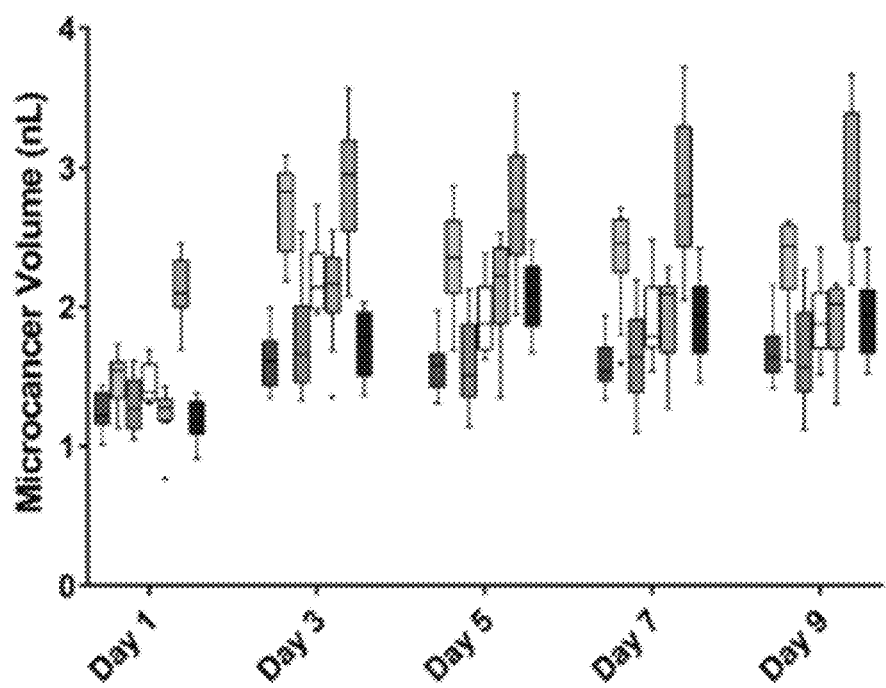
Figure 4G:
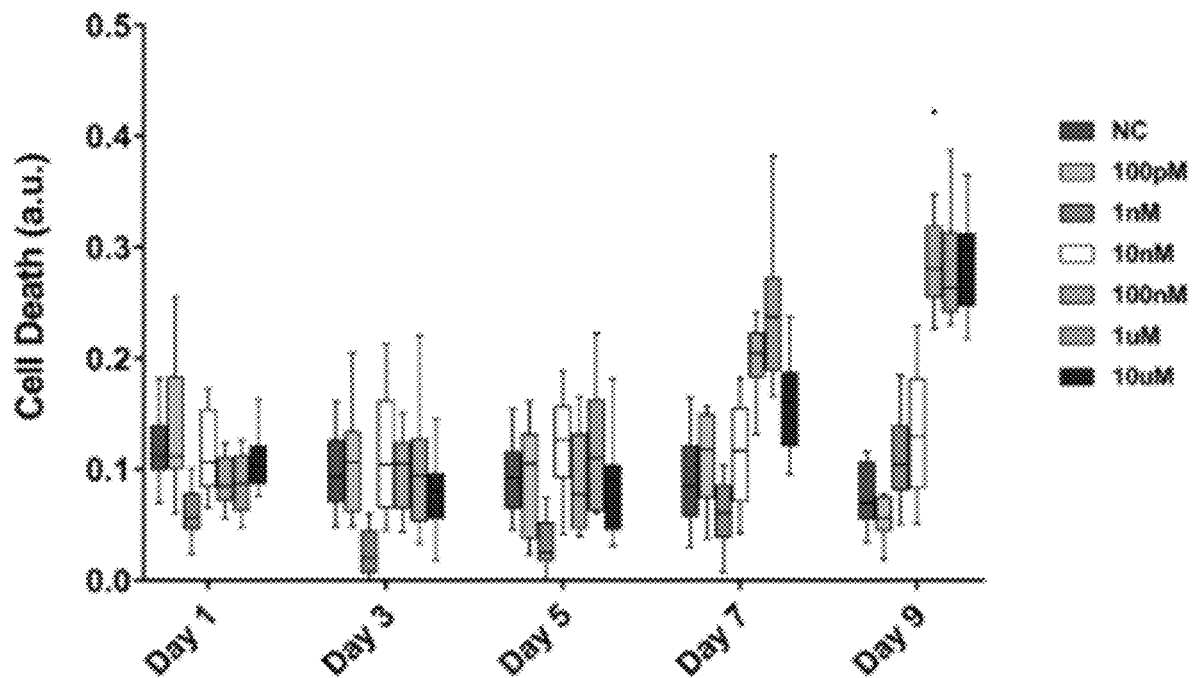
Figure 4H:
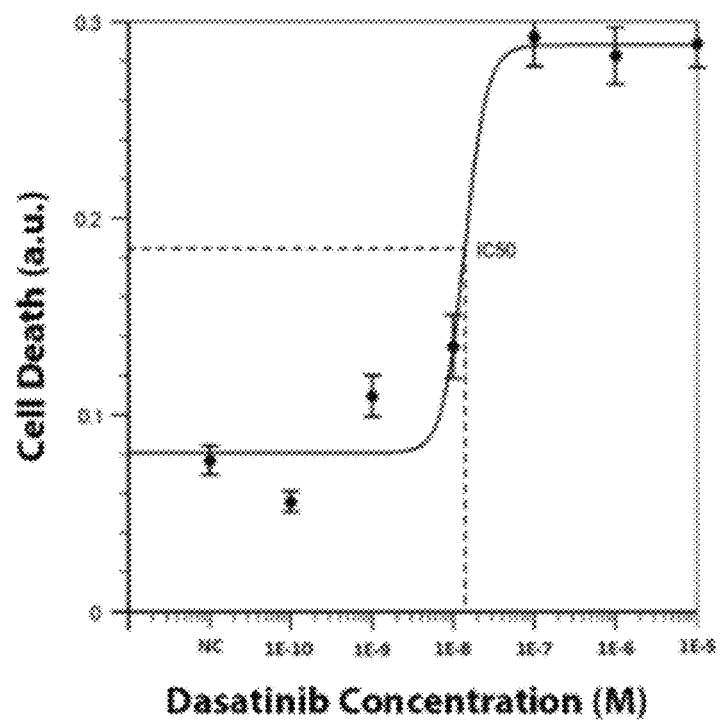

FIG. 4A and FIGS. 15B-E show the results of drug testing for LN229 microcancer spheroids. FIG. 4A shows alternate day maximum projection images for concentrations of 10 uM (top), 100 nM (middle), and no drug control (bottom). FIGS. 15B-E shows the same for concentrations of 1 uM, 10 nM, 1 nM, and 100 pM of Dasatinib drug, respectively. FIGS. 4B-C show the box and whiskers plots (n=12) of tumor spheroid volume and normalized cell death. It can be observed that for higher concentrations of drugs (10 uM, 1 uM and 100 nM), the cell death starts to increase as soon as 4 days after culture with drugs (Day 7 overall) compared to lower drug concentrations and the no drug control. The 1050 value for Dasatinib on LN229 microcancers was found to be 95.9 nM as measured on day 9 (FIG. 4D). Due to excessive cell death and destruction of spheroids for these high drug concentrations, the entire well starts to appear green in days 7 to 9, and hence the overall green volume captured exceeds the spheroid volume (red) and the normalization results in values greater than 1. Drug testing was also performed on PDX microcancers. FIG. 4E shows alternate day maximum projection images of drug administered PDX spheroids for concentrations 10 uM (top), 100 nM (middle), and no drug control (bottom), and FIGS. 16A-D shows the same for concentrations of 1 uM, 10 nM, 1 nM, and 100 pM of Dasatinib drug, respectively. FIGS. 4F-G show the box and whiskers plot (n=12) of PDX microcancer volume and normalized cell death. The 1050 value for Dasatinib on PDX microcancers was found to be 13.8 nM as measured on day 9 (FIG. 4H). However, the overall response to Dasatinib in terms of normalized cell death was lower for PDX, as the PDX microcancers remained intact even for higher drug concentrations. This result is in agreement with the inability of Dasatinib to affect tumor growth in GBM8 PDX in vivo, although it is highly effective in 2D culture. FIGS. 17A-G and FIGS. 18A-G show individual traces of volume and cell death as response to drug over time for 12 LN229 and PDX microcancer spheroids, respectively.

Example 8—Geometric Control in 3D Culture

Figure 5A:
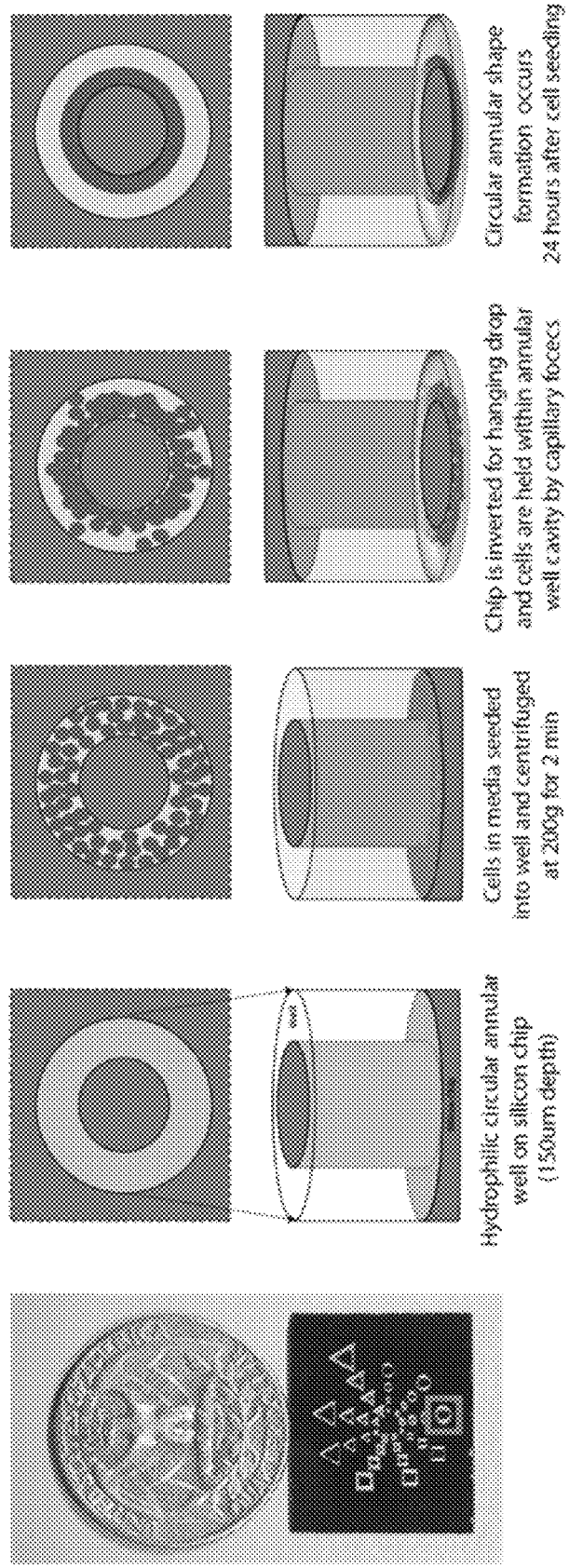
FIGS. 5A-5E. Geometric control in microchip hanging drop 3D culture.
Figure 5B:
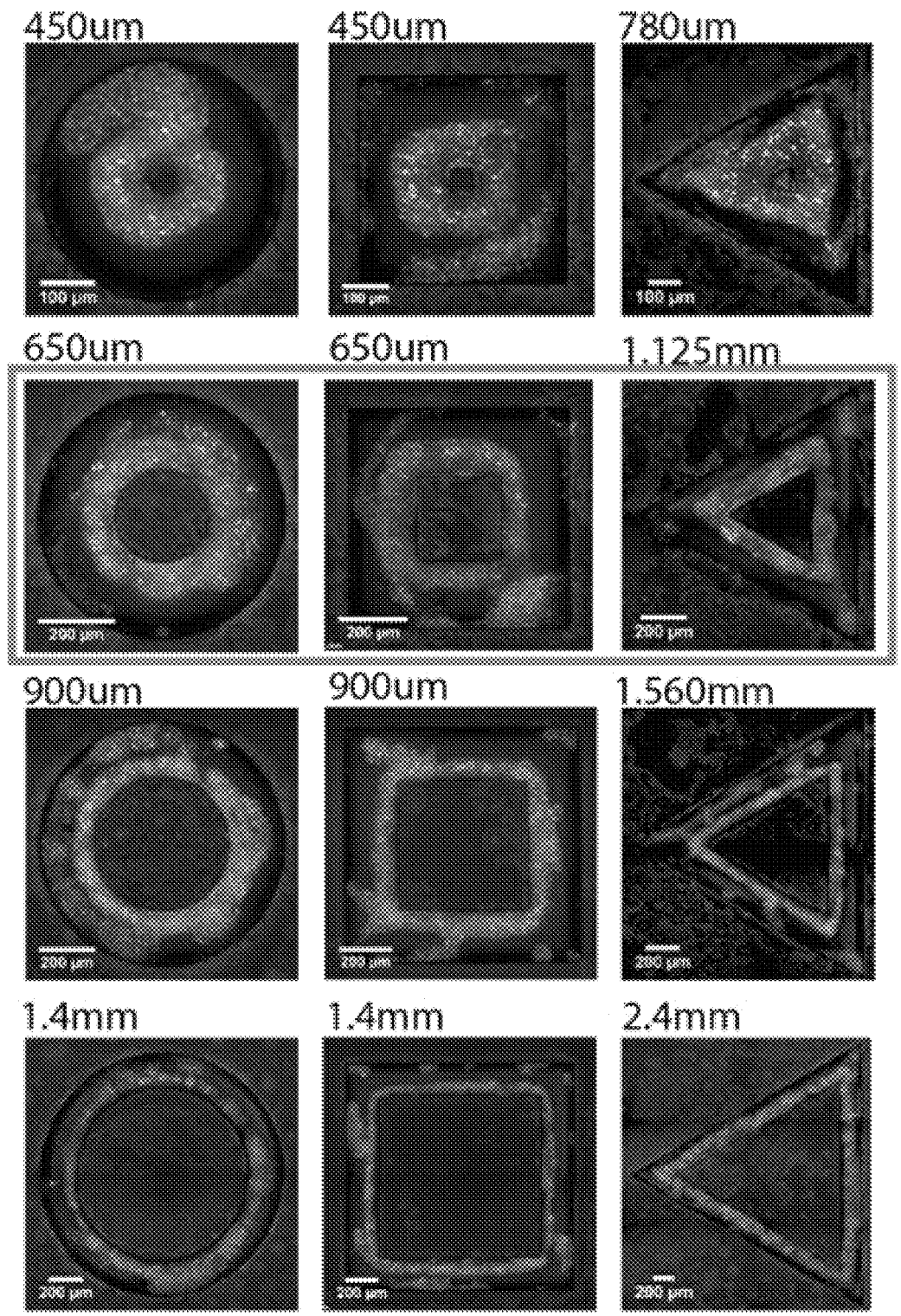
Figure 5C:
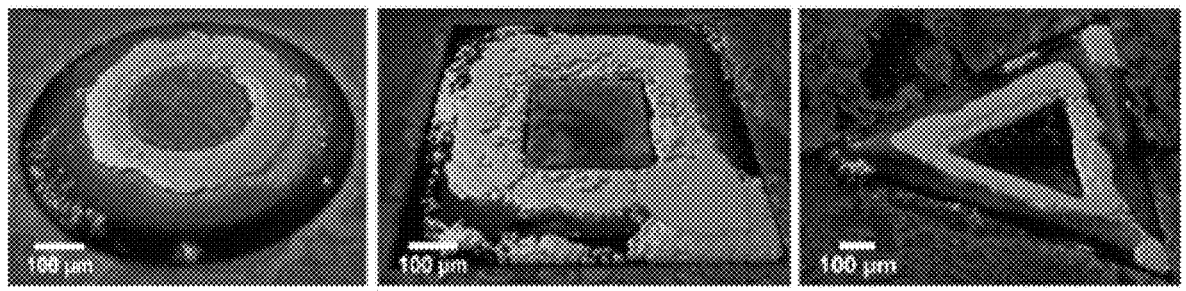
Figure 5D:
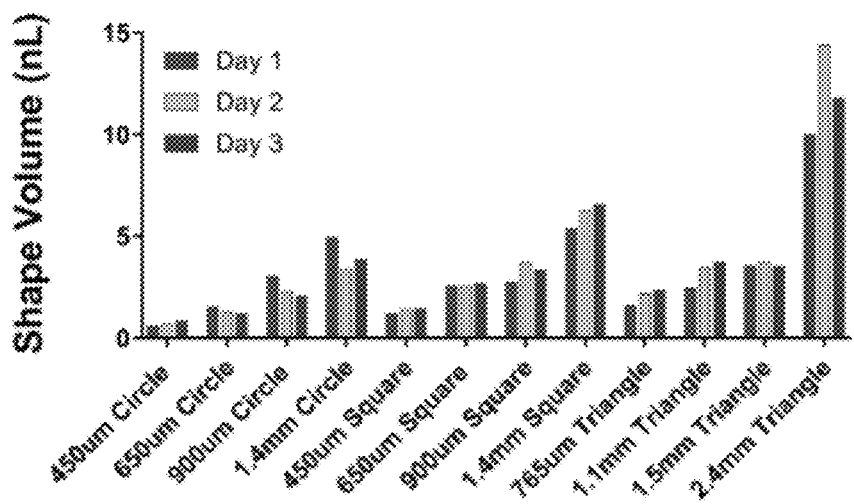
Figure 5E:
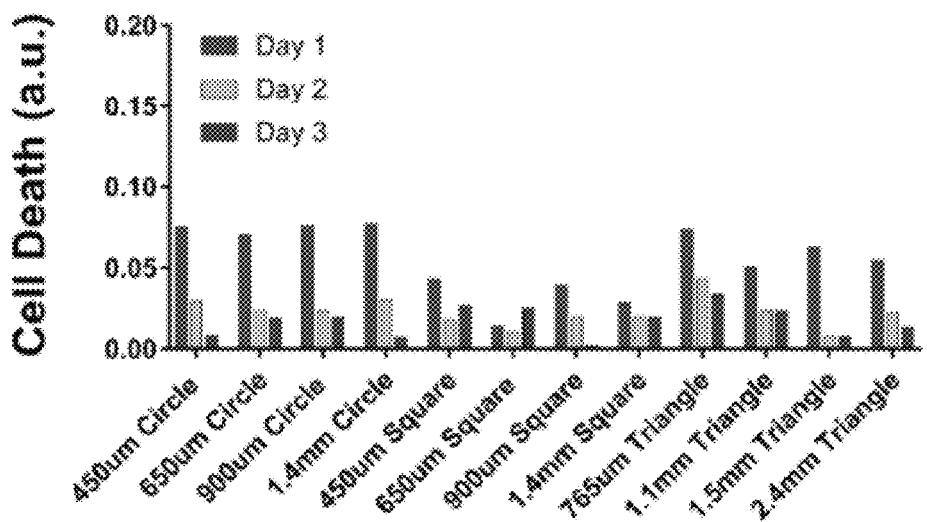
Figure 6:
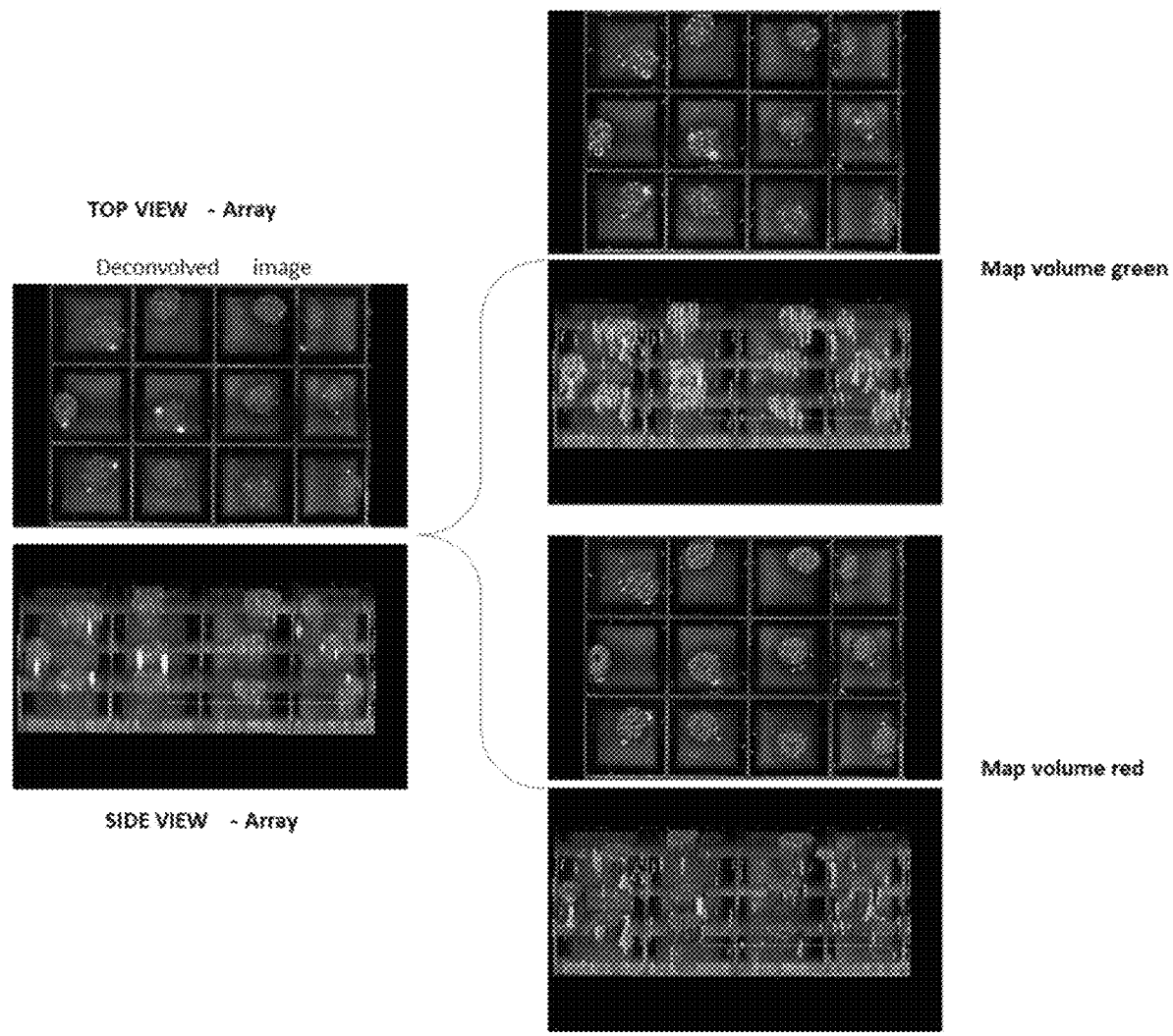
FIG. 6. Volumetric Analysis of Deconvolved images of 12 well microcancer spheroids. Analysis flow starts with deconvolved images of microcancer spheroids being analyzed. Cell death is mapped using green volume through local contrast thresholding and organoid volume is mapped using red volume surface mapping in Imaris. Top and side views of process flow is shown.
Figure 8E:
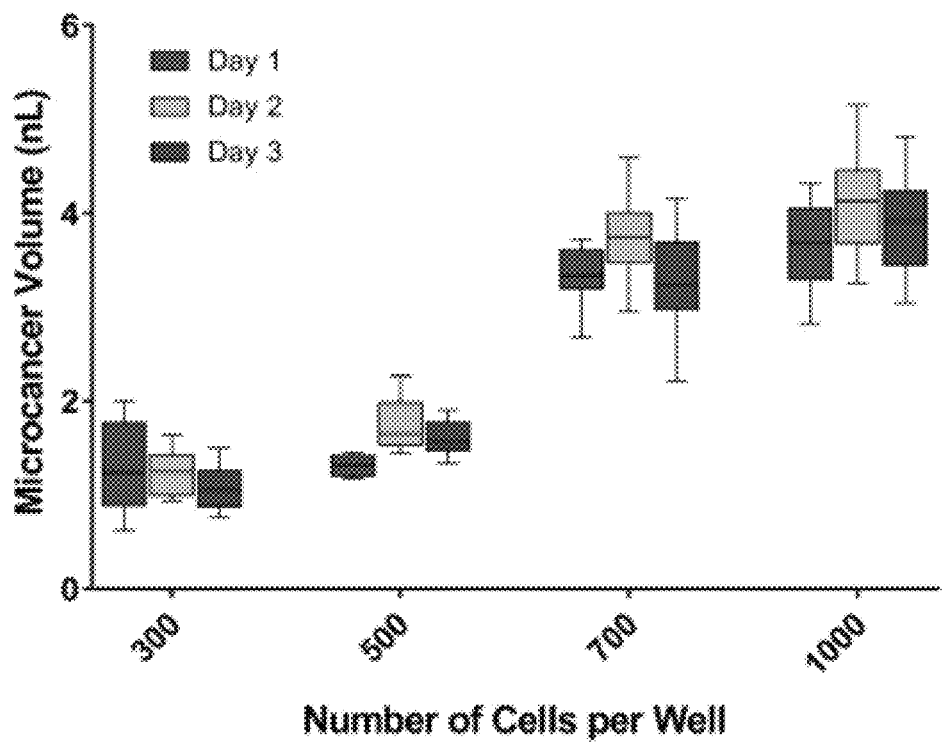
Figure 8F:
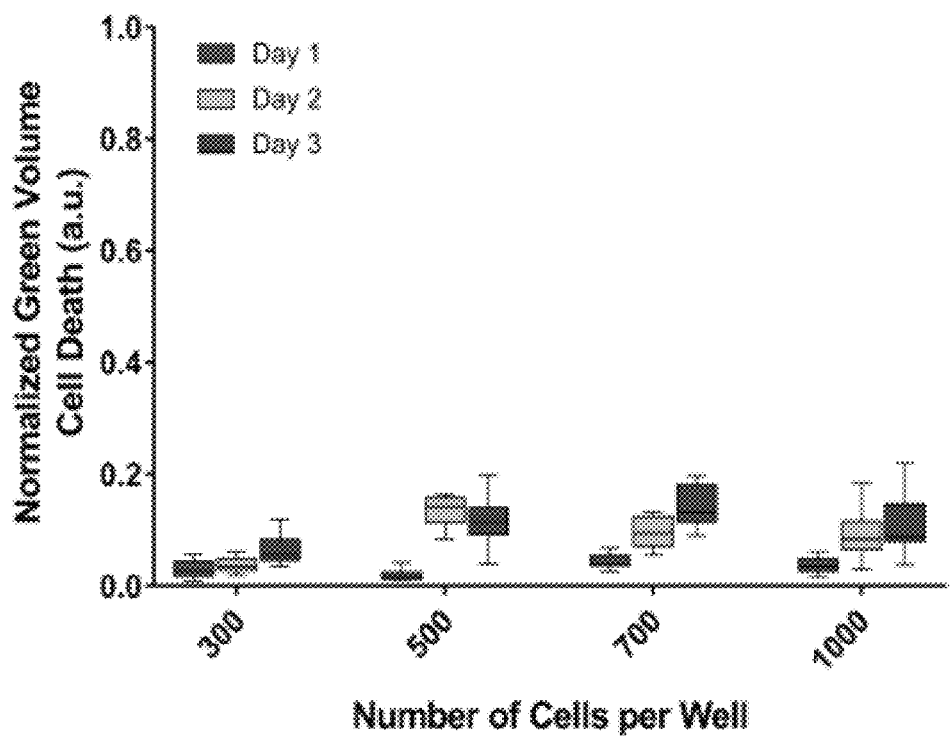
Figure 9A:
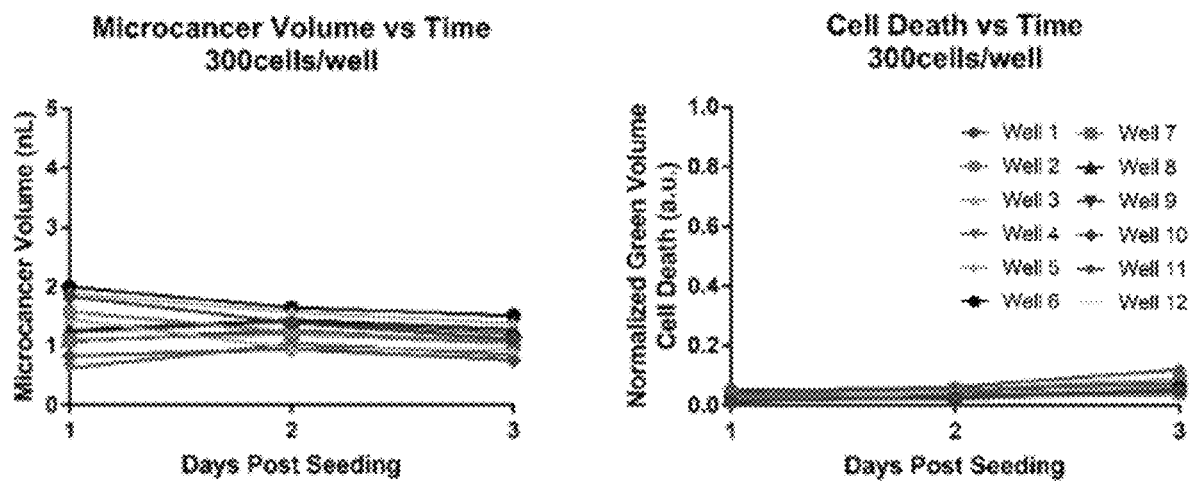
FIGS. 9A-9D. LN 229 microcancer volume and cell death tracking of 12 wells over three days post cell seeding.
Figure 9B:
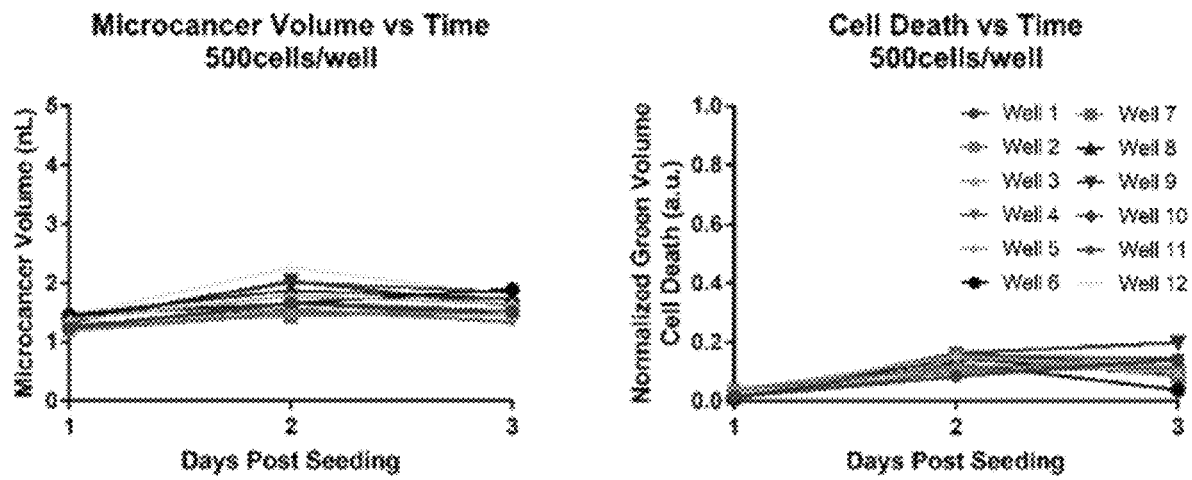
Figure 9C:
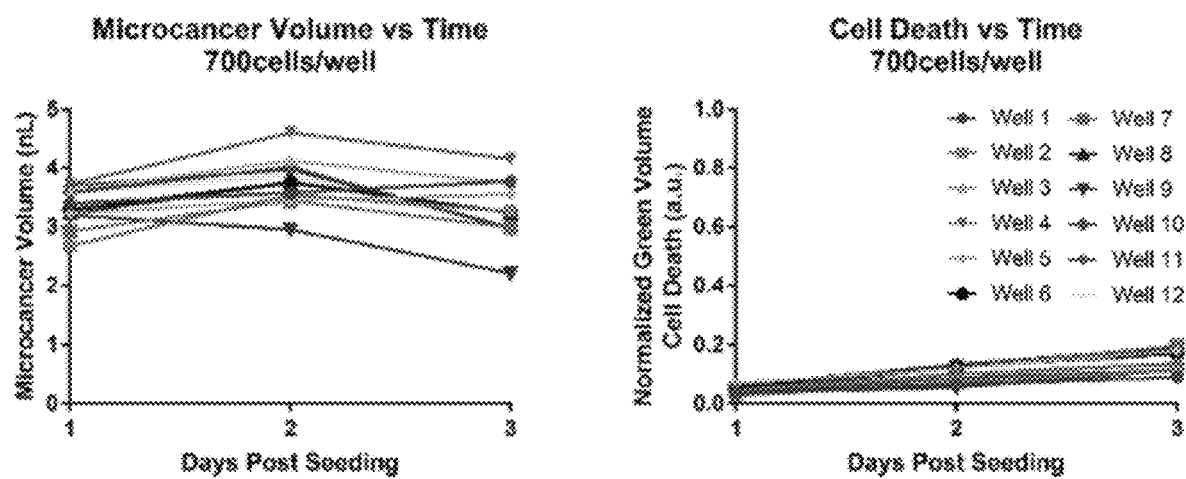
Figure 9D:
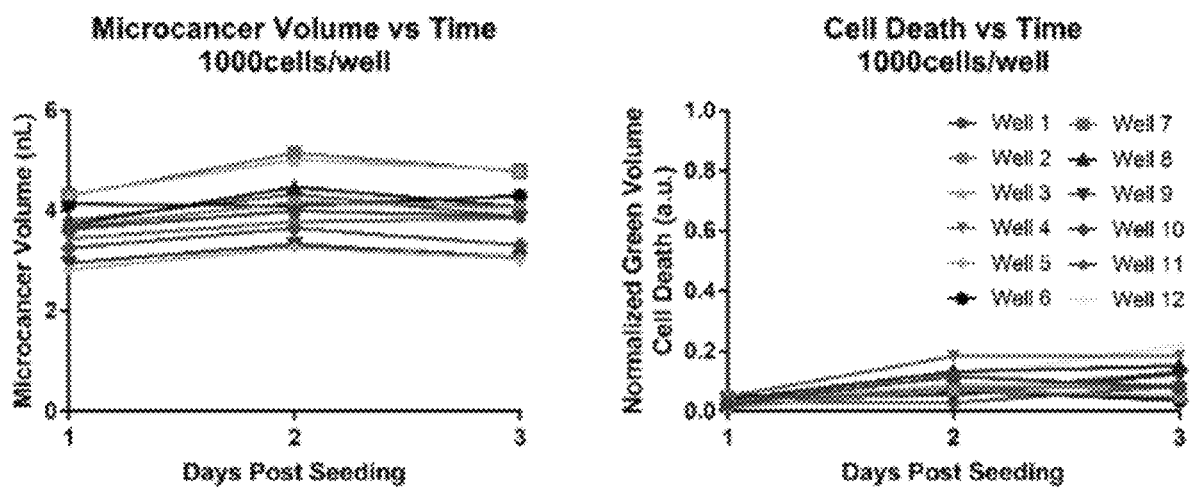
Figure 10A:
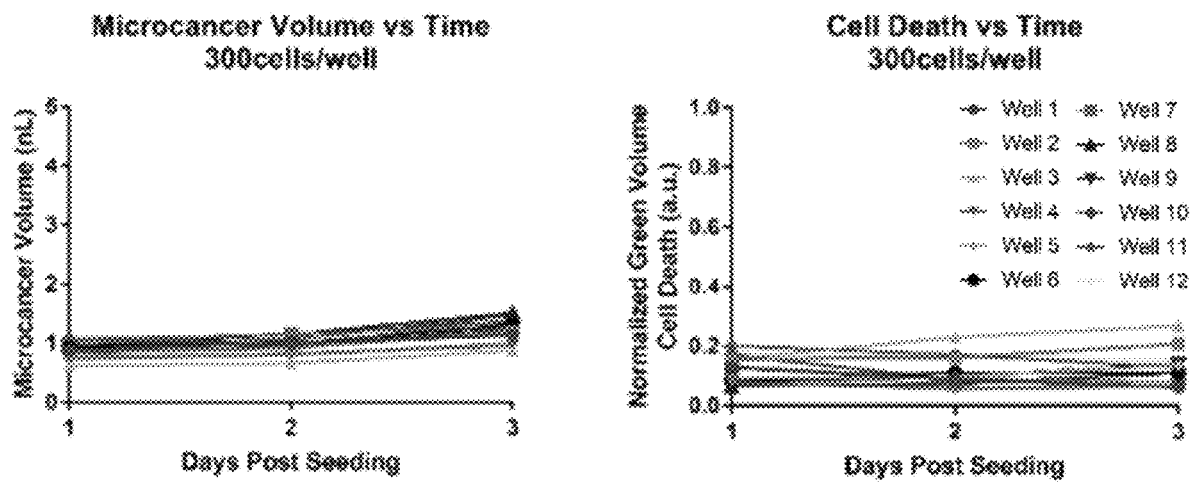
FIGS. 10A-10D. PDX microcancer volume and cell death tracking of 12 wells over three days post cell seeding.
Figure 10B:
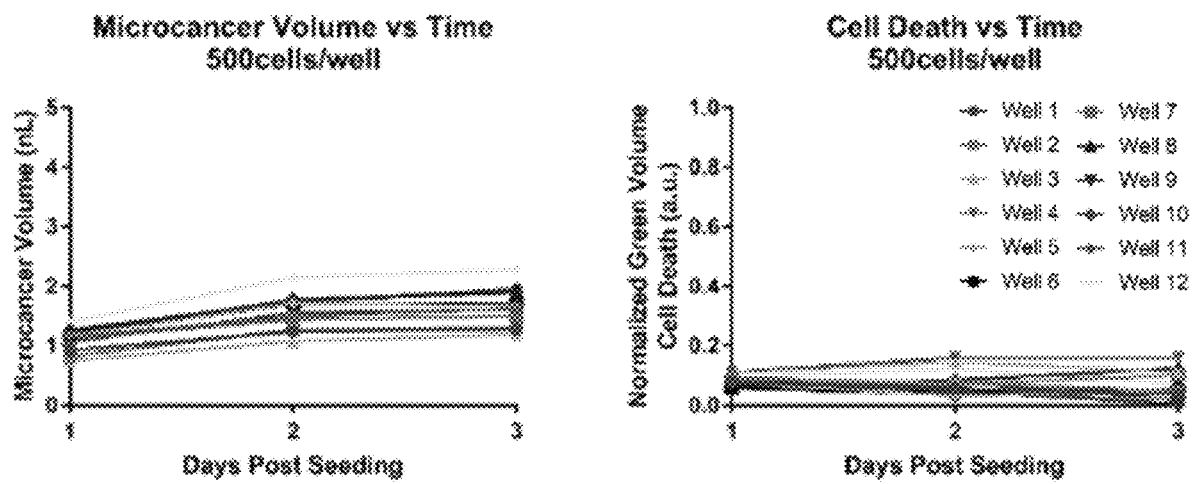
Figure 10C:
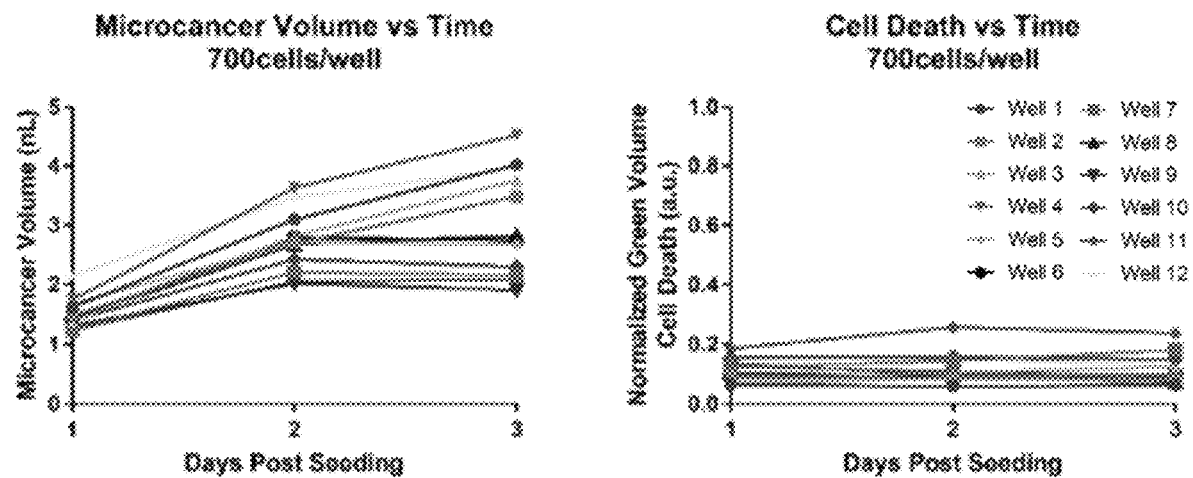
Figure 10D:
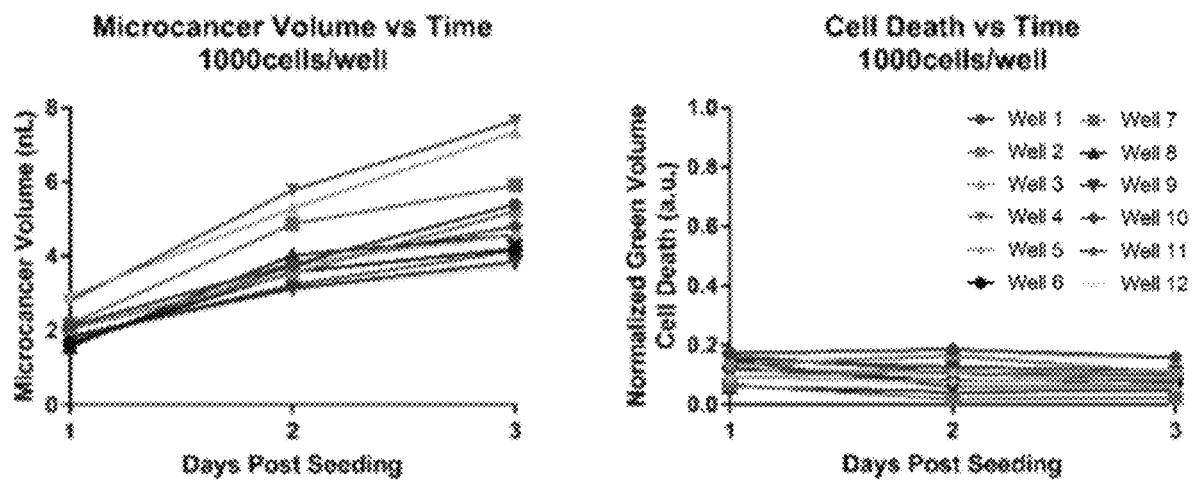
Figure 11A:
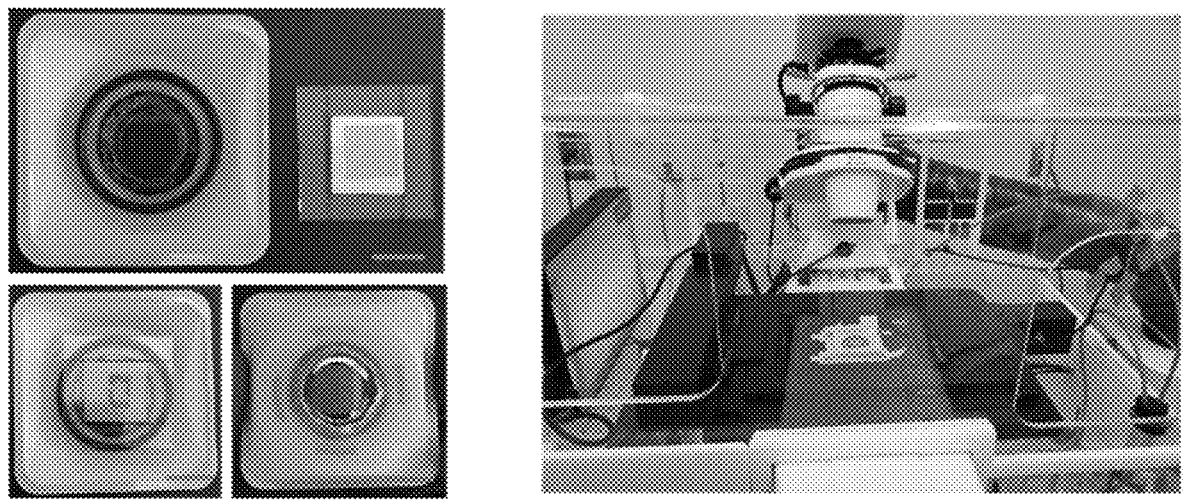
Figure 19A:
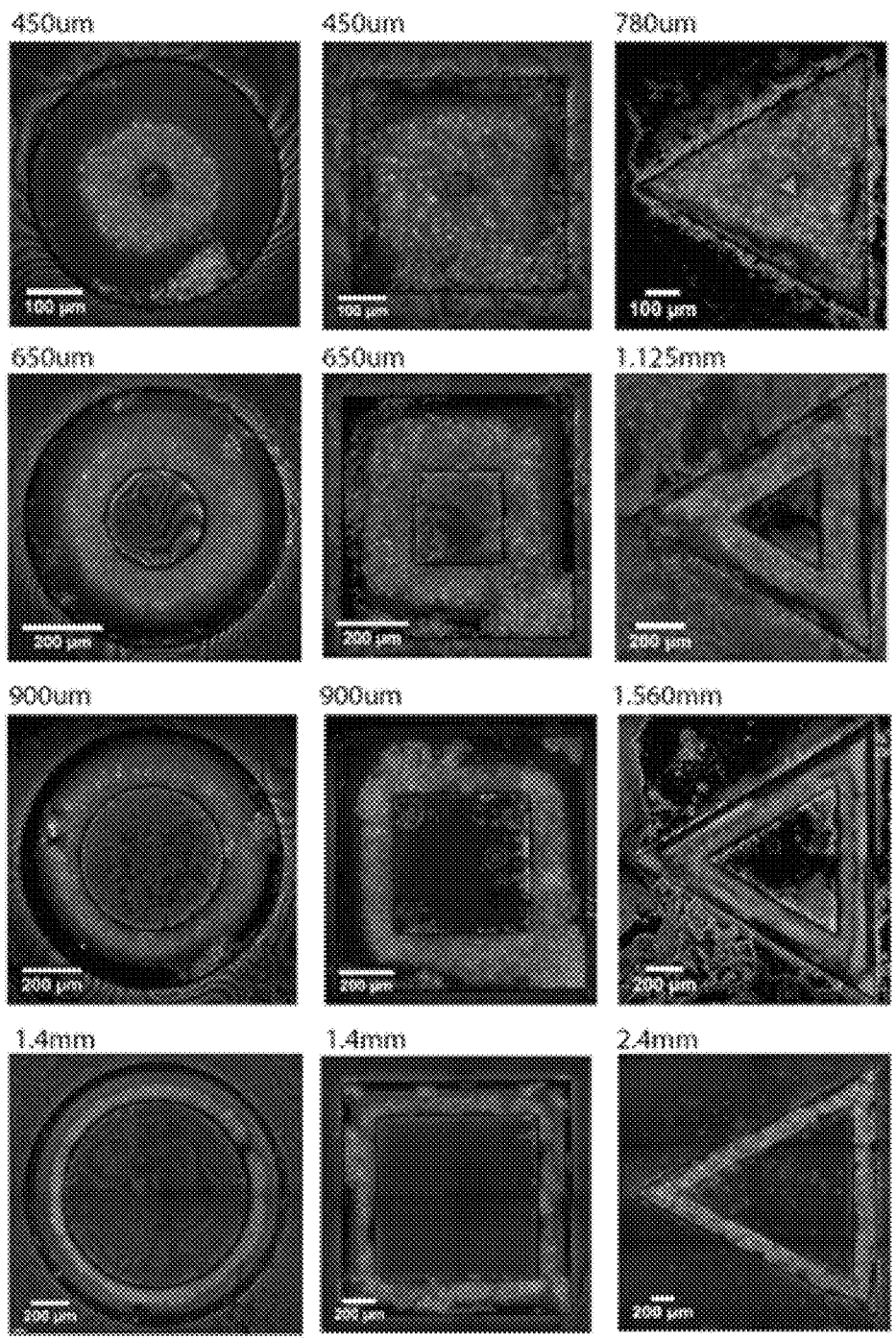
FIGS. 19A-19B. Fluorescence images of shape control in hanging droplet 3D culture (Days 2 and 3).
Figure 19B:
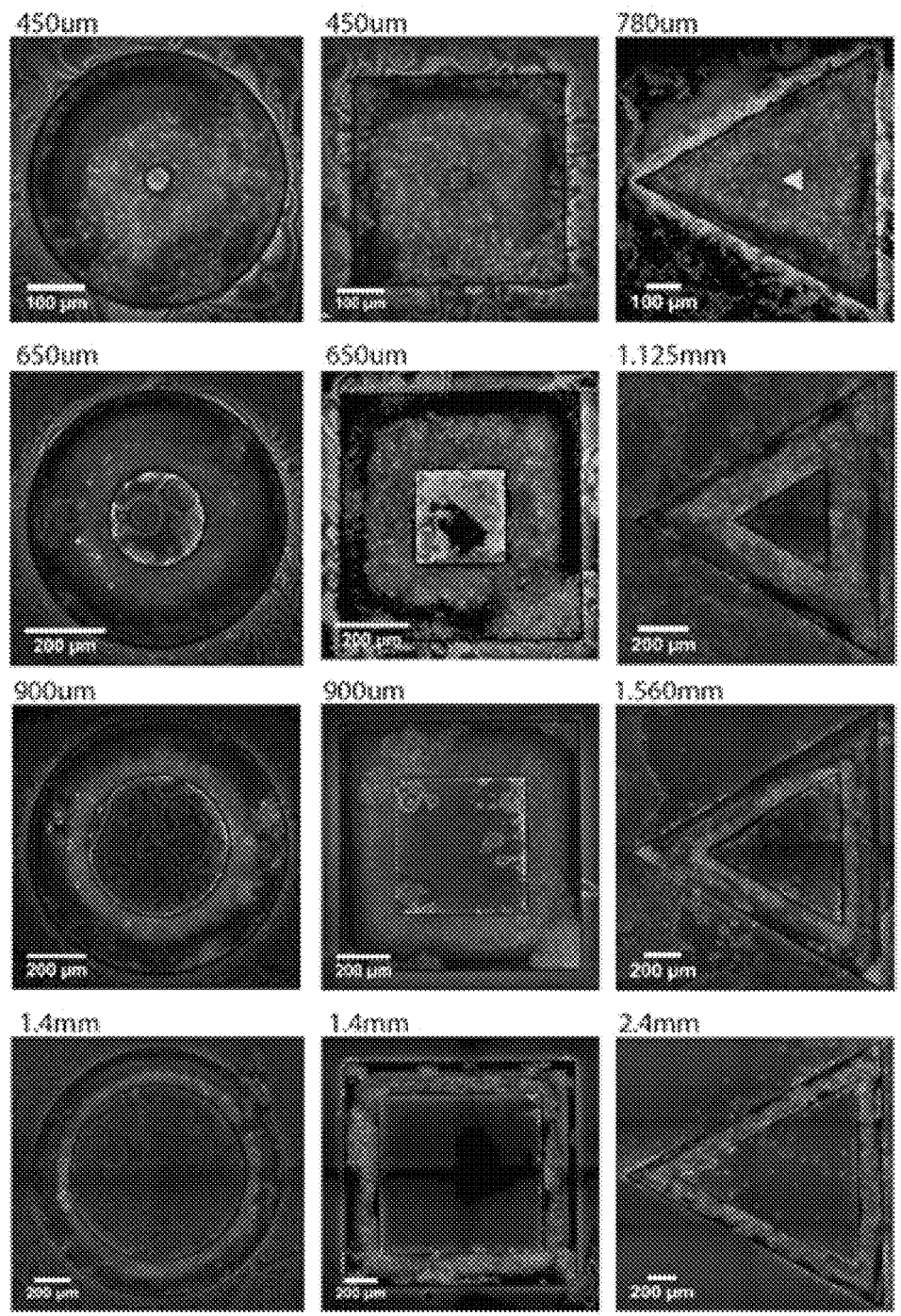

To evaluate the shape control capabilities of the present platform, a silicon microchip was fabricated with etched annular circle, square, and triangle channels. FIG. 5A shows the etched chip and describes the process flow for geometric shape formation in an annular circular channel. Briefly, the inside surface of the etched channel was made hydrophilic before cell seeding using oxygen plasma. Seeding of cells in a single step was performed similar to the previous experiments by assembling a detachable PDMS well. This was followed by droplet formation using oil shear as previously discussed. Droplet shapes conformed to the shape of the channel cavity due to capillary forces, allowing the generation of dense and continuous annular circular, square, and triangular 3D shapes. These shapes were cultured and imaged for 3 days. Media exchange for 3D shapes was performed every day in the same manner as the drug loading procedure described in previous sections and more details can be found in Example 15. On the microchip, the diameter of circular shaped channels and side length of square shaped channels ranged from 450 um to 1.4 mm, whereas the side length of triangular shaped channels ranged from 780 um to 2.4 mm. In the experiments, the channel width (between the internal post and outer boundary) was kept constant at 200 μm. FIG. 5B shows the fluorescent microscopic images of these 3D shapes formed. It was found that one day after cell seeding, continuous shapes were formed with widths of 70-100 μm for annular circles and squares, and, 120-160 μm for the annular triangles which were the largest of the shapes. Fluorescence images taken on days 2 and 3 post cell seeding can be seen in FIGS. 19A-19B. It can be noted that by Day 3, minor fragmentation in the 900 um and 1.4 mm circular shapes begin to occur possibly due to continued cellular compaction and the absence of any external matrices in the system. Furthermore, volumetric mapping and analysis of these shapes was conducted to determine the shape volume (PKH dye mapping) and cell death (celltox dye mapping) (FIG. 5C). The bar graphs for the volume and cell death of different annular shapes for 3 days of culture on chip is shown in FIG. 5D-5E. Due to the large range of sizes that can be simultaneously tested on the platform, the volumes on chip spanned from 0.6 nL-10 nL on day 1 to 0.86 nL-11.8 nL on day 3. Cell death of these shapes, as can be seen in FIG. 5E, remained less than 8% for all three days of culture. The present platform allows geometric control in hanging drop format with sizes ranging from a few hundred microns to several millimetres while allowing characterization of multiple shapes on a single chip. Geometry control is a particularly useful aspect for examining impact of different stresses and stress gradients and in applications where precise shape control of tissue structures are needed, such as in regenerative medicine applications.

Materials and Methods: Off Chip Culture

The LN 229 cells were cultured in the Dulbecco Modified Eagle Medium without sodium pyruvate (Gibco) including 10% (v v$^{-1}$) fetal bovine serum (FBS) (ThermoFisher), 1% (v v$^{-1}$) non-essential amino acids (ThermoFisher), and 2 mM L-glutamine (ThermoFisher). After getting a 70-80% of cell confluence, they were trypsinized with 0.25% (w v–1) Trypsin 0.53% (w v–1) EDTA solution (Gibco) and loaded to chips. For the PDX cells, 1% of penicillin-streptomycin (Lonza) was added to the media for LN 229 cell culture. They were cultured for two days after thawing the PDX cells from liquid Nitrogen tank to get the estimated counts, then loaded to chips. For the automated live cell imaging on the inverted microscope, the culture media also included 10 mM HEPES (4-(2-Hydroxyethyl)-1-piperazineethanesulfonic acid) buffer.

Chip Fabrication: Three types of chips are created. The first silicon chip has a microarray of wells of gradient sizes between 100 um to 500 um (each side of the well). The second chip (10 m×10 mm) has microarray of wells (each 300 um×300 um) with a depth of 120 um. Finally, the third chip that was fabricated was for 3D shape formation (for geometric control experiments). This chip included annular circle, square, and triangle shapes of different sizes. To further explain, each shape was fabricated with an outer and inner boundary. For the circle and square shapes, the diameter/side lengths of the outer boundary were 450, 650, 900, 1400 um. The inner boundary diameter/side lengths (inner posts) of these shapes were 50, 250, 500, 1000 um, respectively. The triangle shapes were of the size such that the circle shape could be circumscribed within its boundaries; so the side dimensions of the outer boundaries were 780, 1125, 1560, 2450 um and the inner boundaries (inner posts) were 318, 663, 1098, 1988 um.

Chip fabrication of all oxidized silicon chips were done in the same method. A 4-in. <100> silicon wafer (University-Wafer, South Boston, MA) with one side polished was thoroughly cleaned and used as the substrate in the photolithography process. The wafer was dehydrated on a heating plate at 140° C. for 2 min and cooled for 30 sec before loading into a Molecular Vapor Deposition (Applied Micro-Structures, San Jose, CA). A single layer of Hexamethyldisilizane was deposited under low pressure to the polished side of the wafer, increasing the hydrophobicity of the wafer surface. After the deposition, the wafer was unloaded and dehydrated on an aluminum hot plate at 110° C. for 2 min and cooled for 30 sec. Thereafter, positive photoresist SPR 220 (MicroChem, Newton, MA) was spin-coated on the polished side of the wafer to form a 4.5 µm covering layer, followed by a soft-bake at 60° C. for 2 min and 110° C. for 1 min. The photoresist was then exposed with an i-line (365 nm) mask aligner (EVG 620) in a hard contact with an expose dose of 210 J/cm$^2$. The exposed regions with the outline of the microarray pattern were subsequently removed by immersing the wafer in AZ 400K developer diluted 1:5 with deionized (DI) water for 45 seconds. For the anisotropic etching of the silicon substrate, a Bosch process reactive-ion etching (RIE) with alternating steps of $SF_6/O_2$ etching and $C_4F_8$ passivation was used to create a 120 µm deep trench. After the Bosch process, the remaining photoresist was cleaned with acetone and isopropanol rinses. The photoresist was stripped with heated (100° C.) PR Stripper 1165 for 10 minutes and sonicated for another 10 min, leaving the bare silicon exposed. Finally, the wafer was thermally oxidized in a furnace (1150° C.) for 60 min to grow 137 nm $SiO_2$, and subsequently, scribed into individual chips.

Cell Seeding on Chip: To prepare for cell seeding, the chips were cleaned using a piranha etch to rid of any organic residues on the surface of the wells. About 45 minutes before use, the chips were rinsed with acetone and isopropanol, and dipped in ethanol (200 Proof) for 2 min. Thereafter, the chips were blow dried with nitrogen gas and kept in a covered petri dish. Before cell seeding, a cured PDMS polymer with a reservoir of a size according to the required number of exposed wells was attached to each chip, and the chips were made hydrophilic through $O_2$ plasma treatment at 300 W for 3 minutes.

The total number of cells to be loaded on a single chip was equal to the product of the number of wells to be filled with cells (in the PDMS reservoir) and the number of cells needed per well (organoid size control). The cell density was calculated by dividing the total number of cells by the area of the exposed wells. The cell density was kept constant for the well gradient and 300 um array chips: 4883 cells/mm$^2$.

The total number of cells were extracted from the off-chip culture into a 1.7 mL tube and then centrifuged at 200 g for 5 min so that all cells settle to the bottom of the tube. After aspirating the supernatant, the cells were washed with serum free media and centrifuged at 400 g for 5 min. After, a PKH26 Red Fluorescent Cell Linker Kit for general cell membrane labelling (Sigma-Aldrich) was prepared according to product instructions and mixed with the cells. To stop the PKH 26 Red Fluorescence staining, media with FBS was added to the cell and dye solution. The cells were again centrifuged at 400 g for 5 minutes to bring all cells to the bottom of the tube and subsequently the supernatant was discarded. CellTox Green Cytotoxicity Assay (Promega), a green dye required to determine cytotoxicity and compatible with real time imaging, was prepared according to product instructions (1:500 ratio of dye to media) in media with serum. This media and green dye solution was then added to the cell suspension in the total volume required to seed on to the chips. For PDX cells, the cell seeding process was the same, except all media used included 1% Penicillin-Streptomycin.

The cells are then seeded on chip and centrifuged in a petri dish at 200 g for 2 min. Next, the PDMS reservoir was removed and the chip was dipped in mineral oil, after which an air pressure was applied to the chip to shear off the excess media from the top of the wells. This process is done to digitize or partition the chip and create individual disconnected wells with cells inside them. The shearing process can also be done with a mineral oil flow from top to bottom of the chip. The chip was then inverted in mineral oil to form inverted hanging nano droplets. These inverted chips were then incubated in 37° C., RH 95% and 5% $CO_2$. The cells were incubated for 9 days in this condition, taken out for 10 minutes daily for imaging and drug loading on Day 3 after cell seeding.

Spheroid Imaging: Real time imaging was done daily after seeding with an upright Olympus BX63 fluorescence microscope with a 10× objective (0.3 NA). For imaging, the chips were kept in oil upright for the duration of imaging and then inverted back for culture once the imaging was complete. Tiles and Z-stacks of 10 um slice thickness of the area with spheroids or shapes were taken of chips in bright-field, GFP and RFP fluorescence wavelengths. The CellTox green fluorescence dye was captured using the GFP fluorescence and the PKH Red dye was captured using the RFP. The spatial pixel size was 1 um×1 um for a depth of 10 um.

Automated Live-cell microscopy with inverted microscope: Live-cell fluorescence microscopy was performed using wide-field illumination on a Zeiss Axio Observer Z1 inverted microscope with a 20× 0.50 NA Plan-Neofluar air objective and 100 W halogen lamp illumination. The microscope was equipped with a temperature and 5% $CO_2$ environmental chamber. The Zeiss ZEN software was used for data acquisition via a Photometrics eXcelon Evolve 512 EMCCD camera. Excitation and emission light was filtered using Zeiss filters (BP 550/25 nm, and BP 605/70 nm respectively). Images were acquired every 3 hours post cell seeding for 72 hrs.

Mate pair library preparation and the bioinformatics pipeline: To generate mate pair libraries from the 3D cultures, an in situ amplification protocol was used. In this protocol, cultured cells were directly applied to a modified Repli-g whole genome amplification (WGA) protocol. WGA DNA (1 µg) from 3D cultures and tumor DNA from the original PDX tumor were fragmented to 3-5 kb using the Covaris E210 and used in the standard Illumina mate pair protocol (version 2) followed by sequencing on the Illumina Hiseq 4000 platform. Sequencing data were processed through bioinformatics algorithms including the SVAtools utility to detect chromosomal rearrangements and summarize the results in "Genome Plots". In these plots, all chromosomes are displayed and arranged in a U-shape. Each line represents a junction identified by the SVAtools. The thickness of the line is relative to the number of fragments supporting the junction. The endpoints of the line indicate the position of the junction's two breakpoints. Diamonds identify a junction where one breakpoint maps to the position shown on the genome plot and the other breakpoint maps to sequences included in reference genome GRCh38 but not within chromosomes 1-22, X or Y, such as unplaced or un-localized contigs, alternate sequences, or mitochondrial DNA. The final plot of 3D cultured cells merged the results of 3 individually cultured chips with arrays of 3D spheroids.

Drug Loading and media exchange protocol: On Day 3 after cell seeding, the chips are loaded with drugs diluted to the desired concentration in media (with serum and dye), except for the negative control chip in which only media was loaded. Media with serum was prepared with CellTox Green Cytotoxicity Assay as explained above. Media with serum for PDX cells included 1% Penicillin-Streptomycin. The drug stock of 10 mM Dasatinib in 100% DMSO was diluted in the media and dye solution to achieve the desired concentration of drug (10 uM to 100 pM). Compensating for the volume of media already in the wells, the concentration of the drug is increased. For example, if the cell culture has 100 wells loaded with spheroids, then the volume of media already present in the wells equaled volume of 1 well*100=10.8 nL*100=1080 nL. During drug loading, if 50 µL of media with drugs is added on this chip, then the final total volume=50+1.08 µL=51.08 µL. So the concentration of the drugs in the 50 µL of media added=(51.08/50)*X; where X is the desired final concentration.

Before drug loading, the chips were first kept upright and centrifuged at 200 g for 5 minutes. Then, 10-50 µL of the drugs/media solution was added in the cell area through the mineral oil layer on the chips. Density of the drugs/media is greater than density of mineral oil. Thus, the increased density allows the drugs/media to settle through the mineral oil and make contact with the wells. Hydrophilic media already inside the wells allow the drug to be spread throughout the area. The chips were then left upright for incubation at room temperature for 30 minutes. Thereafter, the chips were centrifuged again at 400 g for 2 min. The chips were then dipped in mineral oil and the excess media and drugs were sheared off with a mineral oil flow. The chips were then inverted in mineral oil and incubated in 37° C., RH 95% and 5% $CO_2$. The chips were imaged for 6 more days as explained above.

Cell Seeding and Media Exchange Protocol in Geometric Control Experiments

For geometric control experiments, the cell seeding protocol for annular circle, square, and triangle shapes is performed in a single step in the same method as described previously. Briefly, a cured PDMS polymer is attached to the chips, after which the annular channels are made hydrophilic through $O_2$ plasma treatment at 300 W for 3 minutes. Thereafter, off chip cultured cells are stained with PKH dye and the final suspension added to media prepared with CellTox dye, ready to be added to the chip. A cell density of 14,648 cells/mm$^2$ is seeded on chip and centrifuged in a petri dish at 200 g for 2 min. Post centrifugation, the PDMS reservoir is removed and oil shear was performed to create droplet shapes that conform to the shape of the channel cavity due to capillary forces. Finally, the chips are inverted in mineral oil to form inverted hanging droplet shapes. These inverted chips are incubated in 37° C., RH 95% and 5% $CO_2$. The cells are incubated for 3 days in this condition, taken out for 20+35 minutes daily for imaging.

Media exchange for 3D shapes is performed every day in the same manner as the drug loading procedure described above. First, the chips were kept upright for 15 minutes. Thereafter, fresh media was loaded on chip through mineral oil, incubating it for 20 min. Excess media was removed by oil shear post incubation and the chip was inverted back for further culture.

Image Analysis: Each of the z-stack images were converted to Tiff Series, in which a single tiff image of the series was of a single z-stack slice. Autoquant X3 software was then used for 3D deconvolution of the bright-field, green, and red channels of these tiff series images. The 3D deconvolution algorithm utilizes multiple iterations to develop a theoretical point spread function for the fluorescent points for each image. The optical parameters for the deconvolution included pixel spacing of 1 um×1 um×10 um. The objective lens had a numerical aperture of 0.3. The emission wavelengths were 508 nm and 565 nm for green channel (CellTox Dye), and red channel (PKH Red Dye), respectively. The resulting deconvolved images were then analyzed using Imaris (Bitplane) software. In this software, the green and red dye were used to track and calculate the dead cells and analyze the spheroid volumes, respectively. This software utilizes algorithms to identify the local contrast in intensity to determine a threshold for color capture. The cell function was used to determine the green volume of the dead cells and the surface function was used to calculate the volume of the spheroids. Cell and Surface files were exported as excel files, which were used to map the cell death and spheroid volumes in each well. A MATLAB script was created to extract the positional data from each of the cell information and volume information and finally the total volume of the spheroid as well as the total cell death (green volume normalized with red volume) in each well was calculated. The results of each well were plotted against time in line graphs in Excel and box-and-whisker plots of the cell death were generated according to drug concentration in Excel as well. Maximum projections were also obtained from Imaris software.

Confocal Imaging: Samples were fixed in 4% (v v$^{-1}$) of paraformaldehyde overnight in 4° C. then washed with PBS three times and used 0.25% (v v$^{-1}$) diluted Triton-X to permeabilize the cell membrane for 15 min. After washing with PBS, samples were blocked and stored in 1% (w v$^{-1}$) bovine serum albumin (Sigma-Aldrich) at 4° C. overnight. The primary antibodies, rabbit N-Cadherin monoclonal antibody (ThermoFisher) and mouse mitochondria monoclonal antibody (ThermoFisher), were used to stain for cadherin and mitochondria, respectively, at a 1:50 dilution, then incubated overnight at 4° C. Both primary antibodies are human specific. Samples were then washed three times before staining with secondary antibodies. AlexaFluor-568 anti-rabbit (ThermoFisher) and AlexaFluor-488 anti-mouse (ThermoFisher) were used to stain N-cadherin and mitochondria primary antibodies, respectively, and incubated overnight at 4° C. DAPI (ThermoFisher) was used for staining of nucleus and incubated for 1 hour at room temperature. After washing with PBS three times, samples were mounted on the cover glasses by using ProLong Antifade (ThermoFisher). The LSM 710 was used for the confocal fluorescent imaging.

Construction and sequencing of 10× V3.1 Single Cell libraries: Single-cell 3' cDNA libraries are prepared. Three single-cell suspensions with an average viability of 70-75% by acridine orange and propidium iodide (AO/PI) staining on the Nexcelom K2 (Nexcelom Bioscience, Lawrence, MA) were converted into individually barcoded cDNA libraries with the Chromium Next GEM Single-Cell 3' dual-index kit version 3.1 from 10×Genomics (Pleasanton, CA) following the manufacturer's protocols. The target number of cells per library was 6000. The 10×Chromium instrument separates thousands of single cells into Gel Bead Emulsions (GEMs) that add a barcode to the mRNA from each individual cell. Following ds-cDNA synthesis, individually-barcoded libraries compatible with the Illumina chemistry were constructed. The final libraries were quantitated on Qubit and the average size determined on the AATI Fragment Analyzer (Advanced Analytics, Ames, IA). Libraries were pooled evenly and the final pool was diluted to 5 nM concentration and further quantitated by qPCR on a Bio-Rad CFX Connect Real-Time System (Bio-Rad Laboratories, Inc. CA). The final library pool was sequenced on two lanes of an Illumina NovaSeq 6000 SP flowcell as paired-reads with 28 cycles for read 1, 10 cycles for each index read, and 90 cycles for read 2. Basecalling and demultiplexing of raw data was done with the mkfastq command of the software Cell Ranger 4.1 (10×Genomics).

Quantification and analysis of single cell data: The three demultiplexed fastq files are aligned to 10×Genomic's pre-built reference for human (GRCh38) and mouse (mm10) combined (version 2020-A) using the count command of Cell Ranger 4.0.0 with -expect-cell=6000. When using a mixed-species reference, Cell Ranger runs a multiplet detection algorithm on all GEM barcodes associated with >=1 cell (GEM cells). The algorithm starts by separating GEM cells into those with total mouse UMIs>total human UMIs ("mouse" cells) and those with mouse <human ("human" cells). It then uses the 10th percentile of mouse UMI counts in "mouse" cells and human UMI counts in "human" cells to define thresholds to say whether each GEM cell contains both a human and mouse cell (multiplet). Next, the algorithm runs a maximum likelihood estimator for the number of additional GEM cells expected to contain two human cells or two mouse cells based on the observed number of mixed species multiplets and the inferred ratio of cells from each species. Finally, it estimates the total number of individual human and mouse cells, which combined is greater than the number of GEM cells due to multiplets. This algorithm works best when the species ratio is close to 1:1 and there is little ambient RNA from either species in the background. However, our samples greatly skewed toward human cells and there was a small amount of ambient mouse RNA in all called cells (~8-256 UMIs), leading to the algorithm estimating an improbable >90% multiplet rate overall and overestimating the number of mouse cells at 14.8% of mouse+human cells. Instead of using 10×'s algorithm, we input the UMI counts for all GEM cells into R (v4.0.3) using the Seurat package (v3.2.2) and started the same way by summing the total UMI from mouse versus human in each GEM. Additionally, we calculated the total number of mouse versus human genes detected (>=1 UMI) in each GEM. For both total UMI counts and detected genes, we calculated the number of GEMs with human>mouse and we also compared the distributions of values for mouse versus human to estimate the number of GEMs containing a mouse cell versus a human cell.

Further analyses on human cells were performed. First, we excluded all mouse genes and any human genes that were not detected in at least 10 GEMs. Next, we filtered out GEMs with less than 300 human genes detected and where the percentage of UMIs from mitochondrial genes was greater than 3 median absolute deviations (threshold=9.208%). The remaining 7,653 GEMs were then normalized with Seurat's SCTtransform method. The scaled, normalized values of the top 3000 most variable genes were run through principal components analysis then the top 40 PC scores were input to uniform manifold approximation and projection (UMAP) to represent expression variation among the cells in 2-dimensional space. Expression values of marker genes of interest were visualized on the UMAP plots.

REFERENCES

1. Astashkina, A. & Grainger, D. W. Critical analysis of 3-D organoid in vitro cell culture models for high-throughput drug candidate toxicity assessments. Adv. Drug Deliv. Rev. 69-70, 1-18 (2014).
2. Pickl, M. & Ries, C. H. Comparison of 3D and 2D tumor models reveals enhanced HER2 activation in 3D associated with an increased response to trastuzumab. Oncogene 28, 461-468 (2009).
3. Todhunter, M. E. et al. Programmed synthesis of three-dimensional tissues. Nat. Methods 12, 975-981 (2015).
4. Moroni, L. et al. Biofabrication strategies for 3D in vitro models and regenerative medicine. Nature Reviews Materials vol. 3 21-37 (2018).
5. Ryu, N.-E., Lee, S.-H. & Park, H. Spheroid Culture System Methods and Applications for Mesenchymal Stem Cells. Cells 8, 1620 (2019).
6. Yahya, W. N. W., Kadri, N. A. & Ibrahim, F. Cell patterning for liver tissue engineering via dielectrophoretic mechanisms. Sensors (Switzerland) vol. 14 11714-11734 (2014).
7. Nath, S. & Devi, G. R. Three-dimensional culture systems in cancer research: Focus on tumor spheroid model. Pharmacology and Therapeutics vol. 163 94-108 (2016).
8. Ma, H. et al. Multicellular Tumor Spheroids as an in Vivo-Like Tumor Model for Three-Dimensional Imaging of Chemotherapeutic and Nano Material Cellular Penetration. Mol. Imaging 11, 7290.2012.00012 (2012).
9. Baker, L. A., Tiriac, H., Clevers, H. & Tuveson, D. A. Modeling Pancreatic Cancer with Organoids. Trends in Cancer 2, 176-190 (2016).
10. Boj, S. F. et al. Organoid Models of Human and Mouse Ductal Pancreatic Cancer. Cell 160, 324-338 (2015).
11. Clevers, H. Modeling Development and Disease with Organoids. Cell 165, 1586-1597 (2016).
12. Gao, D. et al. Organoid Cultures Derived from Patients with Advanced Prostate Cancer. Cell 159, 176-187 (2014).
13. Baker, B. M. & Chen, C. S. Deconstructing the third dimension—how 3D culture microenvironments alter cellular cues. J. Cell Sci. 125, 3015-3024 (2012).
14. Pampaloni, F., Reynaud, E. G. & Stelzer, E. H. K. The third dimension bridges the gap between cell culture and live tissue. Nat. Rev. Mol. Cell Biol. 8, 839-845 (2007).
15. Mueller-Klieser, W. Three-dimensional cell cultures: from molecular mechanisms to clinical applications. Am. J. Physiol. Physiol. 273, C1109-C1123 (1997).
16. KUNZ-SCHUGHART, L. A., KREUTZ, M. & KNUECHEL, R. Multicellular spheroids: a three-dimensional in vitro culture system to study tumour biology. Int. J. Exp. Pathol. 79, 1-23 (1998).
17. Souza, G. R. et al. Three-dimensional tissue culture based on magnetic cell levitation. Nat. Nanotechnol. 5, 291-296 (2010).
18. Tung, Y.-C. et al. High-throughput 3D spheroid culture and drug testing using a 384 hanging drop array. Analyst 136, 473-478 (2011).
19. Frey, O., Misun, P. M., Fluri, D. A., Hengstler, J. G. & Hierlemann, A.

Reconfigurable microfluidic hanging drop network for multi-tissue interaction and analysis. Nat. Commun. 5, 1-11 (2014).
20. Anderson, A. R. A., Weaver, A. M., Cummings, P. T. & Quaranta, V. Tumor Morphology and Phenotypic Evolution Driven by Selective Pressure from the Microenvironment. Cell 127, 905-915 (2006).
21. Smalley, K. S. M., Brafford, P. A. & Herlyn, M. Selective evolutionary pressure from the tissue microenvironment drives tumor progression. Semin. Cancer Biol. 15, 451-459 (2005).
22. Jorgensen, A. et al. Hanging drop cultures of human testis and testis cancer samples: a model used to investigate activin treatment effects in a preserved niche. Br. J. Cancer 110, 2604-2614 (2014).
23. GravityPLUS™ 3D Culture and Assay Platform. (2013).
24. Long, K. R. & Huttner, W. B. How the extracellular matrix shapes neural development. Open Biology vol. 9 (2019).
25. Aizawa, Y., Owen, S. C. & Shoichet, M. S. Polymers used to influence cell fate in 3D geometry: New trends. Progress in Polymer Science vol. 37 645-658 (2012).
26. Ingber, D. E. Mechanical control of tissue growth: Function follows form. Proceedings of the National Academy of Sciences of the United States of America vol. 102 11571-11572 (2005).
27. Nelson, C. M. et al. Emergent patterns of growth controlled by multicellular form and mechanics. Proc. Natl. Acad. Sci. U.S.A. 102, 11594-11599 (2005).
28. Friedl, P. & Gilmour, D. Collective cell migration in morphogenesis, regeneration and cancer. Nature Reviews Molecular Cell Biology vol. 10 445-457 (2009).
29. Murphy, W. L., McDevitt, T. C. & Engler, A. J. Materials as stem cell regulators. Nature Materials vol. 13 547-557 (2014).
30. Gomez, E. W., Chen, Q. K., Gjorevski, N. & Nelson, C. M. Tissue geometry patterns epithelial-mesenchymal transition via intercellular mechanotransduction. J. Cell. Biochem. n/a-n/a (2010) doi:10.1002/jcb.22545.
31. Boghaert, E. et al. Host epithelial geometry regulates breast cancer cell invasiveness. Proc. Natl. Acad. Sci. U.S.A. 109, 19632-19637 (2012).
32. Lee, J., Abdeen, A. A., Wycislo, K. L., Fan, T. M. & Kilian, K. A. Interfacial geometry dictates cancer cell tumorigenicity. Nat. Mater. 15, 856-862 (2016).
33. Sil, H., Sen, T. & Chatterjee, A. Fibronectin-integrin ($\alpha 5\beta 1$) modulates migration and invasion of murine melanoma cell line B16F10 by involving MMP-9. Oncol. Res. 19, 335-348 (2011).
34. Yang, W., Yu, H., Li, G., Wang, Y. & Liu, L. High-Throughput Fabrication and Modular Assembly of 3D Heterogeneous Microscale Tissues. Small 13, 1602769 (2017).
35. Ganguli, A. et al. Pixelated spatial gene expression analysis from tissue. Nat. Commun. 9, (2018).
36. Fang, Y. & Eglen, R. M. Three-Dimensional Cell Cultures in Drug Discovery and Development. SLAS Discovery vol. 22 456-472 (2017).
37. Kwak, B., Lee, Y., Lee, J., Lee, S. & Lim, J. Mass fabrication of uniform sized 3D tumor spheroid using high-throughput microfluidic system. J. Control. Release 275, 201-207 (2018).
38. Glicklis, R., Merchuk, J. C. & Cohen, S. Modeling mass transfer in hepatocyte spheroids via cell viability, spheroid size, and hepatocellular functions. Biotechnol. Bioeng. 86, 672-680 (2004).
39. Carlson, B. L., Pokorny, J. L., Schroeder, M. A. & Sarkaria, J. N. Establishment, Maintenance, and In Vitro and In Vivo Applications of Primary Human Glioblastoma Multiforme (GBM) Xenograft Models for Translational Biology Studies and Drug Discovery. in Current Protocols in Pharmacology vol. Chapter 14 Unit 14.16 (John Wiley & Sons, Inc., 2011).
40. Ofek, G. et al. Matrix Development in Self-Assembly of Articular Cartilage. PLoS One 3, e2795 (2008).
41. Vasmatzis G, Liu M C, Reganti S, Feathers R W, Smadbeck J, Johnson S H, Schaefer Klein J L, Harris F R, Yang L, Kosari F, Murphy S J, Borad M J, Thompson E A, Cheville J C, A. P. Integration of comprehensive genomic analysis and functional screening of affected molecular pathways to inform cancer therapy. Mayo Clin. Proc. (2019).
42. Nehoff, H. et al. A combination of tyrosine kinase inhibitors, crizotinib and dasatinib for the treatment of glioblastoma multiforme. Oncotarget 6, 37948-37964 (2015).
43. Lewis-Tuffin, L. J. et al. Src family kinases differentially influence glioma growth and motility. Mol. Oncol. 9, 1783-98 (2015).
44. Kovtun, I. V, Murphy, S. J., Johnson, S. H., Cheville, J. C. & Vasmatzis, G. Chromosomal catastrophe is a frequent event in clinically insignificant prostate cancer. Oncotarget 6, 29087-96 (2015).
45. Murphy, S. J. et al. Mate Pair Sequencing of Whole-Genome-Amplified DNA Following Laser Capture Microdissection of Prostate Cancer. DNA Res. 19, 395-406 (2012).
46. Murphy, S. J. et al. Integrated analysis of the genomic instability of PTEN in clinically insignificant and significant prostate cancer. Mod. Pathol. 29, 143-156 (2016).

Statements Regarding Incorporation by Reference and Variations

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

As used herein and in the appended claims, the singular forms "a", "an", and "the" include plural reference unless the context clearly dictates otherwise. Thus, for example, reference to "a cell" includes a plurality of such cells and equivalents thereof known to those skilled in the art. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

When a Markush group or other grouping is used herein, all individual members of the group and all combinations and subcombinations possible of the group are intended to be individually included in the disclosure.

Every device, system, formulation, combination of components, or method described or exemplified herein can be used to practice the invention, unless otherwise stated.

Whenever a range is given in the specification, for example, a size range, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method for preparing a cell and tissue culture, the method comprising the steps of:
    providing an array of surface-oxidized, hydrophilic microwells, wherein each microwell has:
        a depth of between 50 μm to 1000 μm;
        a longest dimension of between 50 μm to 3000 μm;
        a separation distance from an adjacent microwell that prevents unwanted liquid leaking between adjacent microwells;
    forming a removable reservoir over at least a portion of a top surface of the microwells;
    loading a mixture comprising cells in the removable reservoir and forcing the mixture comprising cells in the removable reservoir into the microwells;
    removing the removable reservoir from the microwells;
    covering the microwells with the cells with an immiscible layer;
    partitioning the cells into the individual microwells;
    inverting the array of microwells with the cells and the immiscible layer so that the immiscible layer confines the cells to the individual microwells; and
    culturing the cells in the inverted array of microwells, thereby preparing the cell and tissue culture;
    controlling a shape parameter in at least one cell and tissue culture by providing a microwell geometric shape, wherein the shape parameter is one or more of: cell and tissue culture size, volume, curvature, cross-sectional shape, a thickness, and/or a linear distance,
    wherein the controlling the shape parameter generates a cell and tissue culture shape, thereby generating a mechanical stress distribution on the cell and tissue culture to generate different cell phenotypes within the cell and tissue culture.

2. The method of claim 1, wherein said surface-oxidized hydrophilic microwells comprise: silicon, oxide, glass, or plastic.

3. The method of claim 1, wherein the forcing the mixture comprises centrifuging the microwells and the mixture comprising cells in the removable reservoir at a centrifugal force of between 200 g to 400 g for a time period of between 2 minutes and 5 minutes.

4. The method of claim 1, wherein the removable reservoir comprises an array of microreservoirs addressed to at least a portion of the microwells.

5. The method of claim 4, wherein the removable reservoir comprises polydimethylsiloxane (PDMS).

6. The method of claim 1, wherein the immiscible fluid comprises mineral oil and the cells in the microwells are provided in a culture media.

7. The method of claim 1, wherein the immiscible layer is a liquid and the partitioning step comprises applying a shear stress to the immiscible layer to remove excess liquid and reduce a thickness of the immiscible layer.

8. The method of claim 1, wherein the partitioning step comprises providing a hydrophobic removable reservoir and contacting a top surface of the hydrophobic removable reservoir with mineral oil.

9. The method of claim 1, further comprising the step of:
measuring a change in a cell or tissue physical parameter and/or cell or tissue fluid in which the cell or tissue is immersed with a sensor embedded in the microwells.

10. The method of claim 1, further comprising the step of performing on-chip real-time microscopy of the at least one cell and tissue culture without removal of any cell and tissue culture from a microwell or a component of the cell and tissue culture for changes in cell death and/or variations in cell and tissue cell culture volume over time on a microwell-by-microwell basis.

11. The method of claim 1, wherein the controlling the cell and tissue culture shape is a sphere, rod, cube cylinder, toroid, or combination thereof.

12. The method of claim 1, wherein
a time to form a multicellular spheroid in a plurality of microwells is one-day or less;
the partitioning and immiscible layer avoids or minimizes selective pressure on the cell and tissue culture;
the array of microwells number between 100 and 1,000,000; and/or
each microwell has a volume that is less than 10 μL with an independently-controllable shape parameter testing of the cell and tissue culture geometry on a drug interaction.

13. A method of screening a drug for biological efficacy, the method comprising the steps of:
preparing a cell and tissue culture according to claim 1;
incubating the cell and tissue culture with the drug to allow for contact between the drug and at least a portion of the cell and tissue cultures in the microwells; and
evaluating impact of the drug on the cell and tissue cultures, thereby screening the drug for biological efficacy.

14. The method of claim 13, wherein the cell and tissue culture comprises cancer cells and the drug is a cancer treatment candidate.

15. The method of claim 14, further comprising the steps of:
controlling at least one three-dimensional shape parameter of the at least one cell and tissue culture, wherein the three-dimensional shape parameter is one or more of size, volume, curvature, cross-sectional shape, a thickness, and/or a linear distance; and
evaluating the impact of cell and tissue culture shape on the biological efficacy of the drug.

16. The method of claim 15, wherein a response by the cell and tissue culture to the drug is shape-dependent, with a heterogeneous response within the cell and tissue culture due to a stress gradient that varies over the cell and tissue culture due to the three-dimensional shape parameter that together forms an aggregate response.

17. The method of claim 14, further comprising the steps of:
determining an in-vivo tumor morphology; and
controlling the cell and tissue culture shape parameter to match the cell and tissue culture geometry to the in vivo tumor morphology.

18. The method of claim 14, further comprising the step of controlling the at least one three-dimensional geometric parameter of the at least one cell and tissue culture by:
forming a three-dimensional geometric shape in at least one of the microwells;
wherein the three-dimensional geometric shape comprises an annulus having a cross-sectional shape, a size of the microwell, and/or a cross-sectional shape of the microwell.

19. The method of claim 1, wherein:
each microwell is fluidly connected to an adjacent microwell by a microwell interconnect;
a cell and tissue culture media reservoir is fluidly connected to the array of microwells for introducing culture media and/or a drug to the cell and tissue culture;
the method further comprising the step of exchanging cell and tissue media in contact with the cell and tissue culture in the microwells by introducing a fresh media and/or drug candidate to the cell and tissue culture media reservoir and flowing the fresh media and/or drug candidate to the microwells.

* * * * *